United States Patent
Or et al.

(10) Patent No.: US 8,188,132 B2
(45) Date of Patent: May 29, 2012

(54) LINKED DIBENZIMIDAZOLE DERIVATIVES

(75) Inventors: Yat Sun Or, Watertown, MA (US); Ce Wang, Waltham, MA (US); Xiaowen Peng, Auburndale, MA (US); Lu Ying, Jinhua (CN); Yao-Ling Qiu, Andover, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 12/702,692

(22) Filed: Feb. 9, 2010

(65) Prior Publication Data

US 2010/0221214 A1    Sep. 2, 2010

Related U.S. Application Data

(60) Provisional application No. 61/153,224, filed on Feb. 17, 2009, provisional application No. 61/156,239, filed on Feb. 27, 2009.

(51) Int. Cl.
*A61K 31/4184* (2006.01)
*C07D 403/04* (2006.01)
*C07D 235/14* (2006.01)

(52) U.S. Cl. .................. 514/394; 548/304.7; 548/302.7

(58) Field of Classification Search ............... 548/304.7, 548/302.7; 514/394
See application file for complete search history.

(56) References Cited

U.S. PATENT DOCUMENTS

| | | | |
|---|---|---|---|
| 5,935,982 | A | 8/1999 | Dykstra et al. |
| 7,141,574 | B2 | 11/2006 | Beaulieu et al. |
| 2006/0003942 | A1 | 1/2006 | Tung et al. |
| 2006/0058317 | A1 | 3/2006 | Gravestock et al. |
| 2007/0299068 | A1 | 12/2007 | Karp et al. |
| 2009/0202478 | A1 | 8/2009 | Bachand et al. |
| 2009/0202483 | A1 | 8/2009 | Bachand et al. |
| 2009/0317360 | A1 | 12/2009 | Rai et al. |
| 2010/0221215 | A1 | 9/2010 | Qiu et al. |
| 2010/0221216 | A1 | 9/2010 | Or et al. |
| 2010/0226882 | A1 | 9/2010 | Or et al. |
| 2010/0226883 | A1 | 9/2010 | Qiu et al. |
| 2010/0233122 | A1 | 9/2010 | Qiu et al. |
| 2010/0260708 | A1 | 10/2010 | Belema et al. |
| 2010/0260715 | A1 | 10/2010 | Or et al. |
| 2010/0266543 | A1 | 10/2010 | Qiu et al. |
| 2010/0305117 | A1 | 12/2010 | Herdewijn et al. |
| 2010/0310512 | A1 | 12/2010 | Guo et al. |
| 2010/0316607 | A1 | 12/2010 | Or et al. |
| 2011/0008288 | A1 | 1/2011 | Or et al. |
| 2011/0064695 | A1 | 3/2011 | Qiu et al. |
| 2011/0064696 | A1 | 3/2011 | Or et al. |
| 2011/0064697 | A1 | 3/2011 | Qiu et al. |
| 2011/0064698 | A1 | 3/2011 | Or et al. |
| 2011/0070196 | A1 | 3/2011 | Qiu et al. |
| 2011/0070197 | A1 | 3/2011 | Or et al. |

FOREIGN PATENT DOCUMENTS

| | | |
|---|---|---|
| JP | 2000299186 | 10/2000 |
| WO | 2006133326 A1 | 12/2006 |
| WO | 2008021927 A2 | 2/2008 |
| WO | 2008021928 A2 | 2/2008 |
| WO | 2008021936 A2 | 2/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2010014744 A1 | 2/2010 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010096302 A1 | 8/2010 |
| WO | 2010096777 A1 | 8/2010 |
| WO | 2010111483 A1 | 9/2010 |

(Continued)

OTHER PUBLICATIONS

Obach, R.S., Drug-drug interactions; An important negative attribute in drugs, 2003, Drugs of Today, 39(5), p. 301-338.*

(Continued)

*Primary Examiner* — Andrew D Kosar
*Assistant Examiner* — Karen Cheng
(74) *Attorney, Agent, or Firm* — Edgar W. Harlan; Carolyn S. Elmore; Elmore Patent Law Group PC

(57) ABSTRACT

The present invention discloses compounds of Formula (I), or pharmaceutically acceptable salts, esters, or prodrugs thereof:

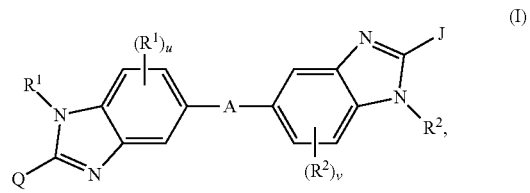

(I)

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

31 Claims, No Drawings

FOREIGN PATENT DOCUMENTS

| | | |
|---|---|---|
| WO | 2010111534 A1 | 9/2010 |
| WO | 2010111673 A1 | 9/2010 |
| WO | 2010117635 A1 | 10/2010 |
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A1 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |

OTHER PUBLICATIONS

Accession No. 2044678522, 3-Thiophenecarboxamide, N-[[6-[[2-[[(2-thienylcarbonyl) amino]methyl]-1H-benzimidazol-6-yl]methyl]-1H-benzimidazol-2-yl]methyl]-, Chemical Library, Mar. 1, 2010.

Accession No. 2081170195, CAS Index Name Not Yet Assigned, Chemical Library, Mar. 1, 2010.

Accession No. 2043072999, 1H-Benzimidazole-2-methanamine, 5,5'-methylenebis-, Chemical Library, Jan. 25, 2008.

Accession No. 2032228315, Chemical Name Not Yet Assigned, Chemical Library, Oct. 15, 2008.

Registry No. 894365607, Index Name Not Yet Assigned, Chemical Library, Jul. 19, 2006.

Accession No. 2044678524, 3-Furancarboxamide, N-[[6-[[2-[[(2-furanylcarbonyl) amino]methyl]-1H-benzimidazol-6-yl]methyl]-1H-benzimidazol-2-yl]methyl]-, Chemical Library, Mar. 1, 2010.

Registry No. 894365685, 3-Thiophenecarboxamide, N-[[6-[[2-[[(2-thienylcarbonyl) amino]methyl]-1H-benzimidazol-6-yl]methyl]-1H-benzimidazol-2-yl]methyl]-, Chemical Library, Jul. 19, 2006.

Registry No. 894365641, Index Name Not Yet Assigned, Chemical Library, Jul. 19, 2006.

Registry No. 894365721, 3-Furancarboxamide, N-[[6-[[2-[[(2-furanylcarbonyl) amino]methyl]-1H-benzimidazol-6-yl]methyl]-1H-benzimidazol-2-yl]methyl]-, Chemical Library, Jul. 19, 2006.

Registry No. 309941579, 1H-Benzimidazole-2-methanamine, 5,5'-methylenebis-, Chemical Library, Dec. 20, 2000.

Bressanelli, et al., "Cyrstal Structure of the RNA-Dependent RNA Polymerase of Hepatitis C Virus," PNAS, vol. 96, pp. 13034-13039, 1999.

International Search Report for PCT/US10/23645, dated Mar. 18, 2010.

Katritzky, A. R., et al., "Further Polymers Derived from Bisazlactones and Tetraamino Compounds," Journal of Polymer Science: Part A: Polymer Chemistry, vol. 27, pp. 1515-1524, 1989.

U.S. Appl. No. 12/702,673, Qiu, et al.
U.S. Appl. No. 12/702,802, Qiu, et al.
U.S. Appl. No. 12/707,190, Or, et al.
U.S. Appl. No. 12/707,210, Or, et al.
U.S. Appl. No. 13/013,212, Qiu, et al.
U.S. Appl. No. 13/082,621, Qiu, et al.

* cited by examiner

LINKED DIBENZIMIDAZOLE DERIVATIVES

RELATED APPLICATION

This application claims the benefit of U.S. Provisional Application No. 61/153,224, filed Feb. 17, 2009 and U.S. Provisional Application No. 61/156,239 filed Feb. 27, 2009. The entire teachings of the above applications are incorporated herein by reference.

TECHNICAL FIELD

The present invention relates to novel antiviral agents. More specifically, the present invention relates to compounds which can inhibit the function of the NS5A protein encoded by Hepatitis C virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA—A Publication of the RNA Society. 1(5): 526-537, 1995 Jul.). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et al (1996) EMBO J. 151 2-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4): 2046-2051). Thus, inhibition of NS5B RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1; and in Rice, C. M. *Nature* 2005, 435, 374.

Based on the foregoing, there exists a significant need to identify compounds with the ability to inhibit HCV. A general strategy for the development of antiviral agents is to inactivate virally encoded proteins, including NS5A, that are essential for the replication of the virus. The relevant patent disclosures describing the synthesis of HCV NS5A inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/1333262; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; WO 2008/048589, the contents of each of which are expressly incorporated by reference herein.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I):

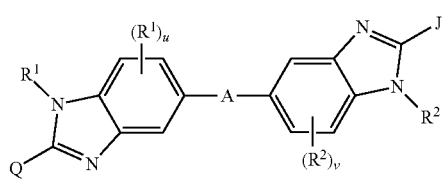

or a pharmaceutically acceptable salt thereof, wherein:

A is an optionally substituted linear aliphatic group;

$R^1$ and $R^2$ at each occurrence are each independently selected from the group consisting of hydrogen, halogen, cyano, optionally substituted $C_1$-$C_4$ alkyl, —O—$R^{11}$, —$NR^aR^b$, —C(O)$R^{11}$, —$CO_2R^{11}$, and —C(O)$NR^aR^b$; preferably hydrogen, halogen and optionally substituted $C_1$-$C_4$ alkyl;

$R^{11}$ at each occurrence is independently hydrogen or optionally substituted $C_1$-$C_8$ alkyl; and $R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;

u and v at each occurrence are each independently 1, 2, or 3;

Q and J are each independently selected from:

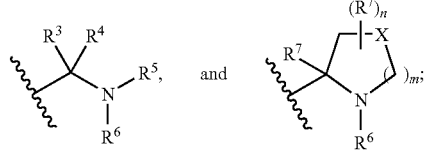

wherein:

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably hydrogen or optionally substituted $C_1$-$C_4$ alkyl; or alternatively, $R^3$ and $R^4$ can be taken together with the carbon atom to which they are attached to form optionally substituted $C_3$-$C_8$ cycloalkyl or optionally substituted heterocyclic;

$R^5$ at each occurrence is independently hydrogen, optionally substituted $C_1$-$C_8$ alkyl, or optionally substituted $C_3$-$C_8$ cycloalkyl; preferably hydrogen or optionally substituted $C_1$-$C_4$ alkyl;

$R^6$ at each occurrence is independently selected from the group consisting of —C(O)—$R^{12}$, —C(O)—C(O)—$R^{12}$, $S(O)_2$—$R^{12}$, and —C(S)—$R^{12}$, preferably —C(O)—$R^{12}$, more preferably an optionally substituted amino acid acyl;

$R^{12}$ at each occurrence is independently selected from the group consisting of: —O—$R^{11}$, —$NR^aR^b$, —$R^{13}$, and —$NR^cR^d$, preferably optionally substituted $C_1$-$C_8$ alkyl and —O—$R^{11}$;

$R^{13}$ at each occurrence is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably optionally substituted $C_1$-$C_8$ alkyl; more preferably $C_1$-$C_8$ alkyl optionally substituted with amino, hydroxy, optionally substituted phenyl, protected amino, or O($C_1$-$C_4$ alkyl); and $R^c$ and $R^d$ at each occurrence are each independently selected from the group consisting of hydrogen, —$R^{13}$, —C(O)—$R^{13}$, —C(O)—$OR^{13}$, —$S(O)_2$—$R^{13}$, —C(O)N$(R^{13})_2$, and —$S(O)_2N(R^{13})_2$;

m is 0, 1, or 2, preferably 1;

n is 1, 2, 3, or 4, preferably 1 or 2;

X at each occurrence is independently selected from O, S, S(O), $SO_2$, and $C(R^7)_2$, preferably $CH_2$ or $CHR^7$; provided that when m is 0, X is $C(R^7)_2$; and $R^7$ at each occurrence is independently selected from the group consisting of hydrogen, halogen, cyano, —O—$R^{11}$, —$NR^aR^b$, optionally substituted aryl, optionally substituted heteroaryl, and optionally substituted —$C_1$-$C_4$ alkyl; preferably hydrogen, methyl or halogen; or two vicinal $R^7$ groups can be taken together with the two adjacent atoms to which they are attached to form a fused, optionally substituted $C_3$-$C_8$ cycloalkyl or optionally substituted heterocyclic ring; preferably a fused, optionally substituted cyclopropyl; or alternatively, two geminal $R^7$ groups can be taken together with the carbon atom to which they are attached to form a spiro, optionally substituted $C_3$-$C_8$ cycloalkyl or optionally substituted heterocyclic ring; preferably a spiro, optionally substituted cyclopropyl.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, or a pharmaceutically acceptable salt thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. Provisional Application Ser. No. 61/151,079 filed Feb. 9, 2009 entitled "Linked Dibenzimidazole Antivirals"; U.S. Provisional Application Ser. No. 61/153,231 filed Feb. 17, 2009 entitled "Linked Dibenzimidazole Derivatives" and U.S. Provisional Application No. 61/156,110 file Feb. 27, 2009 entitled "Linked Dibenzimidazole Derivatives," the contents of each of which are expressly incorporated by reference herein.

In an embodiment, the present invention relates to compounds of Formula (Ia), or a pharmaceutically acceptable salt thereof:

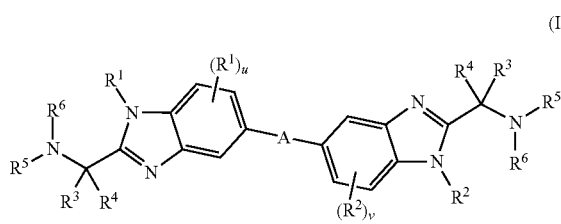

(Ia)

wherein A, u, v, $R^1$, $R^2$, $R^3$, $R^4$, $R^5$ and $R^6$ are as previously defined.

In another embodiment, the present invention relates to compounds of Formula (Ib), or a pharmaceutically acceptable salt thereof:

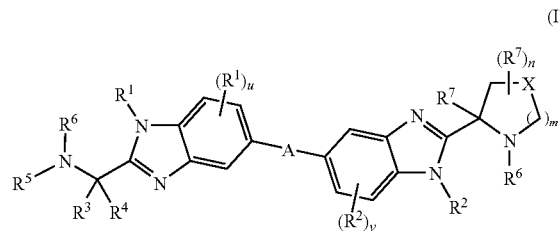

(Ib)

wherein A, u, v, m, n, $R^1$, $R^2$, $R^3$, $R^4$, $R^5$, $R^6$, $R^7$ and X are as previously defined.

In yet another embodiment, the present invention relates to compounds of Formula (Ic), or a pharmaceutically acceptable salt thereof:

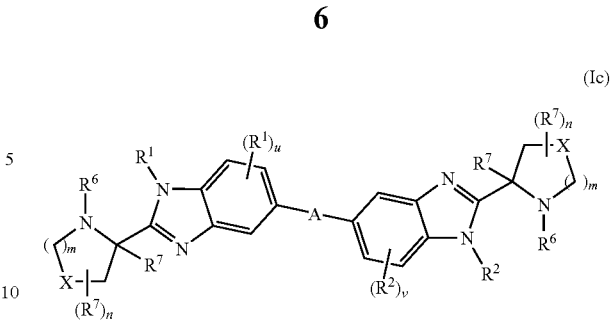

(Ic)

wherein A, u, v, m, n, $R^1$, $R^2$, $R^6$, $R^7$ and X are as previously defined.

In still another embodiment, the present invention relates to compounds of Formula (Id), or a pharmaceutically acceptable salt thereof:

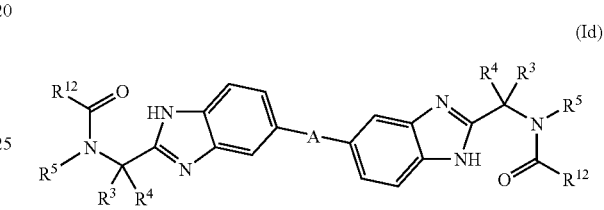

(Id)

wherein A, $R^3$, $R^4$, $R^5$ and $R^{12}$ are as previously defined.

In still another embodiment, the present invention relates to compounds of Formula (Ie), or a pharmaceutically acceptable salt thereof:

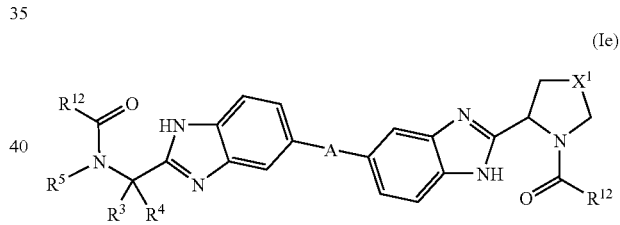

(Ie)

wherein A, $R^3$, $R^4$, $R^5$ and $R^{12}$ are as previously defined and $X^1$ is $CH_2$, CHF, CH(OH), or $CF_2$.

In still another embodiment, the present invention relates to compounds of Formula (If), or a pharmaceutically acceptable salt thereof:

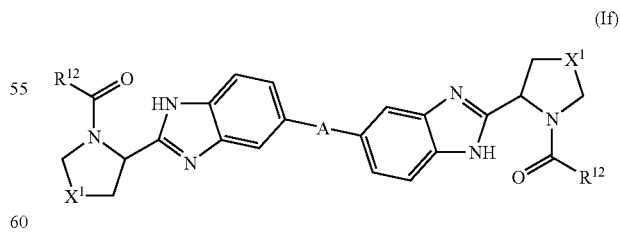

(If)

wherein A, $X^1$ and $R^{12}$ are as previously defined.

In still another embodiment, the present invention relates to compounds of Formula (If), wherein $R^{12}$ is $C_1$-$C_8$ alkyl optionally substituted with amino, hydroxy, phenyl, protected amino, or O($C_1$-$C_4$ alkyl); or a pharmaceutically acceptable salt thereof.

In still another embodiment of the present invention, the absolute stereochemistry of the pyrrolidine and 2-benzimidazolylmethylamine moiety is represented by Formulae (Ig-1, Ig-2 and Ig-3):

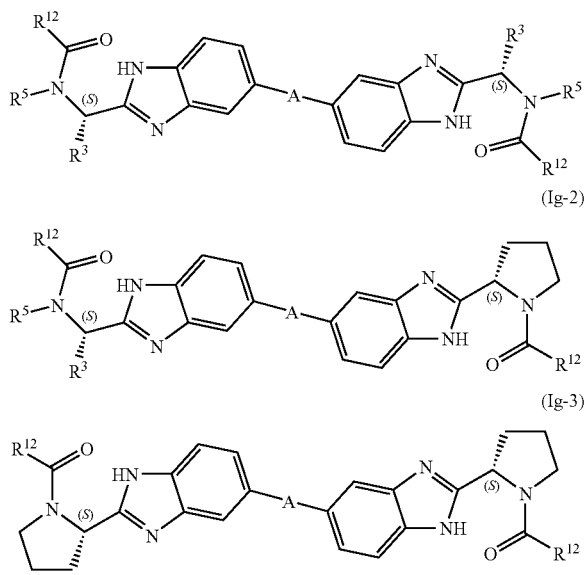

wherein A, $R^3$, $R^5$, and $R^{12}$ are as previously defined.

In still another embodiment, the present invention relates to compounds of Formula (Ih), or a pharmaceutically acceptable salt thereof:

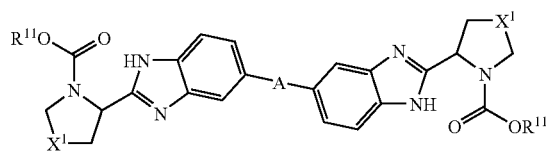

wherein A, $X^1$ and $R^{11}$ are as previously defined.

In still another embodiment, the present invention relates to compounds of Formula (Ii), or a pharmaceutically acceptable salt thereof:

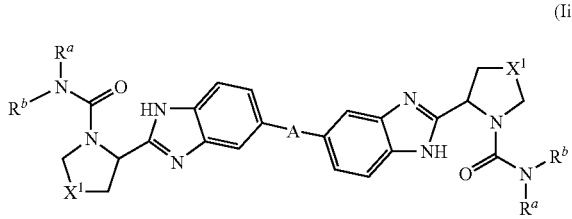

wherein A, $X^1$, $R^a$ and $R^b$ are as previously defined.

In still another embodiment, the present invention relates to compounds of Formula (Ij), or a pharmaceutically acceptable salt thereof:

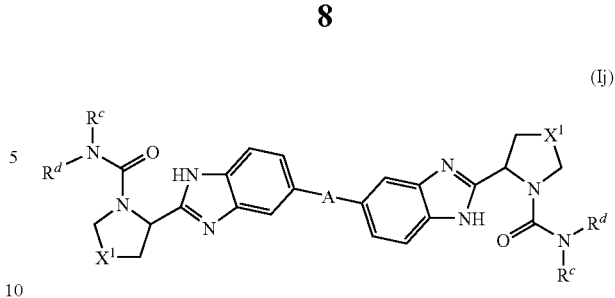

wherein A, $X^1$, $R^c$ and $R^d$ are as previously defined.

In still another embodiment, the present invention relates to compounds of Formula (Ik), or a pharmaceutically acceptable salt thereof:

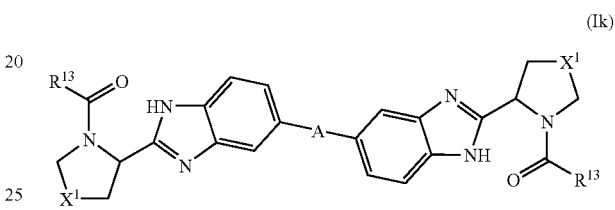

wherein A, $X^1$ and $R^{13}$ are as previously defined.

In still another embodiment, the present invention relates to compounds of Formula (II), or a pharmaceutically acceptable salt thereof:

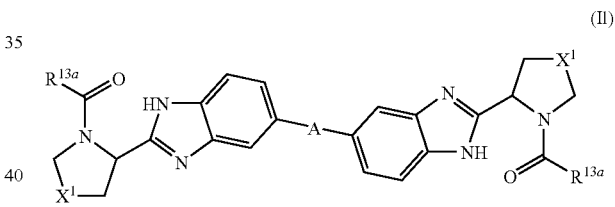

wherein A and $X^1$ are as previously defined and $R^{13a}$ at each occurrence is independently an optionally substituted $C_1$-$C_8$ alkyl; preferably $C_1$-$C_8$ alkyl optionally substituted with amino, hydroxy, phenyl, protected amino, or $O(C_1$-$C_4$ alkyl).

In still another embodiment, the present invention relates to compounds of Formula (IIa), or a pharmaceutically acceptable salt thereof:

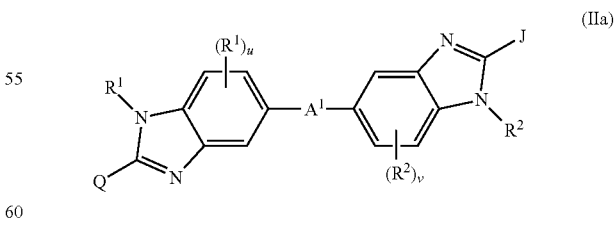

wherein Q, J, u, v, $R^1$ and $R^2$ are as previously defined and $A^1$ is $C_1$-$C_8$ alkyl, preferably $C_3$-$C_6$ alkyl, each optionally substituted.

In still another embodiment, the present invention relates to compounds of Formula (IIb), or a pharmaceutically acceptable salt thereof:

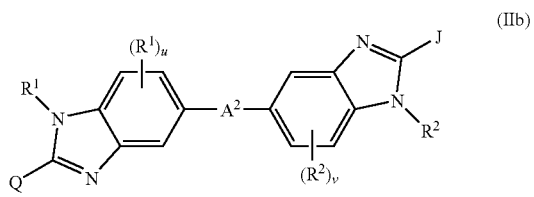

wherein Q, J, u, v, R¹ and R² are as previously defined and A² is $C_2$-$C_8$ alkenyl, preferably $C_3$-$C_6$ alkenyl, each optionally substituted.

In still another embodiment, the present invention relates to compounds of Formula (IIc), or a pharmaceutically acceptable salt thereof:

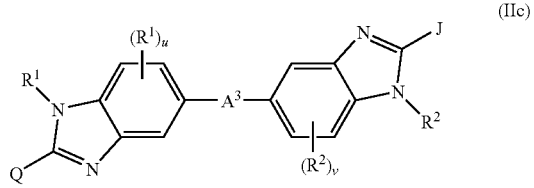

wherein Q, J, u, v, R¹ and R² are as previously defined and A³ is $C_2$-$C_8$ alkynyl, preferably $C_3$-$C_6$ alkynyl, each optionally substituted.

In still another embodiment, the present invention relates to compounds of Formula (IId), or a pharmaceutically acceptable salt thereof:

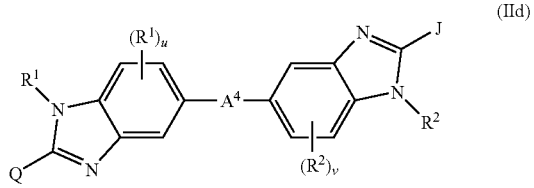

wherein Q, J, u, v, R¹ and R² are as previously defined; and A⁴ is a linear aliphatic group containing a group selected from C(O), S(O)$_2$, C(O)O, C(O)N(R¹¹), OC(O)O, OC(O)N(R¹¹), S(O)$_2$N(R¹¹), N(R¹¹)C(O)N(R¹¹), N(R¹¹)C(O)C(O)N(R¹¹), N(R¹¹)S(O)$_2$N(R¹¹), C(O)N(R¹¹)S(O)$_2$ or C(O)N(R¹¹)S(O)$_2$N(R¹¹); and R¹¹ is as previously defined.

In still another embodiment, the present invention relates to compounds of Formula (IIe), or a pharmaceutically acceptable salt thereof:

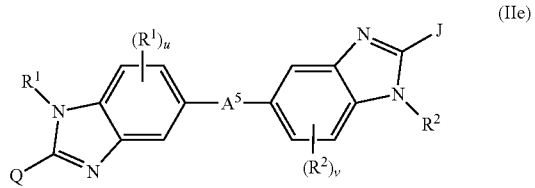

wherein Q, J, u, v, R¹ and R² are as previously defined; and A⁵ is a linear aliphatic group containing an olefinic double bond and a group selected from C(O), S(O)$_2$, C(O)O, C(O)N(R¹¹), OC(O)O, OC(O)N(R¹¹), S(O)$_2$N(R¹¹), N(R¹¹)C(O)N(R¹¹), N(R¹¹)C(O)C(O)N(R¹¹), N(R¹¹)S(O)$_2$N(R¹¹), C(O)N(R¹¹)S(O)$_2$ or C(O)N(R¹¹)S(O)$_2$N(R¹¹); and R¹¹ is as previously defined.

In still another embodiment, the present invention relates to compounds of Formula (IIf), or a pharmaceutically acceptable salt thereof:

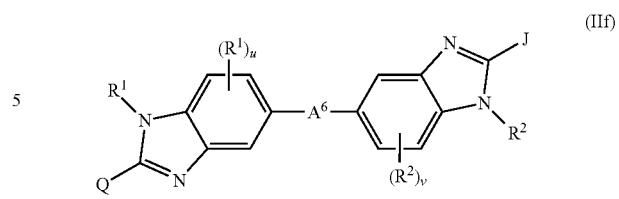

wherein Q, J, u, v, R¹ and R² are as previously defined; and A⁶ is a linear aliphatic group containing an alkynic triple bond and a group selected from C(O), S(O)$_2$, C(O)O, C(O)N(R¹¹), OC(O)O, OC(O)N(R¹¹), S(O)$_2$N(R¹¹), N(R¹¹)C(O)N(R¹¹), N(R¹¹)C(O)C(O)N(R¹¹), N(R¹¹)S(O)$_2$N(R¹¹), C(O)N(R¹¹)S(O)$_2$ or C(O)N(R¹¹)S(O)$_2$N(R¹¹); and R¹¹ is as previously defined.

In still another embodiment, the present invention relates to compounds of Formula (IIg), or a pharmaceutically acceptable salt thereof:

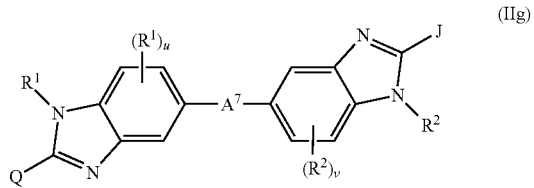

wherein Q, J, u, v, R¹ and R² are as previously defined; and A⁷ is a linear aliphatic group containing one or more groups independently selected from O and N(R¹¹); and R¹¹ is as previously defined.

In still another embodiment, the present invention relates to compounds of Formula (IIh), or a pharmaceutically acceptable salt thereof:

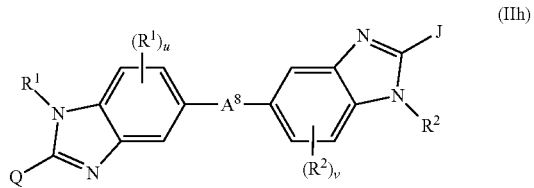

wherein Q, J, u, v, R¹ and R² are as previously defined; and A⁸ is a linear aliphatic group containing an olefinic double bond and one or more groups independently selected from O and N(R¹¹); and R¹¹ is as previously defined.

In still another embodiment, the present invention relates to compounds of Formula (IIi), or a pharmaceutically acceptable salt thereof:

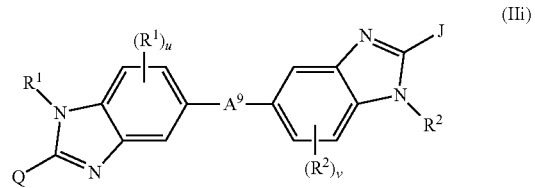

wherein Q, J, u, v, R¹ and R² are as previously defined; and A⁹ is a linear aliphatic group containing an alkynic triple bond and one or more groups independently selected from O and N(R¹¹); and R¹¹ is as previously defined.

In still another embodiment, the present invention relates to compounds of Formula (IIIa), or a pharmaceutically acceptable salt thereof:

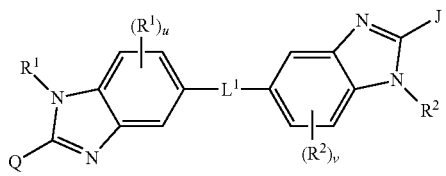

(IIIa)

wherein Q, J, u, v, R¹ and R² are as previously defined and L¹ is selected from C(O), S(O)$_2$, C(O)O, C(O)N(R$^{11}$), OC(O)O, OC(O)N(R$^{11}$), S(O)$_2$N(R$^{11}$), N(R$^{11}$)C(O)N(R$^{11}$), N(R$^{11}$)C(O)C(O)N(R$^{11}$), N(R$^{11}$)S(O)$_2$N(R$^{11}$), C(O)N(R$^{11}$)S(O)$_2$ or C(O)N(R$^{11}$)S(O)$_2$N(R$^{11}$); and R$^{11}$ is as previously defined.

In still another embodiment, the present invention relates to compounds of Formula (IIIb), or a pharmaceutically acceptable salt thereof:

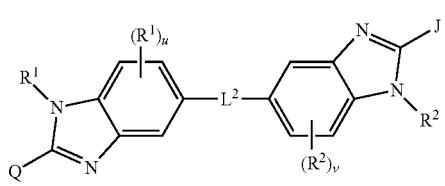

(IIIb)

wherein Q, J, u, v, R¹ and R² are as previously defined and L² is a linear aliphatic group containing one to four carbons and two groups independently selected from O, N(R$^{11}$), C(O), S(O)$_2$, C(O)O, C(O)N(R$^{11}$), OC(O)O, OC(O)N(R$^{11}$), S(O)$_2$N(R$^{11}$), N(R$^{11}$)C(O)N(R$^{11}$), N(R$^{11}$)S(O)$_2$N(R$^{11}$), C(O)N(R$^{11}$)S(O)$_2$ or C(O)N(R$^{11}$)S(O)$_2$N(R$^{11}$); and R$^{11}$ is as previously defined.

In still another embodiment, the present invention relates to compounds of Formula (I), or a pharmaceutically acceptable salt thereof; wherein

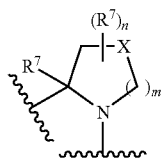

at each occurrence is independently illustrated by one of the following groups:

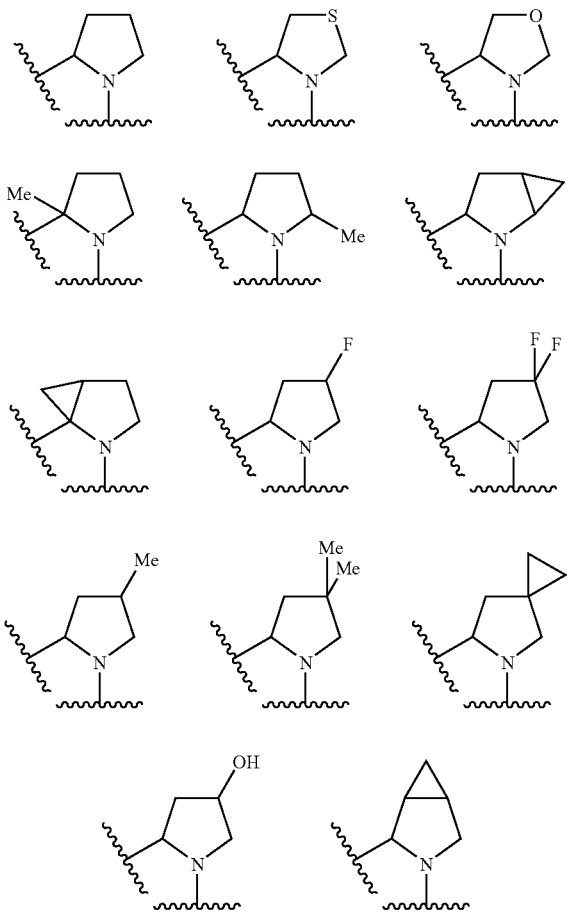

Representative compounds of the present invention are those selected from compounds 1-352, 1a, 3a, and 353-357 compiled in the following tables:

TABLE 1

Compounds 1-219

TABLE 1-continued

Compounds 1-219

TABLE 1-continued
Compounds 1-219
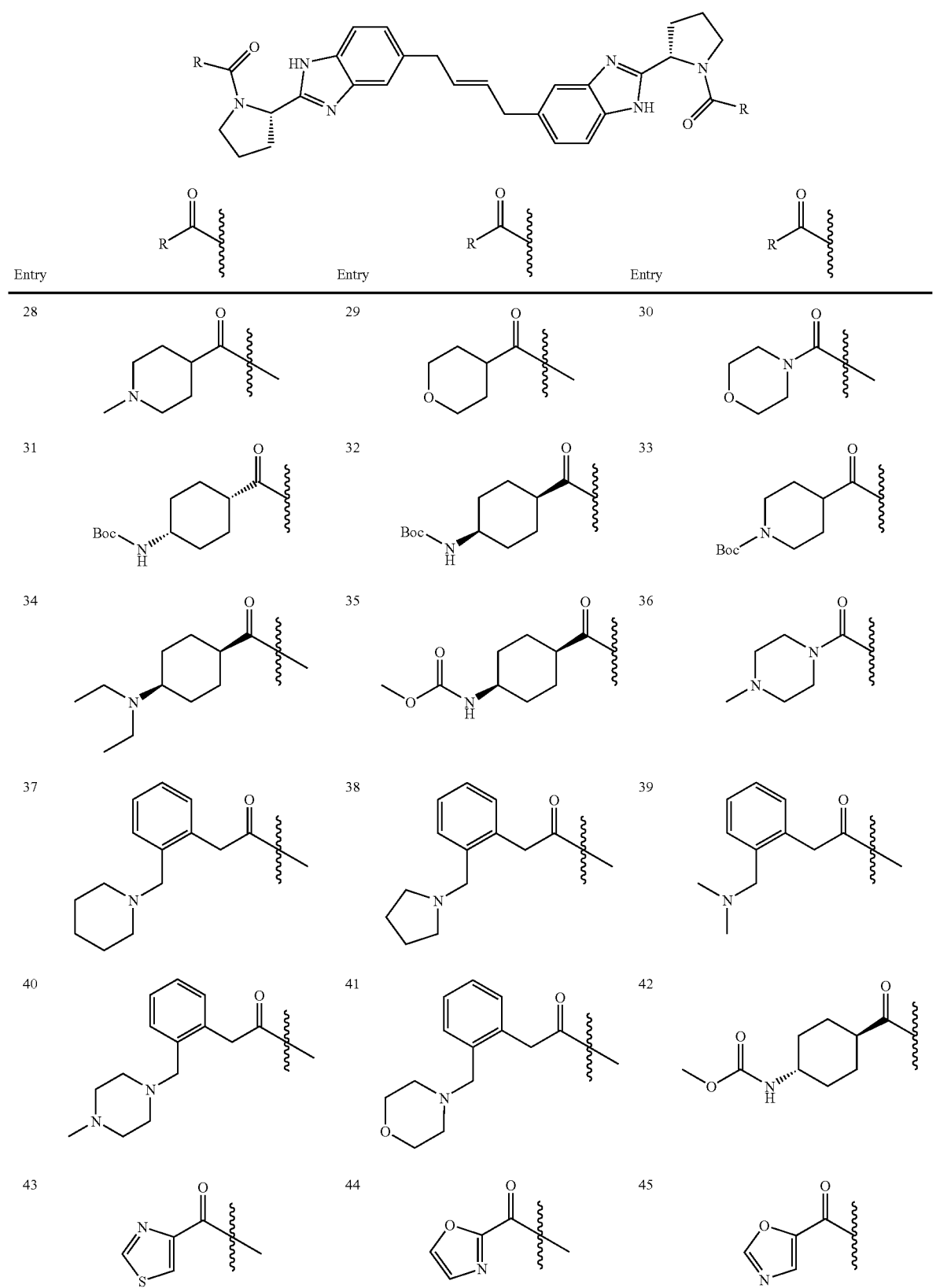

TABLE 1-continued

Compounds 1-219

US 8,188,132 B2
TABLE 1-continued
Compounds 1-219
| Entry | | Entry | | Entry | |
|---|---|---|---|---|---|
| 67 | 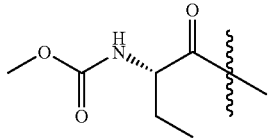 | 68 | 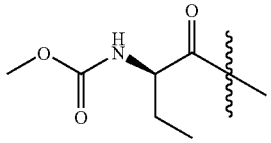 | 69 | 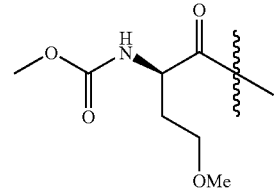 |
| 70 | 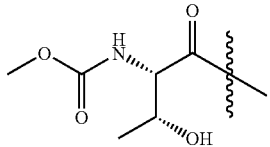 | 71 | 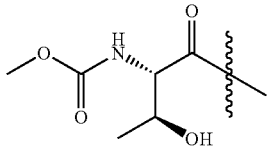 | 72 | 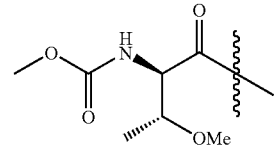 |
| 73 | 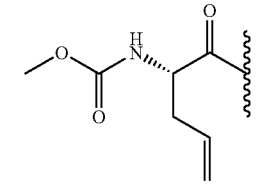 | 74 | 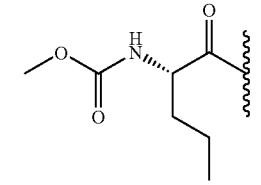 | 75 | 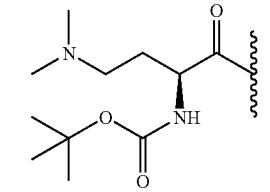 |
| 76 | 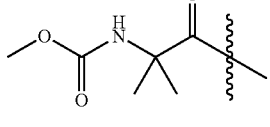 | 77 | 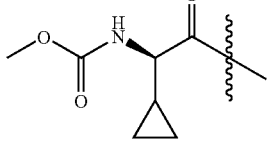 | 78 | 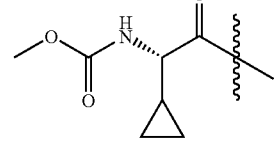 |
| 79 | 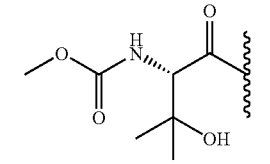 | 80 | 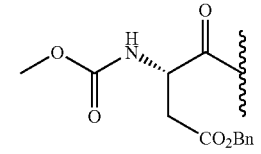 | 81 | 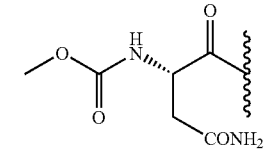 |
| 82 | 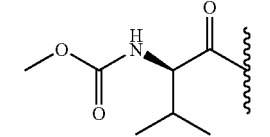 | 83 | 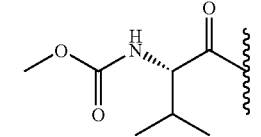 | 84 | 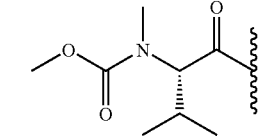 |

TABLE 1-continued

Compounds 1-219

TABLE 1-continued

Compounds 1-219

TABLE 1-continued

Compounds 1-219

TABLE 1-continued

Compounds 1-219

TABLE 1-continued

Compounds 1-219

| Entry | | Entry | | Entry | |
|---|---|---|---|---|---|
| 151 | piperazinone-CH(Ph)-C(=O)- | 152 | morpholine-CH(Ph)-C(=O)- | 153 | piperidine-CH(Ph)-C(=O)- |
| 154 | Cbz-piperazine-CH(Ph)-C(=O)- | 155 | 2-CF₃-C₆H₄-CH(NMe₂)-C(=O)- | 156 | 3-CF₃-C₆H₄-CH(NMe₂)-C(=O)- |
| 157 | 3-pyridyl-CH(NMe₂)-C(=O)- | 158 | 2-pyridyl-CH(NMe₂)-C(=O)- | 159 | 4-pyridyl-CH(NMe₂)-C(=O)- |
| 160 | 3-Cl-C₆H₄-CH(NMe₂)-C(=O)- | 161 | 2-Cl-C₆H₄-CH(NMe₂)-C(=O)- | 162 | 6-Cl-3-pyridyl-CH(NMe₂)-C(=O)- |
| 163 | 2-F-C₆H₄-CH(NMe₂)-C(=O)- | 164 | 2-Cl-C₆H₄-CH(NMe₂)-C(=O)- | 165 | 4-Cl-C₆H₄-CH(NMe₂)-C(=O)- |
| 166 | 2-F-C₆H₄-CH(NMe₂)-C(=O)- | 167 | 2-F-C₆H₄-CH(NMe₂)-C(=O)- | 168 | 3-F-C₆H₄-CH(NMe₂)-C(=O)- |

TABLE 1-continued

Compounds 1-219

| Entry | | Entry | | Entry | |
|---|---|---|---|---|---|
| 169 | piperidine-(2-fluorophenyl)-CH-C(O)- | 170 | 4-O2N-C6H4-CH(NMe2)-C(O)- | 171 | 2-methylthiazol-4-yl-CH(NMe2)-C(O)- |
| 172 | benzo[d]isoxazol-3-yl-CH(NMe2)-C(O)- | 173 | thiophen-2-yl-CH(NMe2)-C(O)- | 174 | thiophen-3-yl-CH(NMe2)-C(O)- |
| 175 | quinolin-3-yl-CH(NMe2)-C(O)- | 176 | benzo[b]thiophen-3-yl-CH(NMe2)-C(O)- | 177 | 2-methylbenzo[d]thiazol-5-yl-CH(NMe2)-C(O)- |
| 178 | PhCH2-N(Me)-CH2-C(O)- | 179 | naphthalen-1-yl-CH(NMe2)-C(O)- | 180 | pyrrolidin-1-yl-CH2-C(O)- |
| 181 | 4-methylpiperazin-1-yl-CH2-C(O)- | 182 | Me2N-CH2-C(O)- | 183 | Et2N-CH(CH2OMe)-C(O)- |
| 184 | PhCH2-N(Me)-CH(Me)-C(O)- | 185 | (n-Pr)2N-CH(Me)-C(O)- | 186 | (n-Pr)2N-CH(Me)-C(O)- |

TABLE 1-continued

Compounds 1-219

TABLE 1-continued
Compounds 1-219
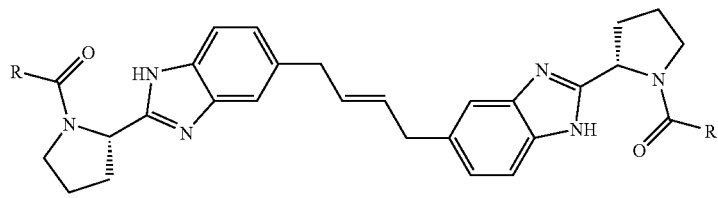

TABLE 2
Compounds 220-229
| Entry | R | R' | R" | X | Entry | R | R' | R" | X |
|---|---|---|---|---|---|---|---|---|---|
| 220 | Me | H | H | CH₂ | 221 | H | H | H | CF₂ |
| 222 | Me | H | H | S | 223 | H | H | H | (H, F stereo) |
| 224 | Me | H | H | O | 225 | H | H | H | (F, H stereo) |
| 226 | H | Ph | H | CH₂ | 227 | H | H | H | (H, OH stereo) |
| 228 | H | H | Ph | CH₂ | 229 | H | H | H | (OH, H stereo) |
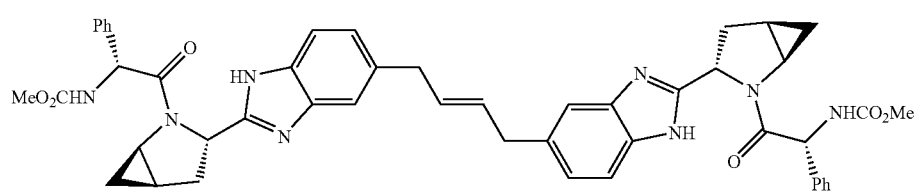
Compound 230
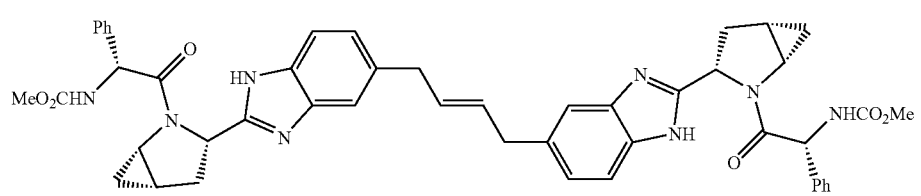
Compound 231
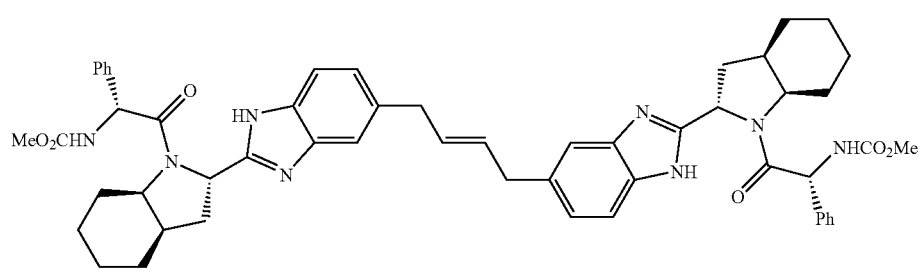
Compound 232

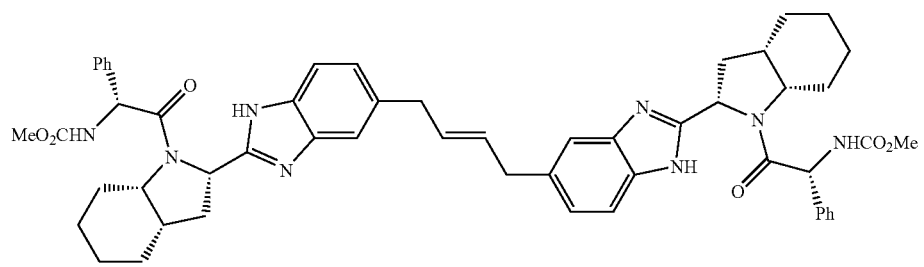
Compound 233
TABLE 3
Compounds 234-243
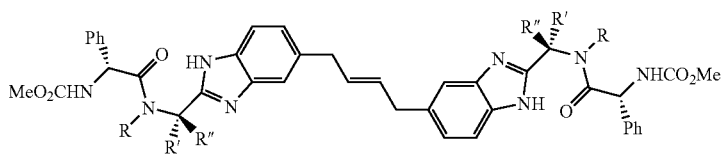
| Entry | R | R' | R" | Entry | R | R' | R" |
|-------|------|--------|----|-------|-----------|------------|----|
| 234 | Me | Me | H | 235 | H | Me | H |
| 236 | Me | H | Me | 237 | cyclopropyl | Me | H |
| 238 | Me | Me | Me | 239 | Me | cyclopropyl | H |
| 240 | Me | Allyl | H | 241 | Et | Me | H |
| 242 | Me | CHMe₂ | H | 243 | Me | Et | H |
TABLE 4
Compounds 244-263
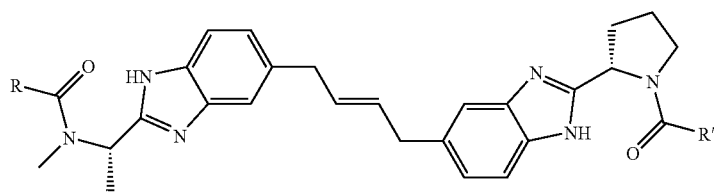
| Entry | R | R' | Entry | R | R' |
|-------|-----------------|-----------------|-------|-----------------|-----------------|
| 244 | MeO₂CHN-CH(Ph)- | MeO₂CHN-CH(Ph)- | 245 | Me₂N-CH(Ph)- | Me₂N-CH(Ph)- |
| 246 | Me₂N-CH(Ph)- | MeO₂CHN-CH(Ph)- | 247 | MeO₂CHN-CH(Ph)- | Me₂N-CH(Ph)- |
| 248 | MeO₂CHN-CH(iPr)- | MeO₂CHN-CH(Ph)- | 249 | MeO₂CHN-CH(Ph)- | MeO₂CHN-CH(iPr)- |

TABLE 4-continued
Compounds 244-263
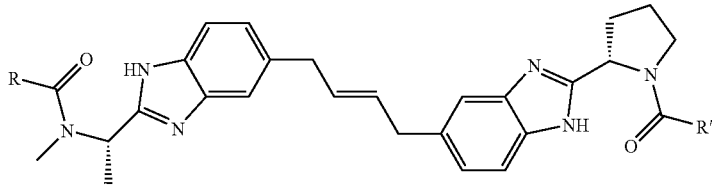
| Entry | R | R' | Entry | R | R' |
|---|---|---|---|---|---|
| 250 | 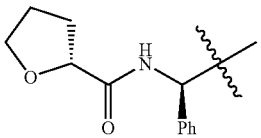 | 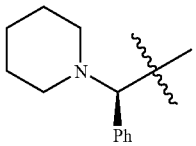 | 251 | 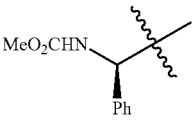 | 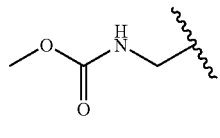 |
| 252 | 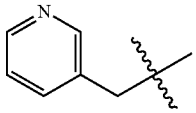 | 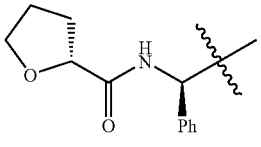 | 253 | 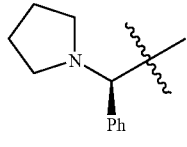 | 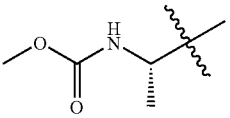 |
| 254 | 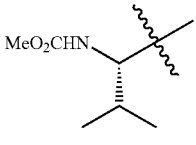 | 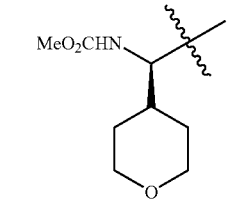 | 255 | 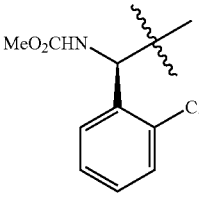 | 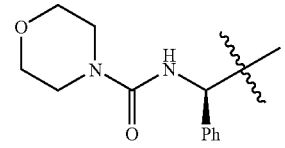 |
| 256 | 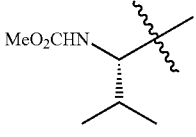 | 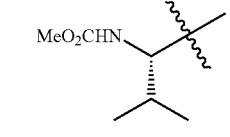 | 257 | 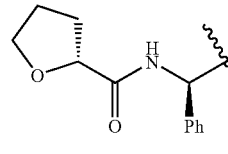 | 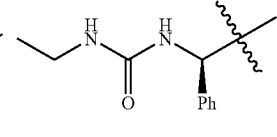 |
| 258 | 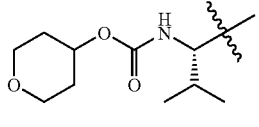 | 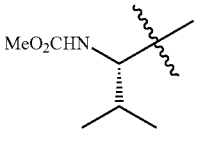 | 259 | 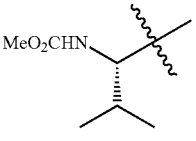 | 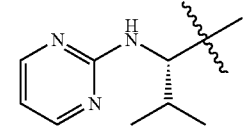 |
| 260 | 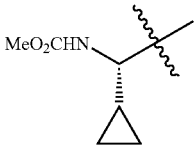 | 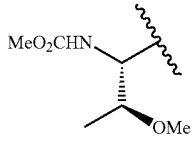 | 261 | 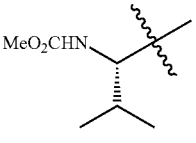 | 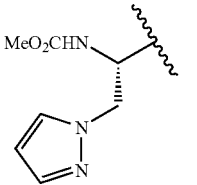 |

TABLE 4-continued

Compounds 244-263

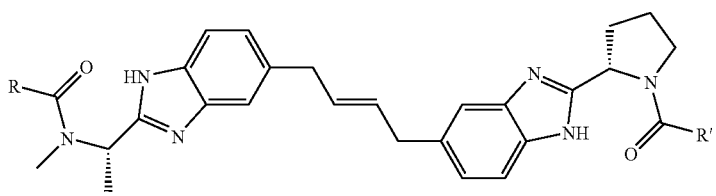

| Entry | R | R' | Entry | R | R' |
|---|---|---|---|---|---|
| 262 | MeO₂CHN- (isopropyl) | MeO₂CHN- (cyclopentyl) | 263 | MeO₂CHN- (with OMe) | pyridin-3-yl-NH- (isopropyl) |

TABLE 5

Compounds 264-283

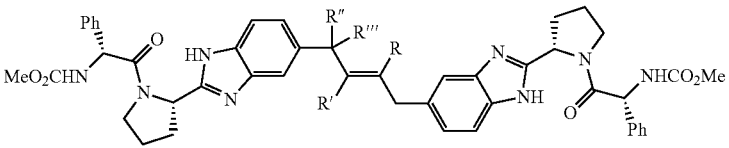

| Entry | R | R' | R'' | R''' | Entry | R | R' | R'' | R''' |
|---|---|---|---|---|---|---|---|---|---|
| 264 | F | H | H | H | 265 | F | H | F | H |
| 266 | F | F | H | H | 267 | Me | H | H | H |
| 268 | Me | Me | H | H | 269 | Me | H | Me | H |
| 270 | CF₃ | H | H | H | 271 | CF₃ | H | CF₃ | H |
| 272 | CF₃ | CF₃ | H | H | 273 | CO₂Me | H | H | H |
| 274 | CONH₂ | H | H | H | 275 | CO₂H | H | H | H |
| 276 | CH₂OH | H | H | H | 277 | CH₂NMe₂ | H | H | H |
| 278 | NMe₂ | H | H | H | 279 | OMe | H | H | H |
| 280 | OCF₃ | H | H | H | 281 | NHCO₂Me | H | H | H |
| 282 | Cl | H | H | H | 283 | Cl | H | Cl | H |

TABLE 6

Compounds 284-309

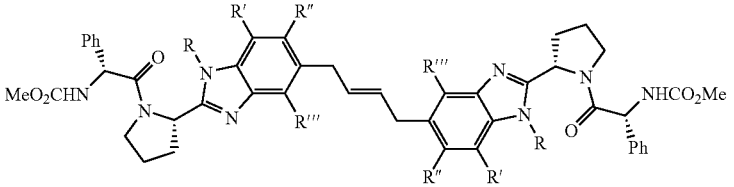

| Entry | R | R' | R'' | R''' | Entry | R | R' | R'' | R''' |
|---|---|---|---|---|---|---|---|---|---|
| 284 | Me | H | H | H | 285 | H | CO₂H | H | H |
| 286 | H | F | H | H | 287 | H | H | CO₂H | H |
| 288 | H | H | F | H | 289 | H | H | H | CO₂H |
| 290 | H | H | H | F | 291 | H | CO₂Me | H | H |
| 292 | H | Cl | H | H | 293 | H | H | CO₂Me | H |
| 294 | H | H | Cl | H | 295 | H | H | H | CO₂Me |
| 296 | H | H | H | Cl | 297 | H | CONH₂ | H | H |
| 298 | H | Me | H | H | 299 | H | H | CONH₂ | H |
| 300 | H | H | Me | H | 301 | H | H | H | CONH₂ |
| 302 | H | H | H | Me | 303 | H | OMe | H | H |
| 304 | H | CF₃ | H | H | 305 | H | H | OMe | H |
| 306 | H | H | CF₃ | H | 307 | H | H | H | OMe |
| 308 | H | H | H | CF₃ | 309 | CO₂Me | H | H | H |

TABLE 7
Compounds 310-352
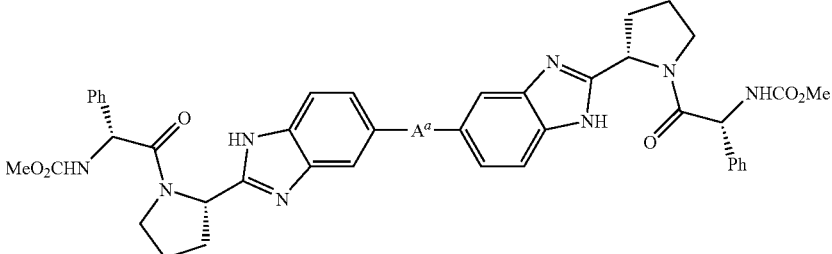
| Entry | $A^a$ | Entry | $A^a$ | Entry | $A^a$ |
|---|---|---|---|---|---|
| 310 | 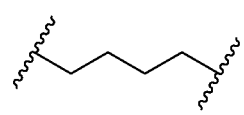 | 311 | 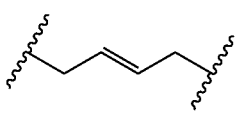 | 312 | 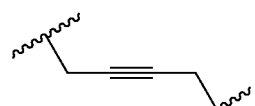 |
| 313 | 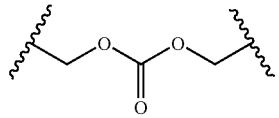 | 314 | 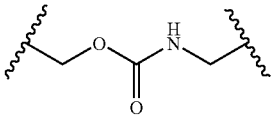 | 315 | 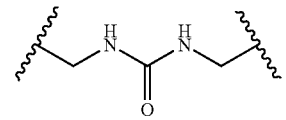 |
| 316 | 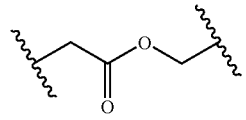 | 317 | 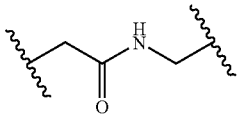 | 318 | 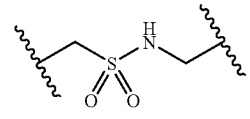 |
| 319 | 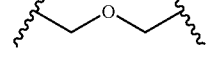 | 320 | 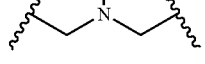 | 321 | 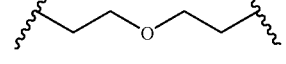 |
| 322 | 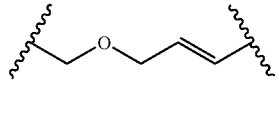 | 323 |  | 324 | 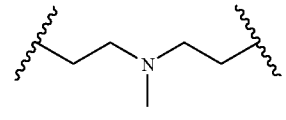 |
| 325 | 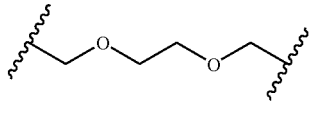 | 326 | 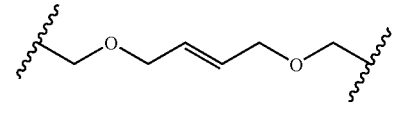 | 327 | 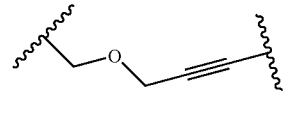 |
| 328 | 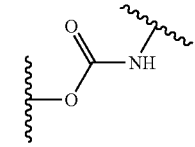 | 329 | 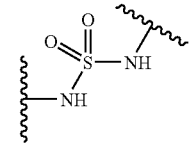 | 330 | 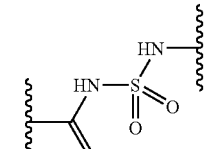 |
| 331 | 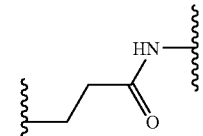 | 332 | 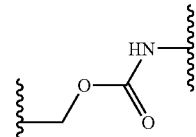 | 333 | 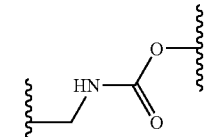 |

TABLE 7-continued
Compounds 310-352
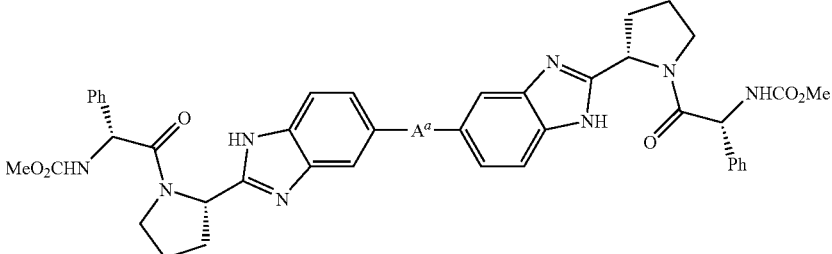
| Entry | A$^a$ | Entry | A$^a$ | Entry | A$^a$ |
|---|---|---|---|---|---|
| 334 | 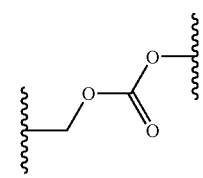 | 335 | 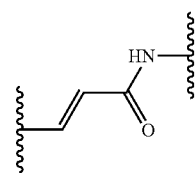 | 336 | 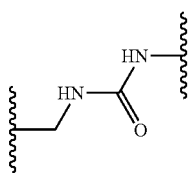 |
| 337 | 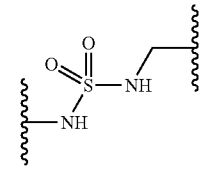 | 338 | 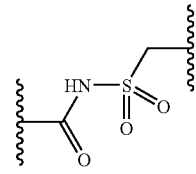 | 339 | 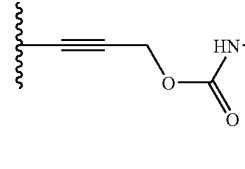 |
| 340 | 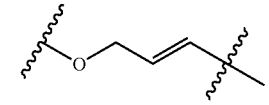 | 341 | 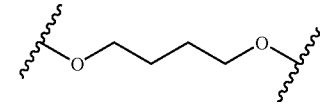 | 342 | 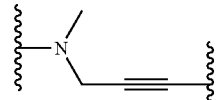 |
| 343 | 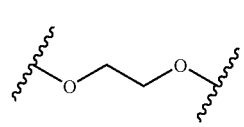 | 344 |  | 345 | 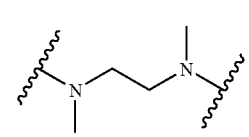 |
| 346 | 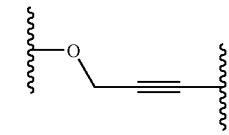 | 347 | 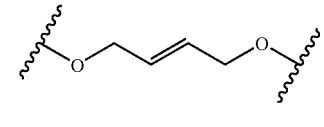 | 348 | 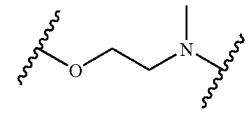 |
| 349 | 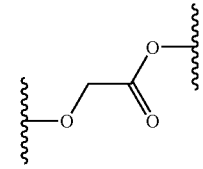 | 350 | 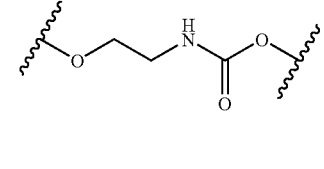 | 351 | 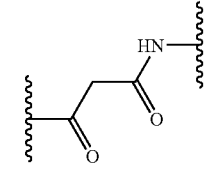 |
| 352 | 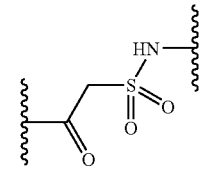 | | | | |

TABLE 8
Compounds 1a, 3a, and 353-357
1a 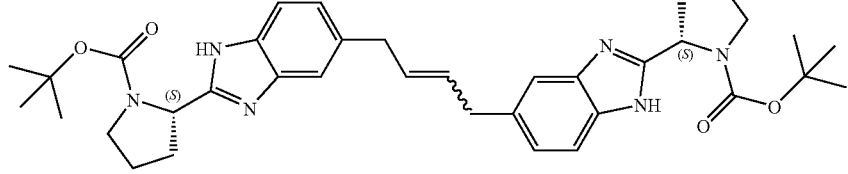
3a 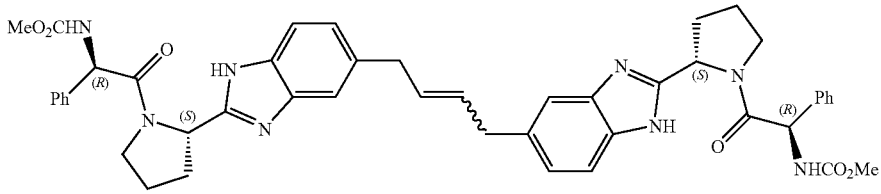
353 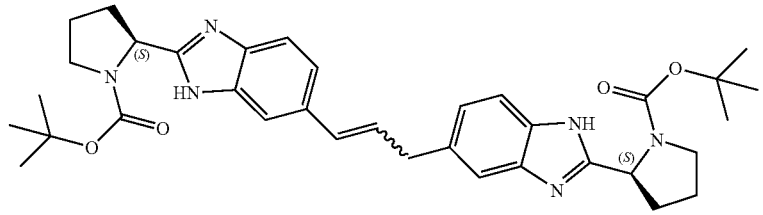
354 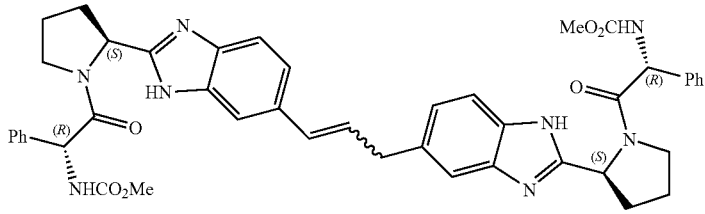
355 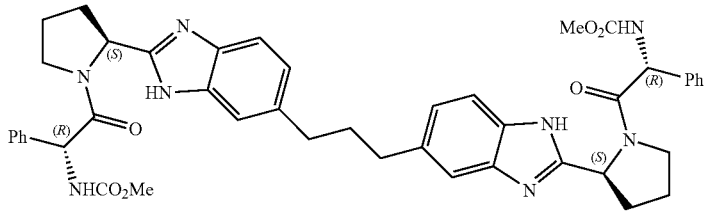
356 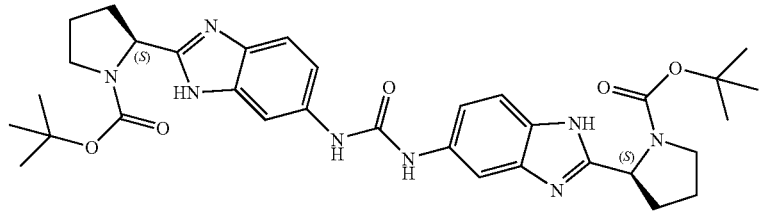
357 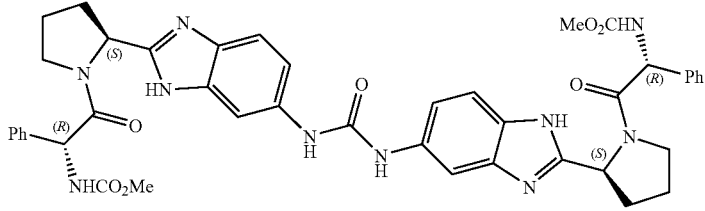

It will be appreciated that the description of the present invention herein should be construed in congruity with the laws and principals of chemical bonding. In some instances it may be necessary to remove a hydrogen atom in order to accommodate a substitutent at any given location.

It is intended that the definition of any substituent or variable (e.g., $R^1$, $R^2$, u, m, etc.) at a particular location in a molecule be independent of its definitions elsewhere in that molecule. For example, when u is 2, each of the two $R^1$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but not limited to, host immune modulators (for example, interferon-alpha, pegylated interferon-alpha, consensus interferon, interferon-beta, interferon-gamma, CpG oligonucleotides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; antisense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenofovir, or any combination thereof. A non-limiting example of the RNA-containing virus is hepatitis C virus (HCV).

Another further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20)

or T-1249, or any combination thereof. A non-limiting example of the RNA-containing virus is hepatitis C virus (HCV).

It can occur that a patient may be co-infected with hepatitis C virus and one or more other viruses, including but not limited to human immunodeficiency virus (HIV), hepatitis A virus (HAV) or hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant. Preferably said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to increase the bioavailability of a compound of the invention when the bioavailability is increased in comparison to the bioavailability in the absence of the CYP inhibitor.

In one embodiment, the invention provides methods for improving the pharmacokinetics of a compound of the invention. The advantages of improving the pharmacokinetics of drugs are recognized in the art (see, for example, US Patent App. Nos. 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combinations of the invention by means of a single patient pack, or patient packs of each formulation, containing within a package insert instructing the patient to the correct use of the invention is a desirable additional feature of this invention.

According to a further aspect of the invention is a pack comprising at least a compound of the invention and a CYP inhibitor and an information insert containing directions on the use of the combination of the invention. In an alternative embodiment of this invention, the pack further comprises one or more additional agents as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulations of each pharmaceutical component; a container housing the pharmaceutical formulation (s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e.g. a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tent-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo[2.2.1]heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups.

The term "heteroarylalkyl", as used herein, refers to a heteroaryl-substituted alkyl group. More preferred heteroarylalkyl groups are heteroaryl-$C_1$-$C_6$-alkyl groups. It is understood that any alkyl, alkenyl, alkynyl, cycloalkyl and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched or cyclic and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when a linear aliphatic group is said to "contain" or "include" or "comprise" one or more specified functional groups, the linear aliphatic group can be selected from one or more of the specified functional groups or a combination thereof, or a group wherein one or more carbons of a non-aromatic hydrocarbon (optionally substituted) is replaced by a specified functional group. In some examples, the linear aliphatic group can be represented by the formula M-Y-M', where M and M' are each independently absent or an alkyl, alkenyl or alkynyl, each optionally substituted, and Y is a functional group. In some examples, Y is selected from the group consisting of C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ or $C(O)N(R^{11})S(O)_2N(R^{11})$; wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

It is understood that any alkyl, alkenyl, alkynyl, alicyclic, cycloalkyl, cycloalkenyl, aryl, heteroaryl, heterocyclic, aliphatic moiety or the like, described herein can also be a divalent group when used as a linkage to connect two groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$—aryl, CO$_2$-heteroaryl, CO$_2$-heterocycloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocycloalkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthio-methyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitro-benzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxy-carbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

A compound of the present invention can also be administered in combination or alternation with antiviral agent. Exemplary antiviral agents include ribavarin, interferon, interleukin or a stabilized prodrug of any of them. More broadly described, the compound can be administered in combination or alternation with any of the anti-HCV drugs listed in Table 9 below.

TABLE 9

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |

TABLE 9-continued

Table of anti-Hepatitis C Compounds in Current Clinical Development

| Drug name | Drug category | Pharmaceutical Company |
|---|---|---|
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merch |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase Inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX-5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-antimiR ™-122) | microRNA | Santaris Pharma |

TABLE 9-continued

Table of anti-Hepatitis C Compounds in Current Clinical Development

| Drug name | Drug category | Pharmaceutical Company |
|---|---|---|
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

ABBREVIATIONS

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenylyl)ethyl carbonyl; BtOH for 1-hydroxy-benzotriazole; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phos-phonium Hexafluorophosphate; Brine for sodium chloride solution in water; Cbz for carbobenzyloxy; CDI for carbonyldiimidazole; $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or (i-Pr)$_2$EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylamino-propyl)-N'-ethylcarbodiimide; EDC HCl for N-(3-dimethylamino-propyl)-N'-ethylcarbodiimide hydrochloride; EtOAc for ethyl acetate; EtOH for ethanol; $Et_2O$ for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium Hexafluorophosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or —$SO_2$—$CH_3$; $Ms_2O$ for methanesulfonic anhydride or mesyl-anhydride; $NaBH_4$ for sodium borohydride; $NaBH_3CN$ for sodium cyanoborohydride; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMMO for N-methylmorpholine N-oxide; $NaHCO_4$ for sodium periodate; Ni for nickel; OH for hydroxyl; $OsO_4$ for osmium tetroxide; Pd for palladium; Ph for phenyl; PMB for p-methoxybenzyl; POPd for dihydrogen dichlorobis(di-tert-butylphosphinito-κP)palladate(II); $Pd_2(dba)_3$ for tris(dibenzylidene-acetone) dipalladium (0); $Pd(PPh_3)_4$ for tetrakis(triphenylphosphine)palladium (0); $PdCl_2(PPh_3)_2$ for trans-dichlorobis(triphenyl-phosphine)palladium (II); Pt for platinum; Rh for rhodium; rt for room temperature; Ru for ruthenium; SEM for (trimethylsilyl)ethoxymethyl; TBAF for tetrabutylammonium fluoride; TBS for tent-butyl dimethylsilyl; TEA or $Et_3N$ for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or $PPh_3$ for triphenyl-phosphine; Troc for 2,2,2-trichloroethyl carbonyl; Ts for tosyl or —$SO_2$—$C_6H_4$—$CH_3$; $Ts_2O$ for tolylsulfonic anhydride or tosyl-anhydride; TsOH for p-tolylsulfonic acid; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of benzimidazole related intermediates. A retro-synthesis of those title compounds include direct formation of a suitably linked dibenzimidazole core structure followed by attachment of a suitable $R^6$ group, plus some functional group manipulations in between and/or after.

The most straightforward method to synthesizing the compound of the present invention is illustrated in Schemes 1, in which s and t at each occurrence are each independently 0, 1, 2; the dotted line is absent or a single bond; and PG is an amino-protecting group such as Boc, Cbz, Troc, Teoc, or the like. The synthesis starts from the construction of an optionally substituted benzimidazole 1-2 or 1-3, which may be obtained by condensation of an amino acid or its derivative 1-1.1 or 1-1.2 and an o-phenylene-diamine 1-1 under the conditions to those skilled in the art. The benzimidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat. Optionally, the NH group in the newly formed benzimidazole may be protected using an amino protecting group, such as SEM (i.e. SEM-Cl, NaH), Boc, Cbz, Teoc, Troc, or the like.

The bromides 1-2 and 1-3 may be converted to vinylic 1-4 and 1-6, or allylic 1-5 and 1-7 using the Stille reaction conditions which are known to those skilled in the art (see reviews: A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European J.* 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), using a vinylstanne such as tributylvinylstanne 1-2.1 or an allylstanne such as allyltributylstanne 1-2.2. Alternatively, bromides 1-2 and 1-3 may be subjected to lithium-halogen exchange with various (n-, s-, or t-) butyl lithium and the resulting lithiate can be trapped with a nucleophile, i.e. a halide, such as various allyl halide to give the allylated 1-5 and 1-7.

The intermediates 1-4 and 1-5 can be crossed-linked with intermediates 1-6 and 1-7 using transition metal catalyzed Hoveyda-Grubbs metathesis reaction conditions which are known to those skilled in the art (see J. D. Waetzig, et al, *Chemtracts* 2006, 19, 157; C. L. Dwyer, *Metal-Catalysis in Industrial Organic Processes* 2006, 201; S. T. Diver, et al, *Chem. Review* 2004, 104, 1317; A. J. Vernall, et al, *Aldrichimica Acta* 2003, 36, 93; S. T. Connon, et al, *Angew. Chem. Int. Ed.* 2003, 42, 1900; S. E. Gibson, et al, *Topics in Organometallic Chemistry* 1998, 1(Alkene Metathesis in Organic Synthesis), 155; Y. Schrodi, et al, *Aldrichimica Acta* 2007, 40, 45), giving the corresponding olefin 1-8, a core structure of a linked dibenzimidazole. Alternatively and additionally, intermediates 1-4 and 1-5 may be coupled with bromide 1-3 under the well-known Heck reaction conditions (reviewed by M. Arisawa, *Chem. Pharm. Bull.* 2007, 55, 1099; P. Guiry, et al, *Current Org. Chem.* 2004, 8, 781; J. T. Link, *Org. React.* 2002, 60, 167; S. Braese, et al, *Metal-Catalyzed Cross-Coupling Reactions* 1998, 99) to give olefin 1-9, another core structure of a linked dibenzimidazole.

The structural cores 1-8 and 1-9 then may serve as common intermediates for further derivatizations to the title compounds I-1 of the present invention. Optionally, the intermediate 1-9, for example, can be converted to 1-10 in two steps: 1) mono-deprotection of the linear or cyclic amine moiety may be accomplished, for example, treatment under hydrolytic conditions in the presence of an acid to remove Boc; treatment to hydrogenolytic conditions under Pd catalyst to remove the Cbz protection group; or treatment with TBAF to remove Teoc; or treatment with zinc to remove Troc; depending on the nature of PG group; and 2) the released amine functionality may be acylated with an carboxylic acid under standard acylation conditions, for example a coupling reagent such as HATU in combination with an organic base such as DIPEA can be used in this regard; alternatively, the released amine may be reacted with an isocyanate, carbamoyl chloride or chloroformate to provide an urea or carbamate. Various carboxylic acids including amino acids in racemic or optical form are commercially available, and/or can be synthesized in racemic or optical form, see references cited in reviews by D. Seebach, et al, *Synthesis* 2009, 1; C. Cativiela and M. D. Diaz-de-Villegas, *Tetrahedron: Asymmetry* 2007, 18, 569; 2000, 11, 645; and 1998, 9, 3517; and experimental examples compiled in patent application WO 2008/021927A2 by C. Bachand, et al, from BMS, which is incorporated herein by reference. 1-10 may be further deprotected under hydrolytic conditions in the presence of an acid such as TFA or hydrogen chloride to remove the Boc protection group and the released amine functionality can be further derivatized to the title compounds I-1 using the conditions described above. Optionally and additionally the double bond in the unsaturated title compounds can be saturated under hydrogenolytic conditions with a Pd catalyst. Additionally it is noteworthy that the SEM-group can be removed at the same time when deprotecting the Boc-protection in acid as described above; also the double bond in the intermediates 1-8 and 1-9 can be saturated under hydrogenolytic conditions with a Pd catalyst to remove Cbz.

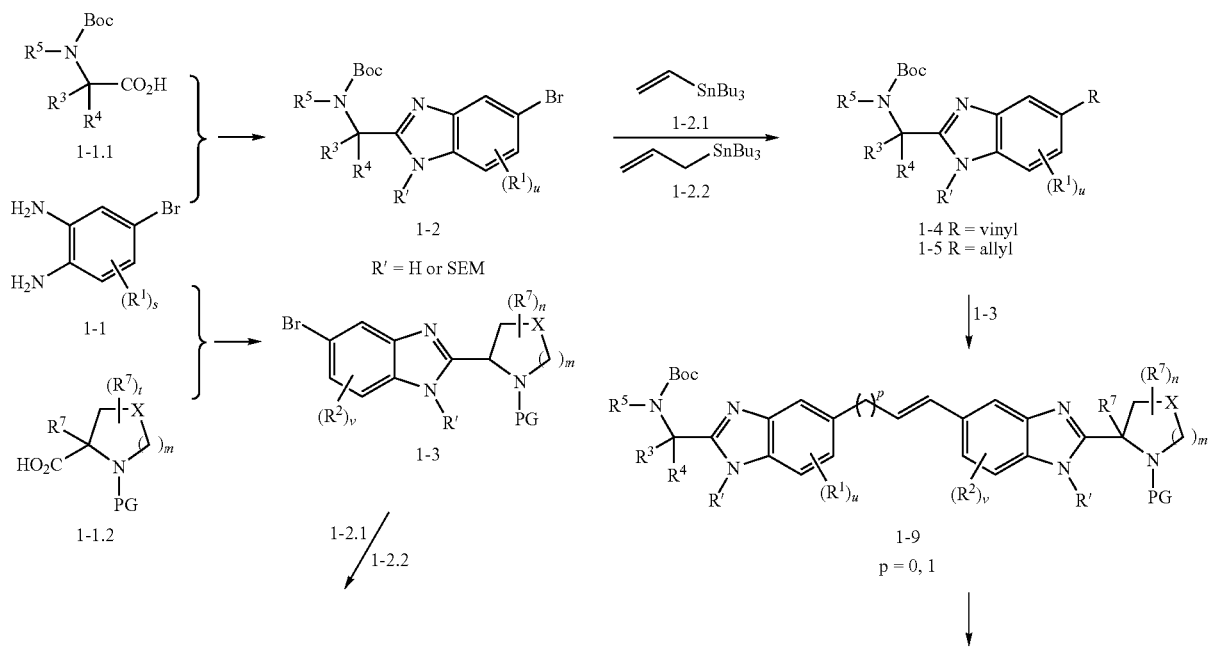

Scheme 1

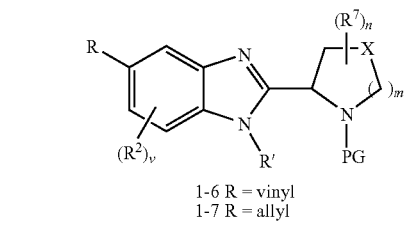

1-6 R = vinyl
1-7 R = allyl

↓ 1-4 or 1-5

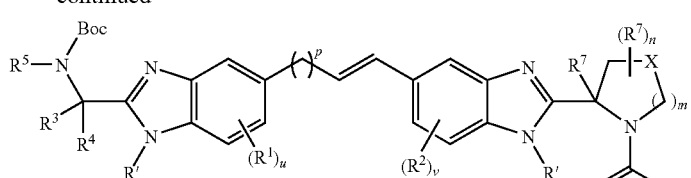

1-10

↓

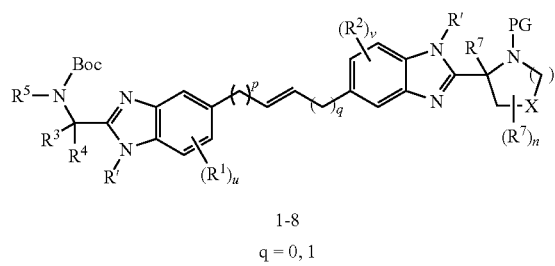

1-8
q = 0, 1

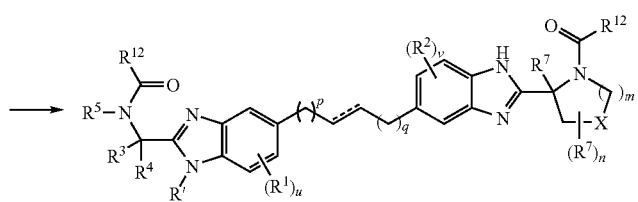

I-1

Some of the structural cores of the title compounds of the present invention, for example some of those listed in the embodiments, may be synthesized directly utilizing various cross-coupling strategies, such as Sonogashira coupling, Buchwald amidation (see C. C. Mauger, et al, *Aldrichimica Acta* 2006, 39, 17; S. L. Buchwald, et al, *JACS* 2009, 131, 78; *Accounts Chem. Res.* 2008, 41, 1439; H. C. Ma, et al, *Synlett* 2008, 1335; J. H. M. Lange, *Tetrahedron Lett.* 43, 1101; S. L. Buchwald, et al, *JACS* 2002, 124, 7421), amide or ester bond formation, Buchwald etherification, Buchwald amination, William etherification, alkylation etc, which are known to those skilled in the arts, between various benzimidazole related intermediates. A general synthesis and further elaboration of these benzimidazole related intermediates are summarized in Scheme 2. It should be understood that the NH on the benzimidazole ring may be optionally protected as described above.

As illustrated in Scheme 1, vinyl benzimidazole 2-2 can be synthesized under Stille coupling condition, which may be further elaborated to aldehyde 2-6 through ozonolysis cleavage or to alcohol 2-9 by hydroboration-oxidation sequence. 2-9 may be converted to the bromide 2-14 by the well-known bromination procedure, which may be further functionalized to amine 2-18 through azide substitution followed by reduction. The aldehyde 2-6 can then either be reduced to the alcohol 2-8, or be converted to the α,β-unsatuated acid intermediate 2-7 through Horner-Wadsworth-Emmons aldehyde homologation reaction followed by saponification. Alcohol 2-8 may be similarly converted to the corresponding amine 2-11 and bromide 2-13. Bromide 2-13 may be homologated to alkyne intermediate 2-17 with a metal acetylide. In addition, bromide 2-13 may be also transformed to thiol 2-10 through nucleophilic substitution, which can be further oxidized to sulfonic acid 2-15. Sulfonamide 2-16 could then be derived from 2-15 through sulfonyl chloride activation.

Similarly, the allyl benzimidazole 2-3 can be converted to the aldehyde 2-21 by ozonolysis, which can be oxidized to acid 2-22. Alcohol 2-23 can likewisely be derived from allyl 2-3 through hydroboration-oxidation sequence, which may be further oxidized to the corresponding carboxylic acid 2-24.

In addition to vinyl and allyl intermediates 2-2 and 2-3, benzimidazole bromide 2-1 may be transformed to propargyl alcohol 2-5 though Sonogashira coupling with propargyl alcohol. Propargyl bromide 2-19 can then be generated through simple bromination. Also, benzimidazole bromide 2-1 may be converted to the methyl ketone 2-4 by coupling with tributyl(1-ethoxyvinyl)tin under Stille coupling condition. Methyl ketone 2-4 can be then deprotonated by NaH or KOt-Bu to generate the carbon anion which can nucleophilically attack dimethyl carbonate to produce β-keto ester 2-20.

The core structures to generate the compounds of the present invention may also be derived from nitrobenzimidazole 2-25, which can be prepared from the corresponding 4-nitro-1,2-diaminobenzene using the procedures described in Scheme 1. As shown in Scheme 2, 2-25 can be converted to amine 2-26 through $NO_2$-reduction (i.e. $H_2$, catalytical Pd). Diazotization of amine 2-26 with a nitrite such as sodium nitrite, isobutyl nitrite, or the like, in an aqueous acid such as acetic acid, hydrochloric acid, sulfuric acid, or the like, optionally in the presence of a copper or copper salt, may afford hydroxy intermediate 2-27. Similarly, benzimidazole-carboxylate 2-28, which can be prepared from the corresponding 4-methyl-1,2-diaminobenzoate using the procedures described in Scheme 1, can be hydrolyzed to the corresponding carboxylic acid 2-29.

With all these benzimidazole related intermediates in hand, various title compounds could be formed from various coupling or alkylation strategies.

Scheme 2
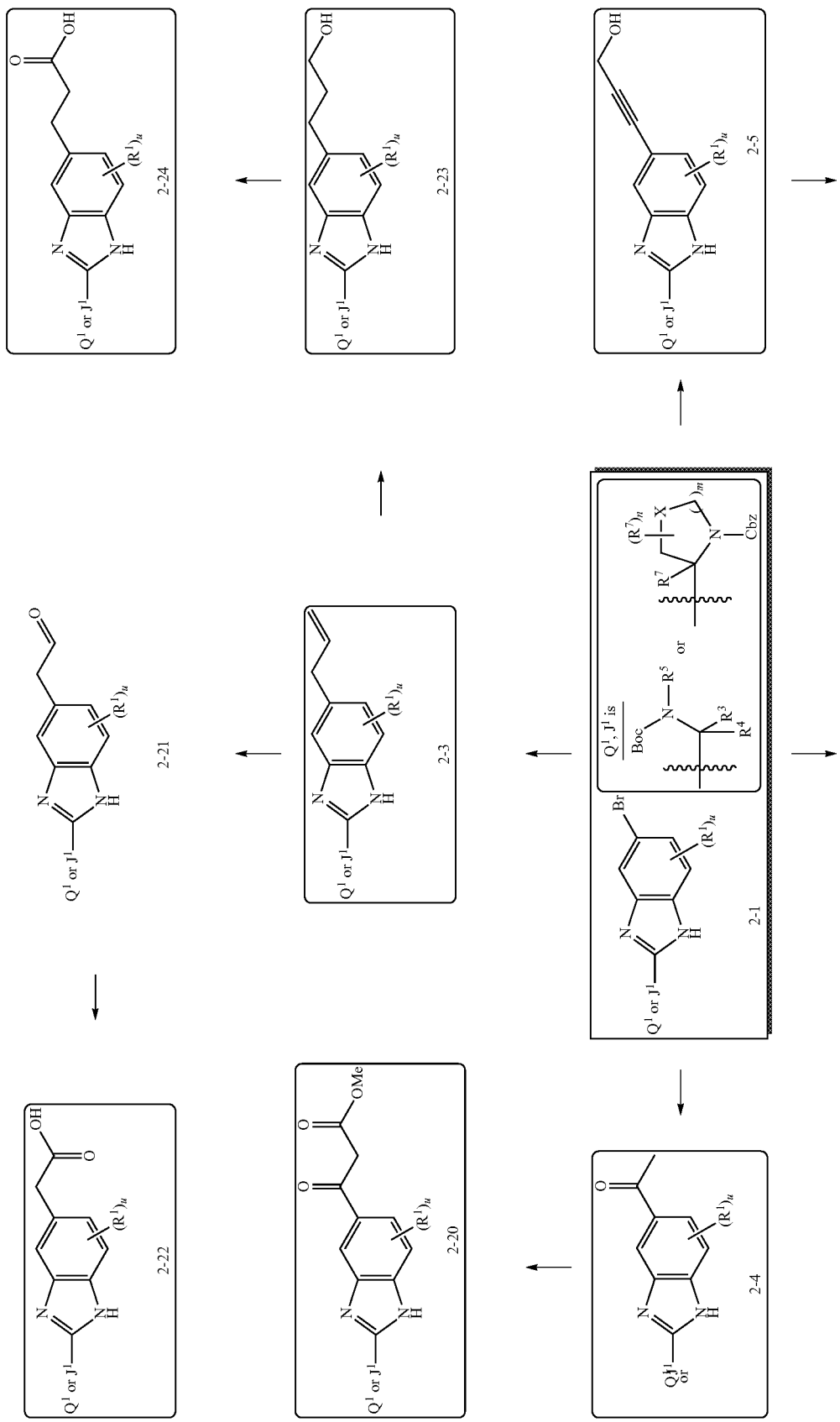

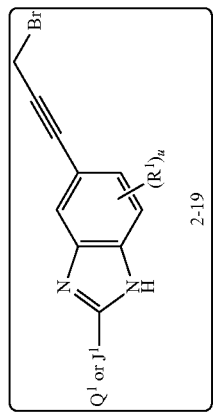
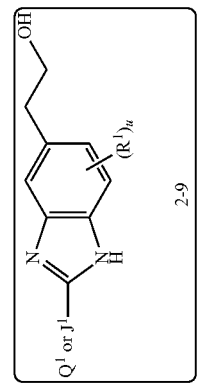
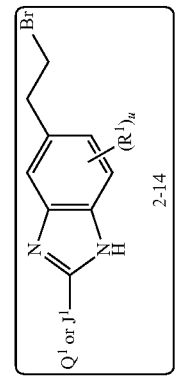
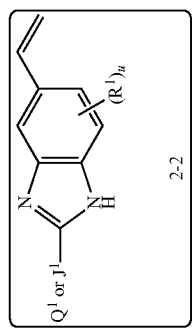
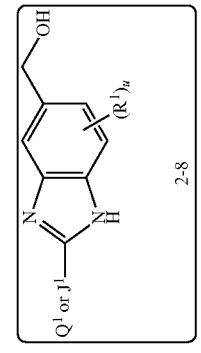
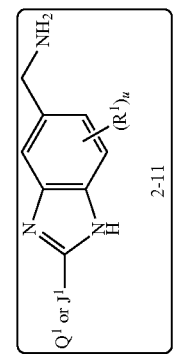
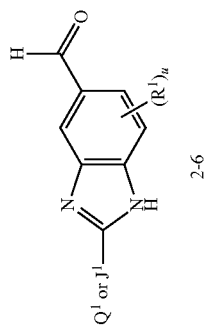
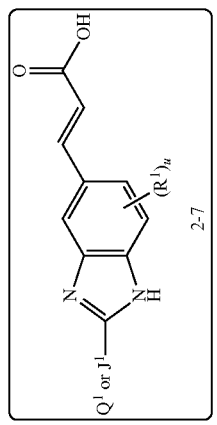
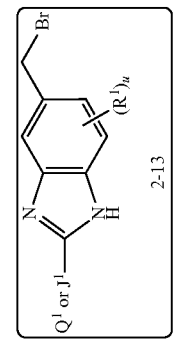
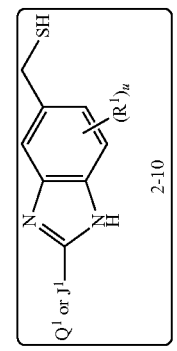

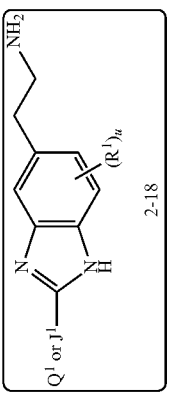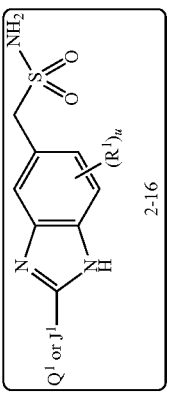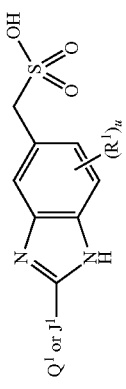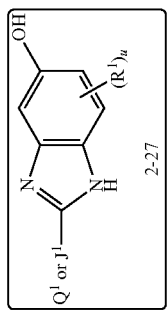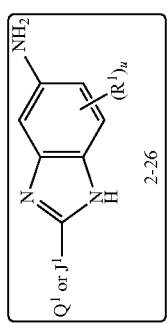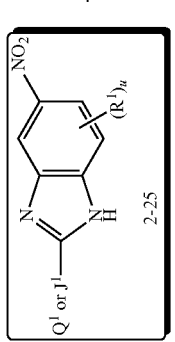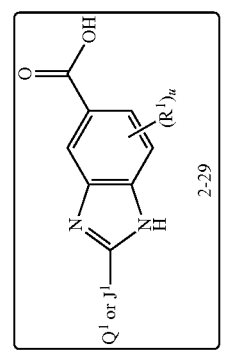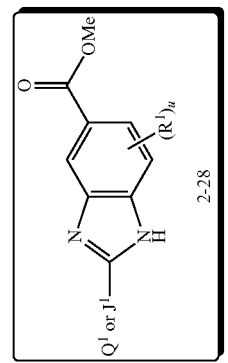

Alternatively as shown in Scheme 3, the compounds of the present invention (for example I-a) may also be derived from bromobenzimidazoles 1-2a and 1-3a using the procedures described previously. The intermediates 1-2a and 1-3a have the desired acyl groups already installed as seen in amino acid derivatives 1-1.1a and 1-1.2a, which can be prepared from protected amino acids 3-1.1 and 3-1.2.

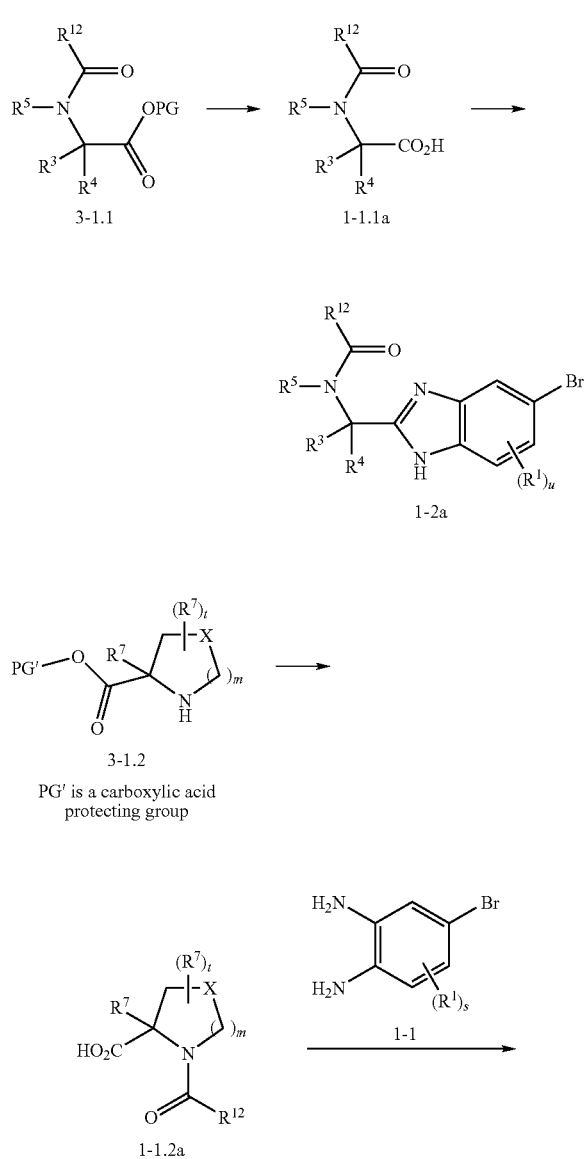

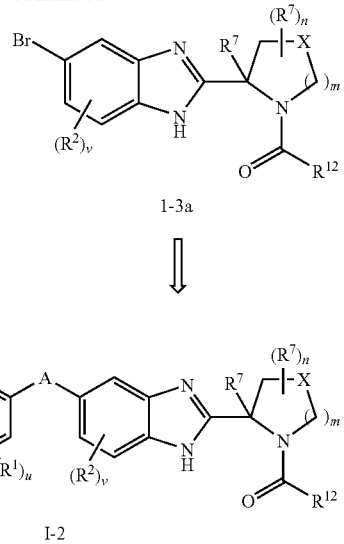

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1a

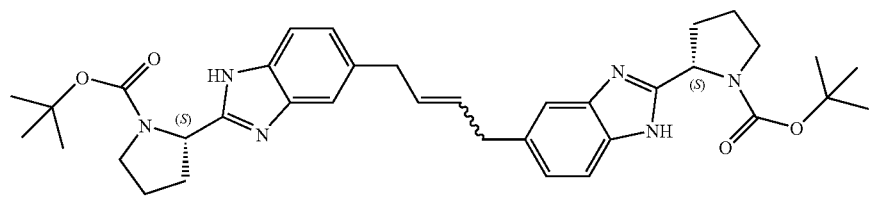

Step 1a-a. A mixture of N-Boc-L-proline (5.754 g, 26.7 mmol) and TEA (3.73 mL, 26.7 mmol) in THF (60 mL) at −20° C. was treated with ethyl chloroformate (2.55 mL, 26.7 mmol) for 30 minutes before a slow addition of 4-bromo-1,2-diaminobenzene (5.00 g, 26.7 mmol) in THF (20 mL). It was then kept at −20° C. for 1 hour and then slowly warmed up to rt and stirred at rt overnight. The volatiles were evaporated and the residue was partitioned (EtOAc—water). The organics were washed with brine, dried ($Na_2SO_4$), filtered and evaporated to give the crude desired compound as a dark brown foam (10.7 g). ESIMS m/z=384.18, 386.18 [M+H]$^+$.

Step 1a-b. A solution of the crude compound of step 1a-a (10.7 g, theo. 26.7 mmol) in glacial acetic acid (100 mL) was heated at 50° C. for 2 hours. The volatiles were evaporated off and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the desired compound as a brown foam (5.78 g, 59%). ESIMS m/z=366.17, 368.17 [M+H]$^+$. $^1$H NMR ($CDCl_3$) 10.96, 10.93 (2 s, 1H), 7.81, 7.30 (2 s, 1H), 7.53, 7.17 (2d, J=8.5 Hz, 1H), 7.23, 7.03 (2d, J=8.5 Hz, 1H), 5.09, 5.07 (2s, 1H), 3.42-3.49 (m, 2H), 2.75-2.85 (m, 1H), 2.13-2.23 (m, 2H), 1.97-2.00 (m, 1H), 1.48 (s, 9H).

Step 1a-c. A mixture of the compound of step 1a-b (0.250 g, 0.683 mmol), allyltributylstannane (0.26 mL, 0.820 mmol) and $Pd(PPh_3)_4$ (39.4 mg, 34.1 μmol) in toluene (6 mL) was degassed and heated to 110° C. under $N_2$ overnight. The volatiles were evaporated and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the desired compounds as a colorless oil (0.127 g, 60%). ESIMS m/z=328.23 [M+H]$^+$.

Step 1a-d. A mixture of the compound of step 1a-c (0.100 g, 0.306 mmol) and Grubbs-1 Catalyst (12.5 mg, 15.2 μmol) in $CH_2Cl_2$ (6 mL) was degassed and heated to reflux under $N_2$ for 3 days. The volatiles were evaporated and the residue was purified by flash column chromatography (silica, hexanes-ethyl acetate) to give the title compound as a colorless oil (8.7 mg). ESIMS m/z=627.28 [M+H]$^+$.

Example 3a

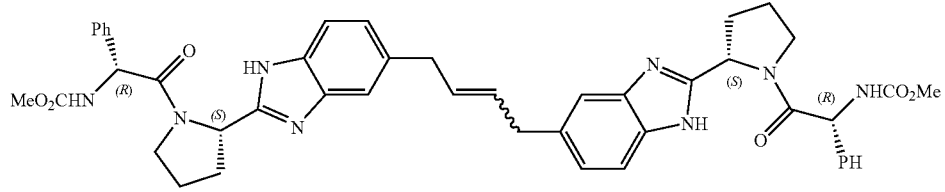

Step 3a-a. A solution of the compound of Example 1a-a (8.7 mg, 13.8 μmol) in 1,4-dioxane (1 mL) was treated with HCl in 1,4-dioxane (4 M, 4 mL) rt for 30 min. The volatiles were evaporated off to give the crude desired compound as a yellow solid which was directly used in the next step. ESIMS m/z=427.39 [M+H]$^+$.

Step 3a-b. A mixture of the crude compound of step 3a-a (13.8 μmol at most) and (R)-(methoxycarbonyl)amino phenyl acetic acid (prepared according to WO 2008/021927, 7.2 mg, 34.5 μmol) in DMF (3 mL) was treated with HATU (12.0 mg, 31.7 μmol) in the presence of DIPEA (34.4 μL, 0.276 mmol) for 2 hours at rt and the volatiles were evaporated off to provide a brown sirup. It was purified by flash column chromatography (silica, $CH_2Cl_2$-MeOH) to give the title compound as a very light yellow solid (8.8 mg, 2 steps 79%). ESIMS m/z=809.30 [M+H]$^+$.

Example 310

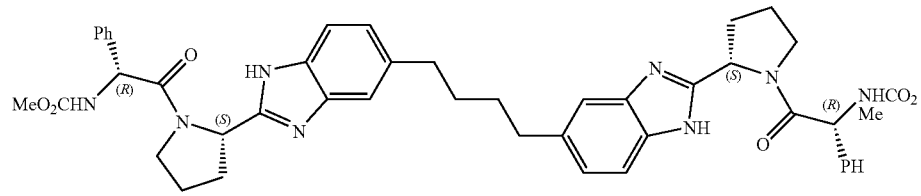

A mixture of the compound of example 3a (5.8 mg, 7.1 μmol) and $Pd(OH)_2$ on carbon (20%, 15.0 mg) in ethanol (3 mL) was treated with $H_2$ balloon overnight. It was filtered through celite and the filtrate was concentrated. The residue was purified by flash column chromatography (silica, $CH_2Cl_2$-MeOH) to give the title compound as a white solid (5.0 mg, 86%). ESIMS m/z=811.34 [M+H]$^+$.

Example 353

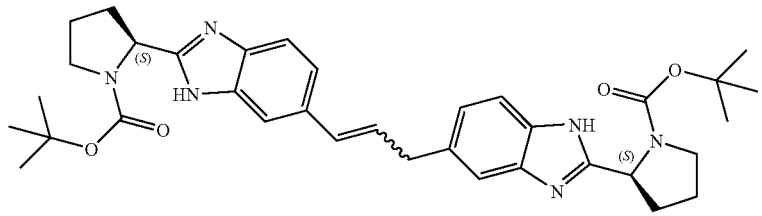

A mixture of the compound of step 1a-b (0.156 g, 0.427 mmol), the compound of step 1a-c (0.127 g, 0.388 mmol), triethylamine (0.56 mL, 3.88 mmol), tri-o-tolylphosphine (15.2 mg, 48.5 μmol) and Pd(OAc)$_2$ (4.4 mg, 19.4 μmol) in CH$_3$CN (6 mL) was degassed and heated to 80° C. under N$_2$ overnight. The volatiles were evaporated and the residue was partitioned (EtOAc—saturated aqueous NaHCO$_3$). The organics were washed with brine, dried (Na$_2$SO$_4$), filtered and evaporated. The residue was purified by flash column chromatography (silica, hexanes-ethyl acetate) to give the title compound as a light yellow oil (0.165 g, 70%). ESIMS m/z=613.47 [M+H]$^+$.

Example 354

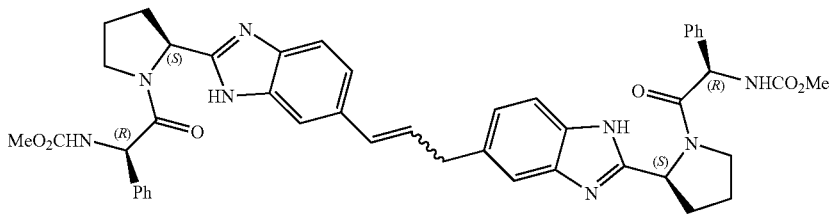

The title compound was synthesized from the compound from Example 353 using procedures similar to that described in Example 3a. ESIMS m/z=795.56 [M+H]$^+$.

Example 355

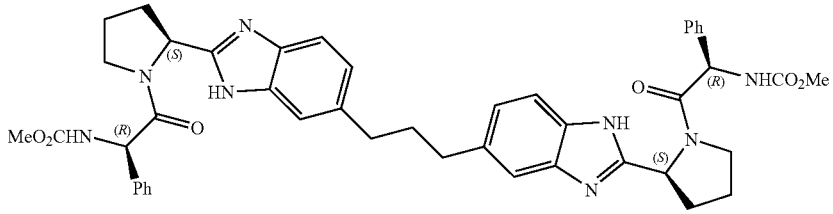

The title compound was synthesized from the compound from Example 354 using procedures similar to that described in Example 310. ESIMS m/z=797.69 [M+H]$^+$.

Example 356

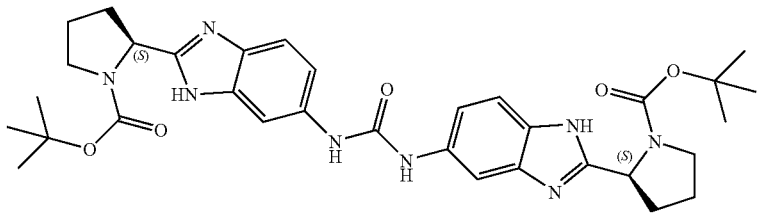

Step 356a. A mixture of N-Boc-L-proline (7.03 g, 32.6 mmol) and TEA (4.55 mL, 32.6 mmol) in THF (60 mL) at −20° C. was treated with iso-butyl chloroformate (4.27 mL, 32.6 mmol) for 30 minutes before a slow addition of 4-nitro-1,2-diaminobenzene (5.00 g, 32.6 mmol) in THF (20 mL). It was then kept at −20° C. for 1 hour and then slowly warmed up to rt and stirred at rt overnight. The volatiles were evaporated and the residue was partitioned (EtOAc—water). The organics were washed with brine, dried (Na$_2$SO$_4$), filtered and evaporated to give the crude desired compound as a dark brown foam which was directly used in the next step. ESIMS m/z=351.23 [M+H]$^+$.

Step 356b. A mixture of the compound from step 356a (32.6 mmol at most) and Pd on carbon (10%, 500 mg) in ethanol (200 mL) was treated with H$_2$ balloon overnight. The mixture was filtered through celite and the filtrate was concentrated to give the crude desired compound as a dark purple foam which was directly used in the next step. ESIMS m/z=321.25 [M+H]$^+$.

Step 356c. A solution of the crude compound from step 356b (32.6 mmol at most) in glacial acetic acid (60 mL) was heated at 40° C. for 3 hours. The volatiles were evaporated off and the residue was partitioned (EtOAc—saturated aqueous NaHCO$_3$). The organics were washed with brine, dried (Na$_2$SO$_4$), filtered and evaporated. The residue was purified by flash column chromatography (silica, CH$_2$Cl$_2$-MeOH) to give the desired compound as a purple foam (7.02 g, 3 steps 71%). ESIMS m/z=303.28 [M+H]$^+$.

Step 356d. A mixture of the compound from step 356c (0.200 g, 0.662 mmol), CDI (53.7 mg, 0.331 mmol) and triethylamine (0.11 mL, 0.794 mmol) in THF (5 mL) was kept stirring under N$_2$ overnight. The volatiles were evaporated and the residue was purified by flash column chromatography (silica, CH$_2$Cl$_2$-MeOH) to give the title compound as a light purple solid (0.115 g, 55%). ESIMS m/z=631.54 [M+H]$^+$.

Example 357

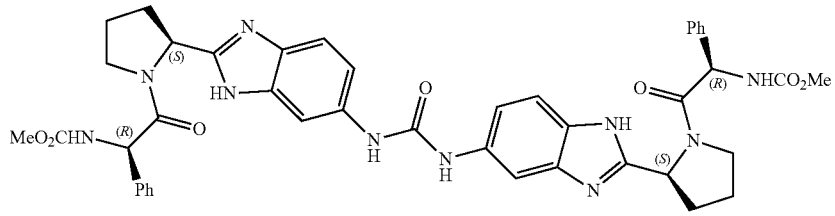

The title compound was synthesized from the compound from Example 356 using procedures similar to that described in Example 3a. ESIMS m/z=813.65 [M+H]$^+$.

The remaining compounds of examples 1-352 may be prepared using procedures similar to those described in examples 1a, 3a, 310, 353-357, and/or as described in the Synthetic Methods.

TABLE 1

Examples 1-219

TABLE 1-continued
Examples 1-219
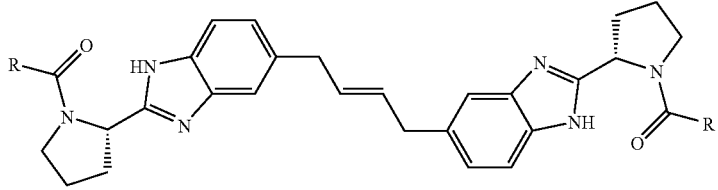
| Entry | R 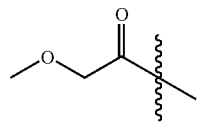 | Entry | R 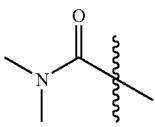 | Entry | 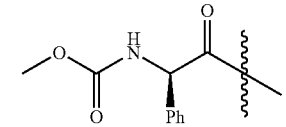 |
|---|---|---|---|---|---|
| 7 | 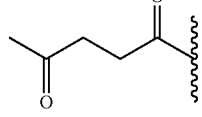 | 8 | 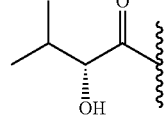 | 9 | 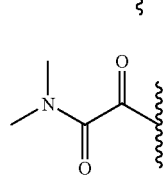 |
| 10 | 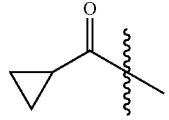 | 11 | 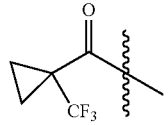 | 12 | 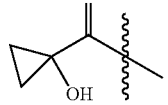 |
| 13 | 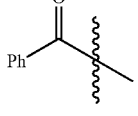 | 14 | 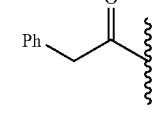 | 15 | 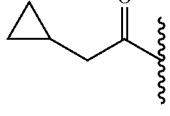 |
| 16 | 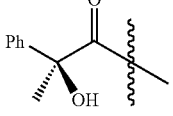 | 17 | 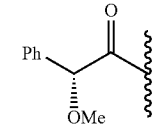 | 18 | 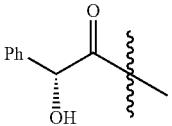 |
| 19 | 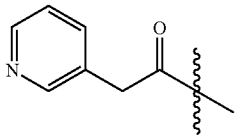 | 20 | 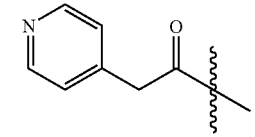 | 21 | 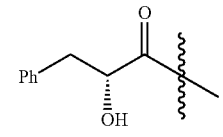 |
| 22 | 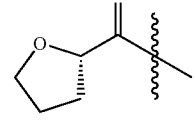 | 23 | 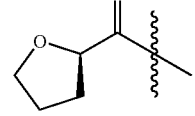 | 24 | 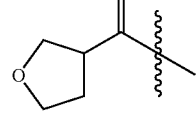 |
| 25 | 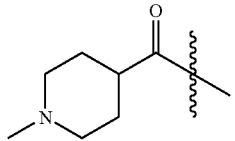 | 26 | 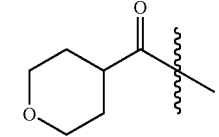 | 27 | 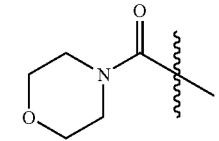 |
| 28 | | 29 | | 30 | |

TABLE 1-continued

Examples 1-219

TABLE 1-continued
Examples 1-219
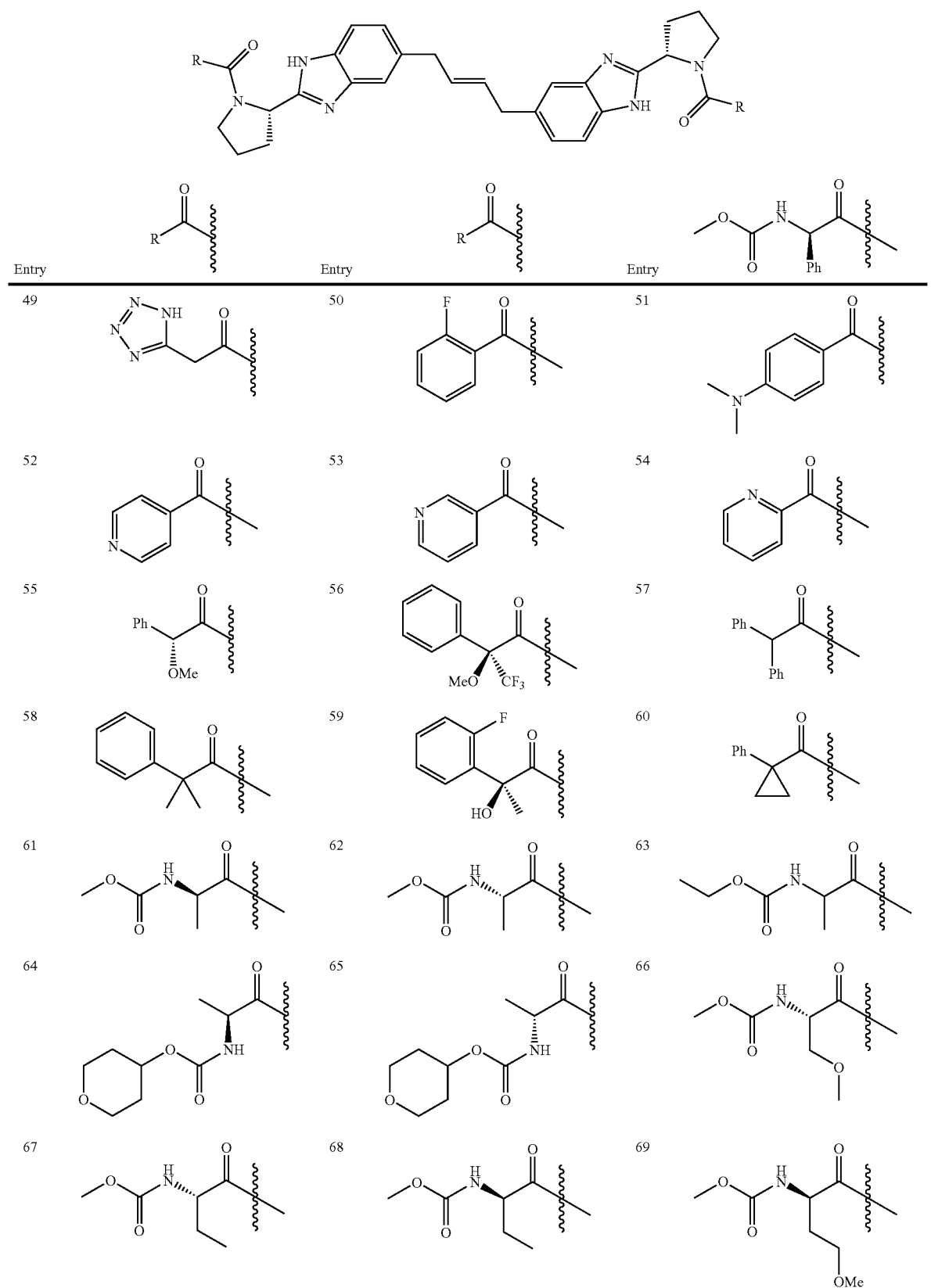

TABLE 1-continued

Examples 1-219

US 8,188,132 B2
97                                                                98
TABLE 1-continued
Examples 1-219
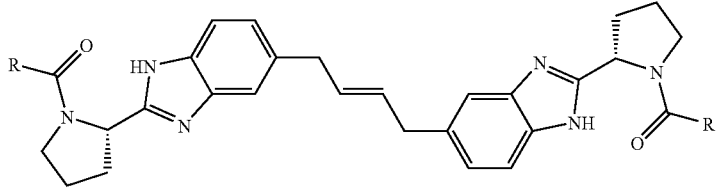
| Entry | 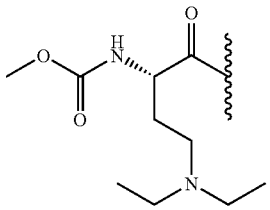 | Entry | 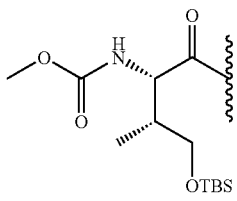 | Entry | 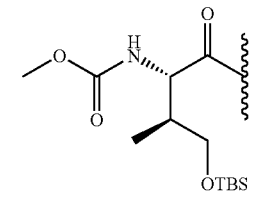 |
|---|---|---|---|---|---|
| 88 | 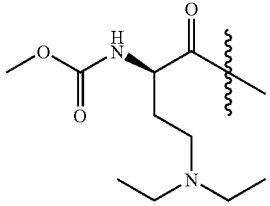 | 89 | 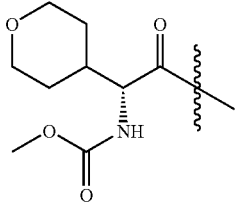 | 90 | 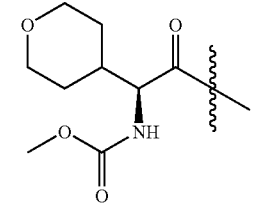 |
| 91 | 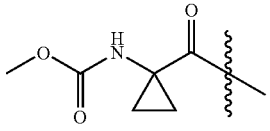 | 92 | 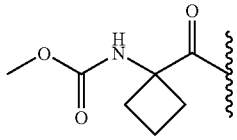 | 93 | 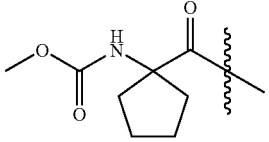 |
| 94 | 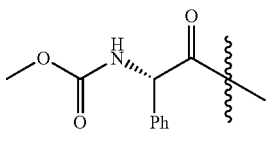 | 95 | 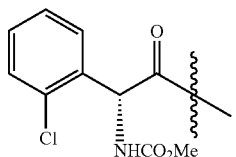 | 96 | 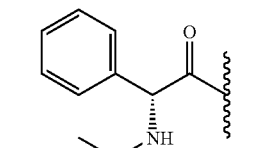 |
| 97 | 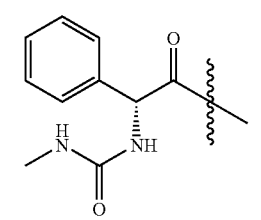 | 98 | 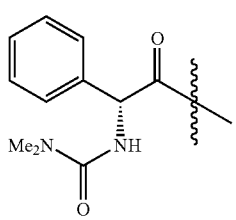 | 99 | 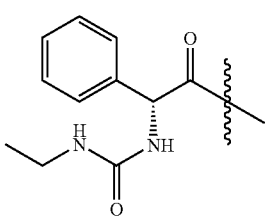 |
| 100 | 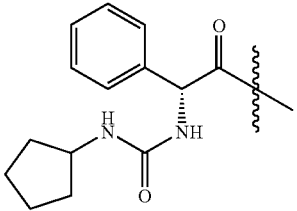 | 101 | 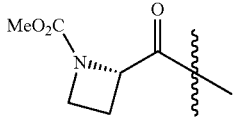 | 102 | 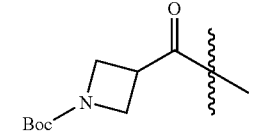 |
| 103 | | 104 | | 105 | |

TABLE 1-continued
Examples 1-219
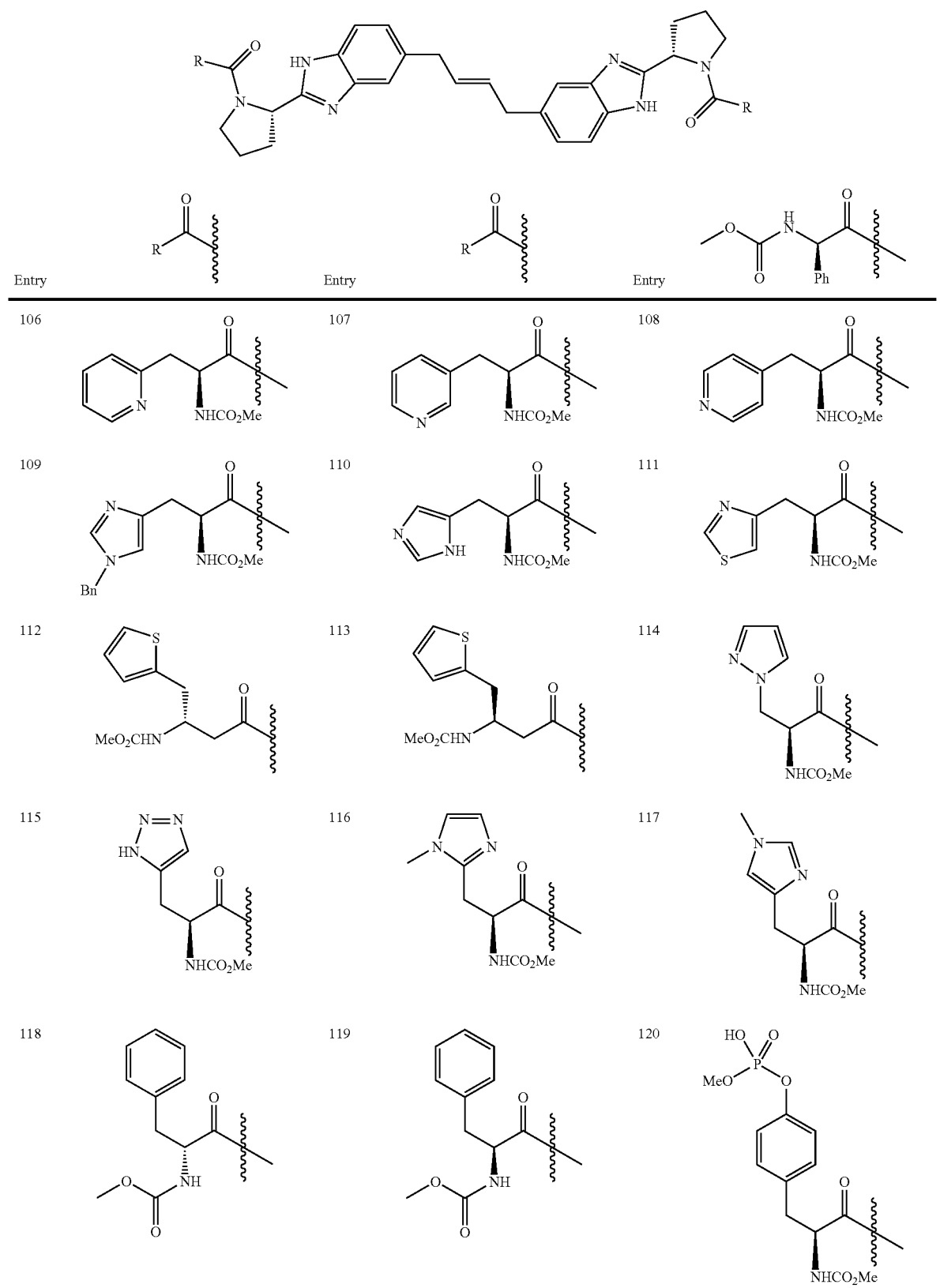

TABLE 1-continued

Examples 1-219

| Entry | | Entry | | Entry | |
|---|---|---|---|---|---|
| 121 | (indole CH2, NHCO2Me) | 122 | (4-OBn-benzyl, NHCO2Me) | 123 | (4-(FmocNHCH2)-benzyl, NHCO2Me) |
| 124 | (oxazolidinone) | 125 | (oxazolidinone) | 126 | (5-methyl oxazolidinone) |
| 127 | (MeO2CNH-cyclopentyl) | 128 | (MeO2CNH-cyclopentyl) | 129 | (MeO2CNH-cyclohexyl) |
| 130 | (MeO2CNH-cyclopentyl) | 131 | (MeO2CNH-cyclopentyl) | 132 | (MeO2CNH-cyclohexyl) |
| 133 | (benzyl, NHCO2Me) | 134 | (benzyl, NHCO2Me) | 135 | (2-F-benzyl, NHCO2Me) |

TABLE 1-continued

Examples 1-219

TABLE 1-continued

Examples 1-219

TABLE 1-continued

Examples 1-219

TABLE 1-continued
Examples 1-219
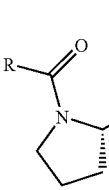
| Entry | R⟶ structure | Entry | R⟶ structure | Entry | MeO-C(O)-NH-CH(Ph)-C(O)⟶ structure |
|---|---|---|---|---|---|
| 193 | 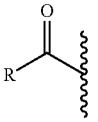 | 194 | 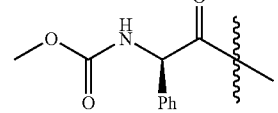 | 195 | 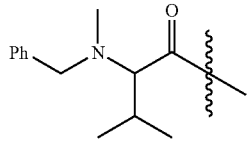 |
| 196 | 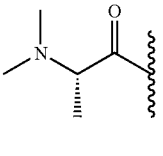 | 197 | 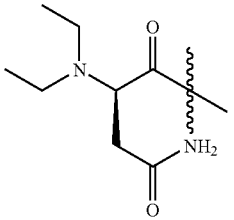 | 198 | 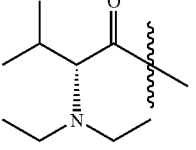 |
| 199 | 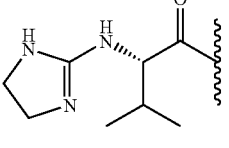 | 200 | 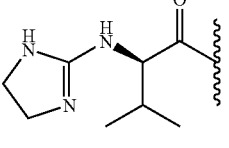 | 201 | 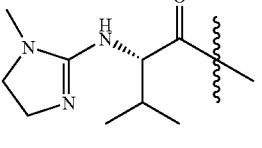 |
| 202 | 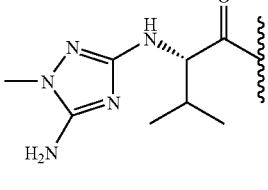 | 203 | 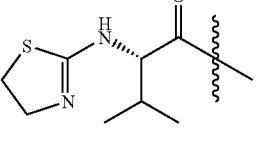 | 204 | 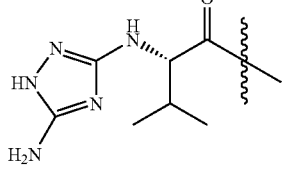 |
| 205 | 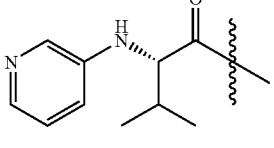 | 206 | 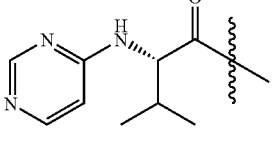 | 207 | 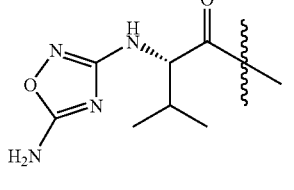 |
| 208 | 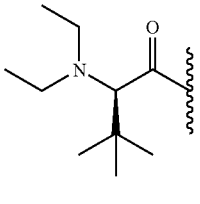 | 209 | 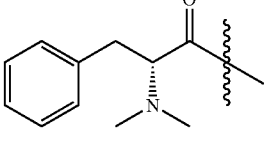 | 210 | |

TABLE 1-continued

Examples 1-219

| Entry | | Entry | | Entry | |
|---|---|---|---|---|---|
| 211 | (pyrrolidine-2-carbonyl) | 212 | (5-oxopyrrolidine-2-carbonyl) | 213 | (pyrimidin-5-ylamino-valeryl) |
| 214 | (4,4-difluoropyrrolidine-2-carbonyl) | 215 | (4-fluoropyrrolidine-2-carbonyl) | 216 | (3-azabicyclo[3.1.0] pyrrolidine-2-carbonyl) |
| 217 | (1-methylpyrrolidine-2-carbonyl) | 218 | (1-methyl-4-fluoropyrrolidine-2-carbonyl) | 219 | (4-fluoropyrrolidine-2-carbonyl) |

TABLE 2

Examples 220-229

| Example | R | R' | R" | X | Example | R | R' | R" | X |
|---|---|---|---|---|---|---|---|---|---|
| 220 | Me | H | H | CH₂ | 221 | H | H | H | CF₂ |
| 222 | Me | H | H | S | 223 | H | H | H | CHF (F up) |
| 224 | Me | H | H | O | 225 | H | H | H | CHF (F down) |

TABLE 2-continued
Examples 220-229
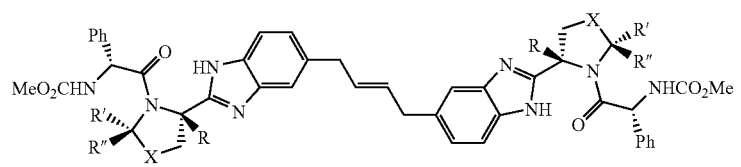
| Example | R | R' | R" | X | Example | R | R' | R" | X |
|---|---|---|---|---|---|---|---|---|---|
| 226 | H | Ph | H | CH$_2$ | 227 | H | H | H | ⸺CH(OH)CH$_3$ |
| 228 | H | H | Ph | CH$_2$ | 229 | H | H | H | ⸺CH(OH)CH$_3$ |
Example 230
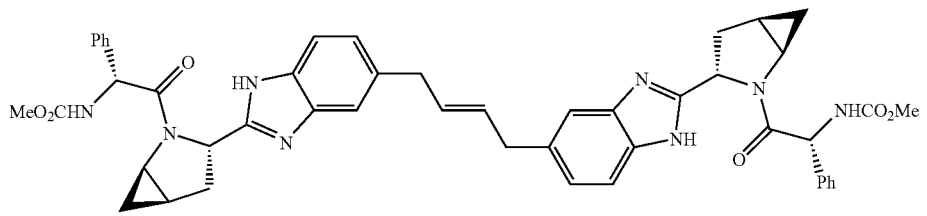
Example 231
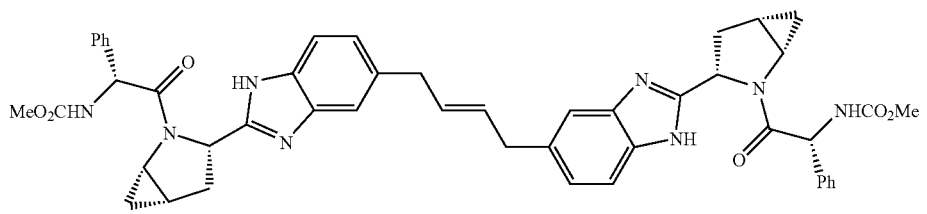
Example 232
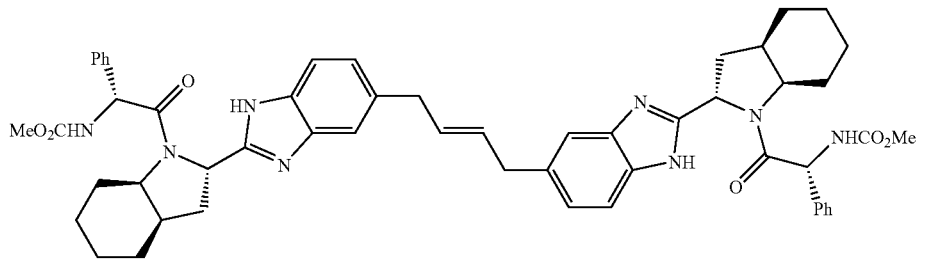

Example 233
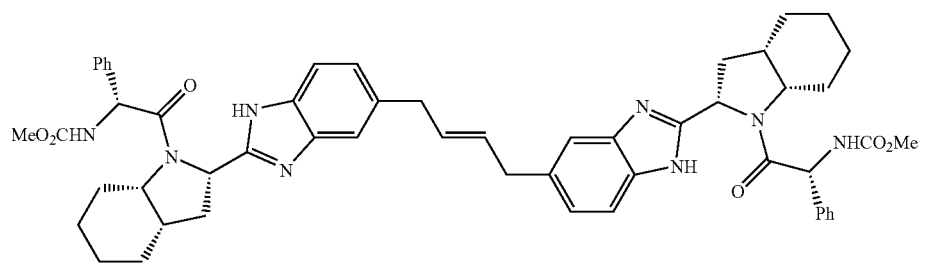
TABLE 3
Examples 234-243
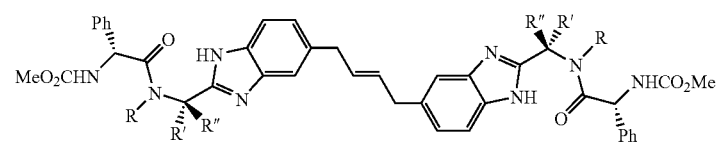
| Example | R | R' | R" | Example | R | R' | R" |
|---|---|---|---|---|---|---|---|
| 234 | Me | Me | H | 235 | H | Me | H |
| 236 | Me | H | Me | 237 | cyclopropyl | Me | H |
| 238 | Me | Me | Me | 239 | Me | cyclopropyl | H |
| 240 | Me | Allyl | H | 241 | Et | Me | H |
| 242 | Me | CHMe₂ | H | 243 | Me | Et | H |
TABLE 4
Examples 244-263
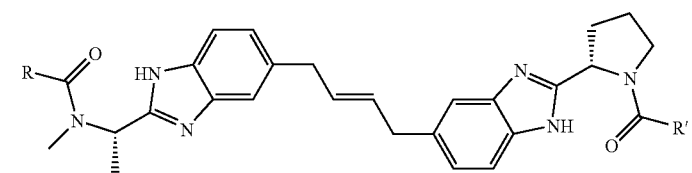
| Example | R | R' |
|---|---|---|
| 244 | MeO₂CHN–CH(Ph)– | MeO₂CHN–CH(Ph)– |
| 245 | Me₂N–CH(Ph)– | Me₂N–CH(Ph)– |
| 246 | Me₂N–CH(Ph)– | MeO₂CHN–CH(Ph)– |
| 247 | MeO₂CHN–CH(Ph)– | Me₂N–CH(Ph)– |

TABLE 4-continued
Examples 244-263
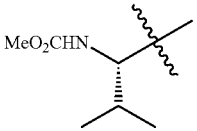
| Example | R | R' |
|---|---|---|
| 248 | 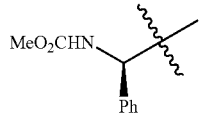 | 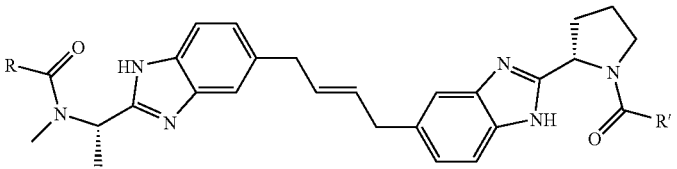 |
| 249 | 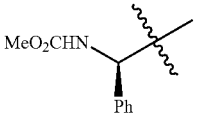 | 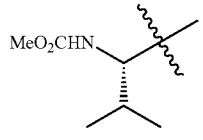 |
| 250 | 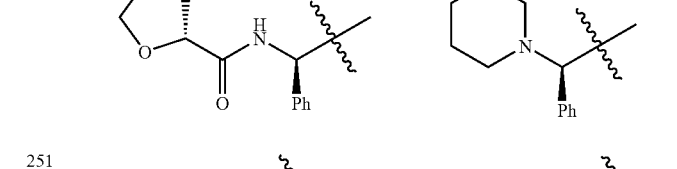 | 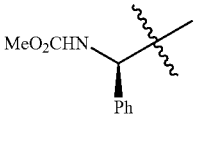 |
| 251 | 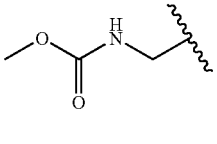 | 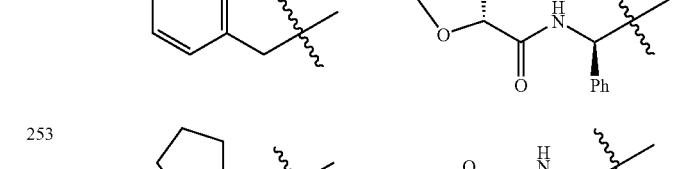 |
| 252 | 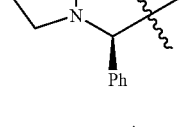 | 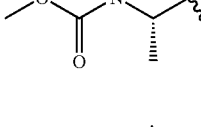 |
| 253 | 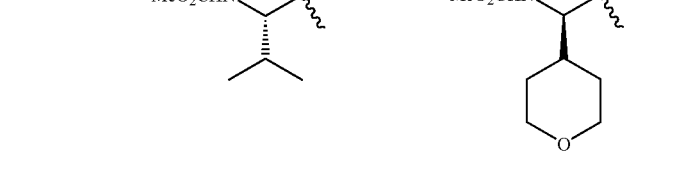 | 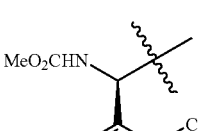 |
| 254 | 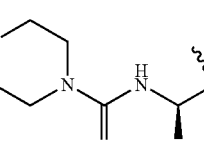 | 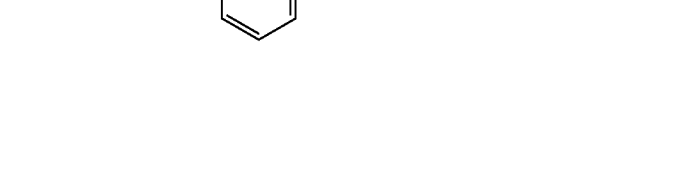 |
| 255 | 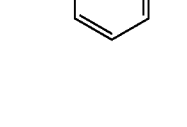 |  |

TABLE 4-continued
Examples 244-263
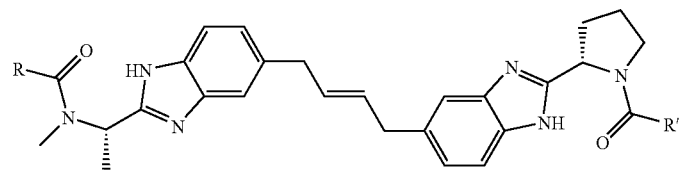
| Example | R | R' |
|---|---|---|
| 256 | MeO₂CHN— (iPr, Me) | MeO₂CHN— (iPr, Me) |
| 257 | tetrahydrofuran-2-yl-C(O)NH—CH(Ph)— | EtNHC(O)NH—CH(Ph)— |
| 258 | tetrahydropyran-4-yl-OC(O)NH—CH(iPr)— | MeO₂CHN— (iPr) |
| 259 | MeO₂CHN— (iPr) | pyrimidin-2-yl-NH—CH(iPr)— |
| 260 | MeO₂CHN—CH(cyclopropyl)— | MeO₂CHN—CH(CH(Me)OMe)— |
| 261 | MeO₂CHN— (iPr) | MeO₂CHN—CH(CH₂-pyrazol-1-yl)— |
| 262 | MeO₂CHN— (iPr) | MeO₂CHN-cyclopentyl— |

TABLE 4-continued

Examples 244-263

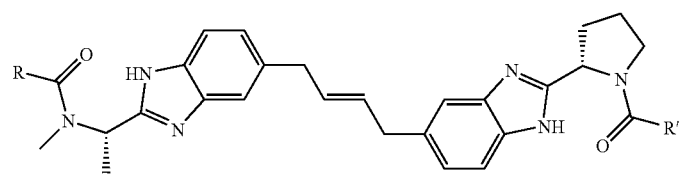

| Example | R | R' |
|---|---|---|
| 263 | MeO₂CHN...OMe | pyridin-3-yl-NH-CH(iPr)- |

TABLE 5

Examples 264-283

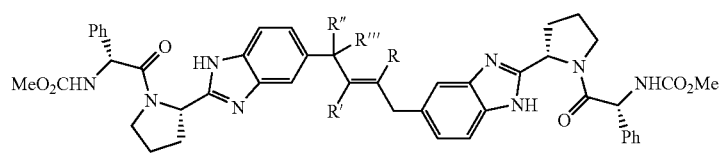

| Example | R | R' | R" | R''' | Example | R | R' | R" | R''' |
|---|---|---|---|---|---|---|---|---|---|
| 264 | F | H | H | H | 265 | F | H | F | H |
| 266 | F | F | H | H | 267 | Me | H | H | H |
| 268 | Me | Me | H | H | 269 | Me | H | Me | H |
| 270 | CF₃ | H | H | H | 271 | CF₃ | H | CF₃ | H |
| 272 | CF₃ | CF₃ | H | H | 273 | CO₂Me | H | H | H |
| 274 | CONH₂ | H | H | H | 275 | CO₂H | H | H | H |
| 276 | CH₂OH | H | H | H | 277 | CH₂NMe₂ | H | H | H |
| 278 | NMe₂ | H | H | H | 279 | OMe | H | H | H |
| 280 | OCF₃ | H | H | H | 281 | NHCO₂Me | H | H | H |
| 282 | Cl | H | H | H | 283 | Cl | H | Cl | H |

TABLE 6

Examples 284-309

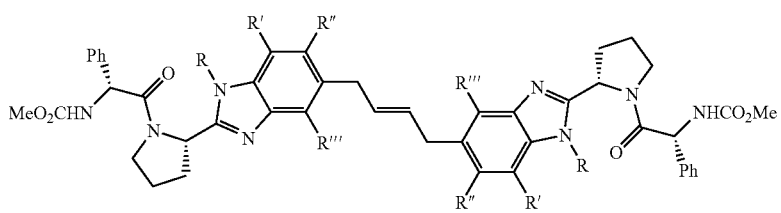

| Example | R | R' | R" | R''' | Example | R | R' | R" | R''' |
|---|---|---|---|---|---|---|---|---|---|
| 284 | Me | H | H | H | 285 | H | CO₂H | H | H |
| 286 | H | F | H | H | 287 | H | H | CO₂H | H |
| 288 | H | H | F | H | 289 | H | H | H | CO₂H |
| 290 | H | H | H | F | 291 | H | CO₂Me | H | H |
| 292 | H | Cl | H | H | 293 | H | H | CO₂Me | H |
| 294 | H | H | Cl | H | 295 | H | H | H | CO₂Me |
| 296 | H | H | H | Cl | 297 | H | CONH₂ | H | H |
| 298 | H | Me | H | H | 299 | H | H | CONH₂ | H |
| 300 | H | H | Me | H | 301 | H | H | H | CONH₂ |
| 302 | H | H | H | Me | 303 | H | OMe | H | H |
| 304 | H | CF₃ | H | H | 305 | H | H | OMe | H |
| 306 | H | H | CF₃ | H | 307 | H | H | H | OMe |
| 308 | H | H | H | CF₃ | 309 | CO₂Me | H | H | H |

TABLE 7
Examples 310-352
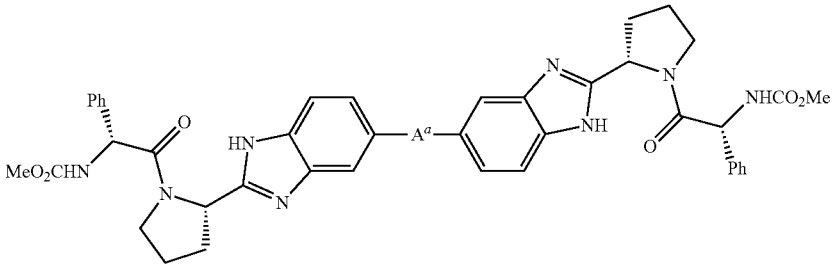

TABLE 7-continued

Examples 310-352

| Example | A$^a$ | Example | A$^a$ | Example | A$^a$ |
|---|---|---|---|---|---|
| 337 | | 338 | | 339 | |
| 340 | | 341 | | 342 | |
| 343 | | 344 | | 345 | |
| 346 | | 347 | | 348 | |
| 349 | | 350 | | 351 | |
| 352 | | | | | |

Biological Activity

1. HCV Replicon Cell Lines

HCV replicon cell lines (kindly provided by R. Bartenschlager) isolated from colonies as described by Lohman et. al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV), and (vi) HCV NS3 to NS5B genes that harbor cell culture adaptive mutations (E1202G, T1280I, K1846T) and the HCV 3'UTR.

These cell lines were maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat#15140-122, Invitrogen) and Geneticin (Cat#10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds and combinations were determined by HCV RNA detection using quantitative RT-PCR, according to the manufacturer's instructions, with a TaqMan® One-Step RT-PCR Master Mix Reagents Kit (Cat# AB 4309169, Applied Biosystems) on an ABI Model 7500 thermocycler. The TaqMan primers used for detecting and quantifying were obtained from Integrated DNA Technologies. HCV RNA was normalized to GAPDH RNA levels in drug-treated cells, which was detected and quantified using the Human GAPDH Endogenous Control Mix (Applied Biosystems, AB 4310884E). Total cellular RNA was purified from 96-well plates using the RNAqueous 96 kit (Ambion, Cat# AM1812). Chemical agent cytotoxicity was evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We used the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat. # 31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat. # 31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention may inhibit HCV by mechanisms in addition to or other than NS5A inhibition. In one embodiment the compounds of the present invention inhibit HCV replicon and in another embodiment the compounds of the present invention inhibit NS5A.

The compounds of the present invention can be effective against the HCV 1b genotype. It should also be understood that the compounds of the present invention can inhibit multiple genotypes of HCV. In one embodiment, compound of the present invention are active against the 1a, 1b, 2a, 2b, 3a, 4a, and 5a genotypes. Table 25 shows the $EC_{50}$ values of representative compounds of the present invention against the HCV 1b genotype from the above described qRT-PCR or luciferase assay. $EC_{50}$ ranges against HCV 1b are as follows: A >10 nM; B 1-10 nM; C<1 nM.

TABLE 8

| Genotype-1b replicon $EC_{50}$ | | | | | |
|---|---|---|---|---|---|
| Example | Range | Example | Range | Example | Range |
| 3a | C | 310 | C | 2-354 | C |
| 355 | C | 357 | A | | |

What is claimed is:

1. A compound represented by Formula (I):

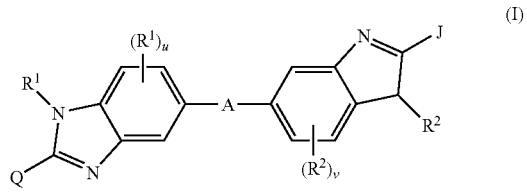

(I)

or a pharmaceutically acceptable salt thereof, wherein:

A is an optionally substituted $C_2$-$C_8$ alkenyl, or is an optionally substituted linear aliphatic group containing one or more groups selected from $S(O)_2$, C(O)O, OC(O)O, OC(O)N($R^{11}$), S(O)$_2$N($R^{11}$), N($R^{11}$)C(O)N($R^{11}$), N($R^{11}$)C(O)C(O)N($R^{11}$), N($R^{11}$)S(O)$_2$N($R^{11}$), C(O)N($R^{11}$)S(O)$_2$, C(O)N($R^{11}$)S(O)$_2$N($R^{11}$), and O;

$R^1$ and $R^2$ at each occurrence are each independently selected from the group consisting of hydrogen, halogen, cyano, optionally substituted $C_1$-$C_4$ alkyl, —O—$R^{11}$, —N$R^aR^b$, —C(O)$R^{11}$, —CO$_2R^{11}$, and —C(O)N$R^aR^b$;

$R^{11}$ at each occurrence is independently hydrogen or optionally substituted $C_1$-$C_8$ alkyl;

$R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;

u and v are each independently 1, 2, or 3;

Q and J are each independently selected from:

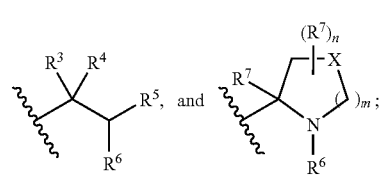

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; or alternatively, $R^3$ and $R^4$ can be taken together with the carbon atom to which they are attached to form optionally substituted $C_3$-$C_8$ cycloalkyl or optionally substituted heterocyclic;

R⁵ at each occurrence is independently hydrogen, optionally substituted $C_1$-$C_8$ alkyl, or optionally substituted $C_3$-$C_8$ cycloalkyl;

R⁶ is selected from the group consisting of —C(O)—R¹², —C(O)—C(O)—R¹², —S(O)₂—R¹², and —C(S)—R¹²;

R¹² at each occurrence is independently selected from the group consisting of —O—R¹¹, —NRᵃRᵇ, —R¹³, and —NRᶜRᵈ; wherein R¹³ at each occurrence is independently selected from the group consisting of: hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;

Rᶜ and Rᵈ at each occurrence are each independently selected from the group consisting of hydrogen, —R¹³, —C(O)—R¹³, —C(O)—OR¹³, —S(O)₂—R¹³, —C(O)N(R¹³)₂, and —S(O)₂N(R¹³)₂;

m is 0, 1, or 2;

n is 1, 2, 3, or 4;

X at each occurrence is independently selected from O, S, S(O), SO₂, and C(R⁷)₂; provided that when m is 0, X is C(R⁷)₂; and R⁷ at each occurrence is independently selected from the group consisting of: hydrogen, halogen, cyano, —O—R¹¹, —NRᵃRᵇ, optionally substituted aryl, optionally substituted heteroaryl, and optionally substituted —$C_1$-$C_4$ alkyl; or two vicinal R⁷ groups can be taken together with the two adjacent atoms to which they are attached to form a fused, optionally substituted $C_3$-$C_8$ cycloalkyl or optionally substituted heterocyclic ring; or alternatively two geminal R⁷ groups can be taken together with the carbon atom to which they are attached to form a spiro, optionally substituted $C_3$-$C_8$ cycloalkyl or optionally substituted heterocyclic ring.

2. The compound of claim 1, wherein Q and J are each independently selected from:

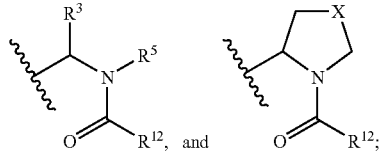

wherein X is independently CH₂, CF₂, CHF, or CH(OH); or a pharmaceutically acceptable salt thereof.

3. The compound of claim 1, wherein Q and J are each independently

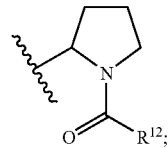

or a pharmaceutically acceptable salt thereof.

4. The compound of claim 1, wherein u and v at each occurrence are each 1; and R¹ and R² at each occurrence are each independently selected from the group consisting of hydrogen, halogen or optionally substituted $C_1$-$C_4$ alkyl; or a pharmaceutically acceptable salt thereof.

5. The compound of claim 1, wherein Q and J at each occurrence are each independently

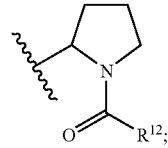

and R¹ and R² are each hydrogen; or a pharmaceutically acceptable salt thereof.

6. The compound of claim 1, wherein A is optionally substituted $C_2$-$C_8$ alkenyl; or a pharmaceutically acceptable salt thereof.

7. The compound of claim 1, wherein A is a linear aliphatic group containing a group selected from S(O)₂, C(O)O, OC(O)O, OC(O)N(R₁₁), S(O)₂N(R¹¹), N(R¹¹)C(O)N(R¹¹), N(R¹¹)C(O)C(O)N(R¹¹), N(R¹¹)S(O)₂N(R¹¹), C(O)N(R¹¹)S(O)₂ and C(O)N(R¹¹)S(O)₂N(R¹¹); or a pharmaceutically acceptable salt thereof.

8. The compound of claim 1, wherein A is a linear aliphatic group containing O or a pharmaceutically acceptable salt thereof.

9. The compound of claim 1, wherein A is a linear aliphatic group containing one to four carbons and two groups independently selected from the group consisting of O, S(O)₂, C(O)O, OC(O)O, OC(O)N(R¹¹), S(O)₂N(R¹¹), N(R¹¹)C(O)N(R¹¹), N(R¹¹)C(O)C(O)N(R¹¹), N(R¹¹)S(O)₂N(R¹¹), C(O)N(R¹¹)S(O)₂ and C(O)N(R¹¹)S(O)₂N(R¹¹); or a pharmaceutically acceptable salt thereof.

10. A compound selected from the group of compounds 1-393:

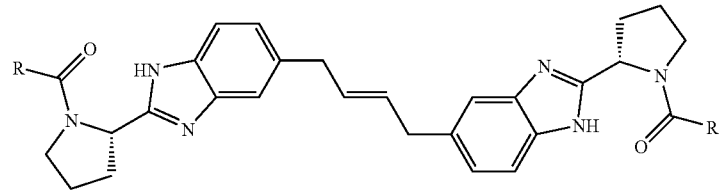

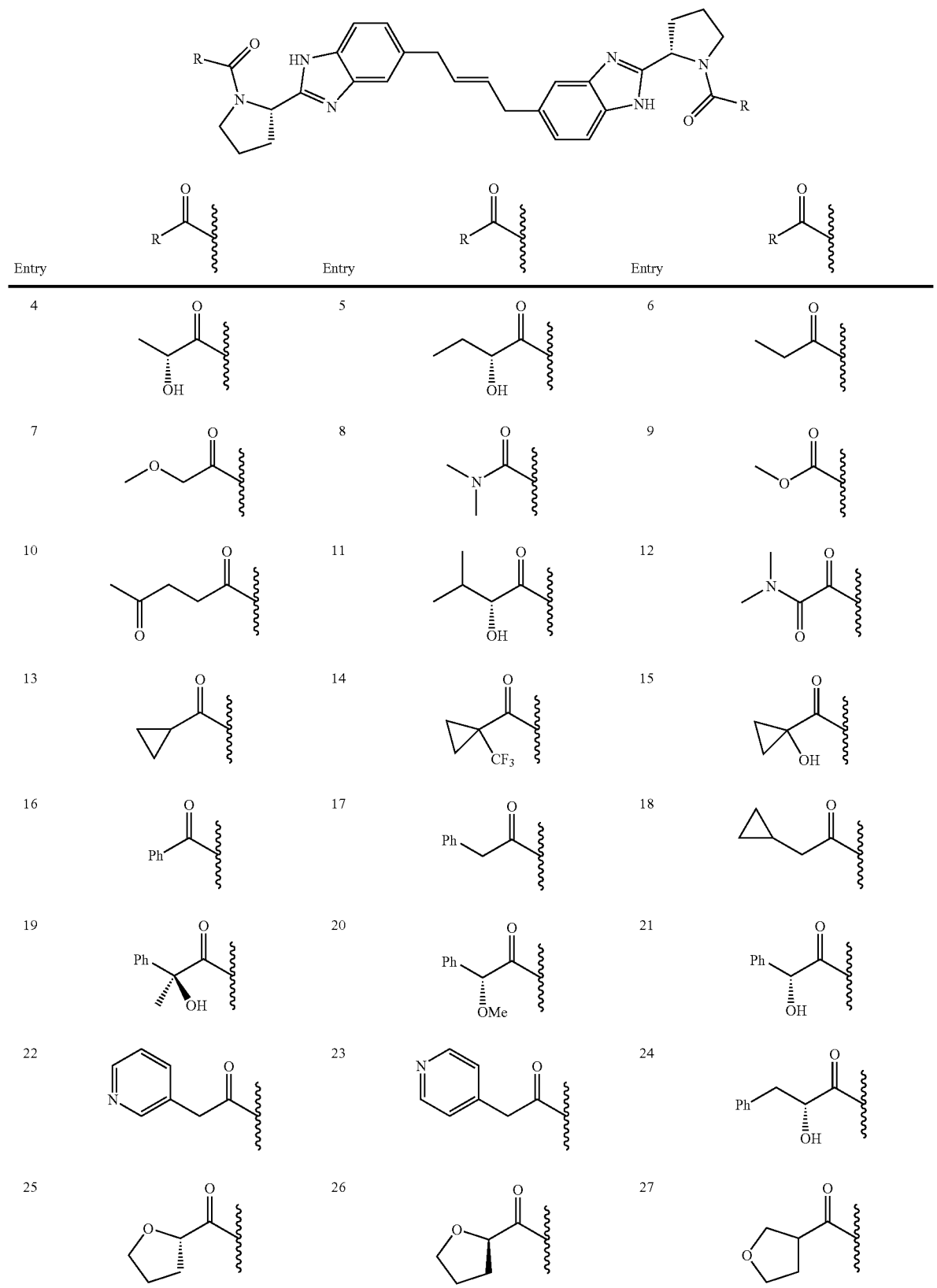

-continued
Compounds 1-219
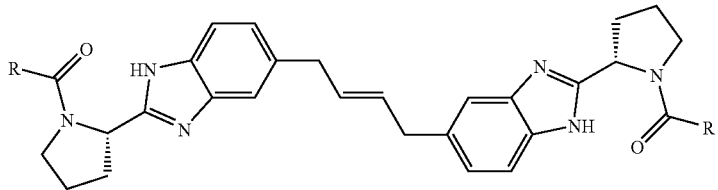
| Entry | | Entry | | Entry | |
|---|---|---|---|---|---|
| 28 | 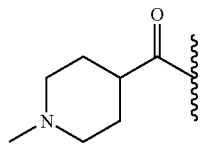 | 29 | 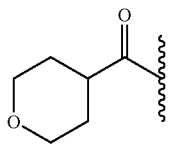 | 30 | 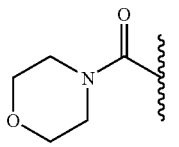 |
| 31 | 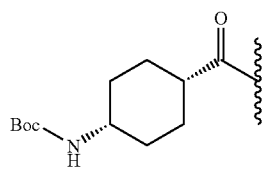 | 32 | 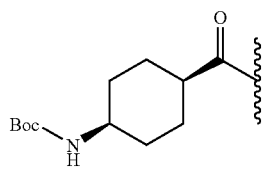 | 33 | 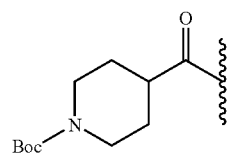 |
| 34 | 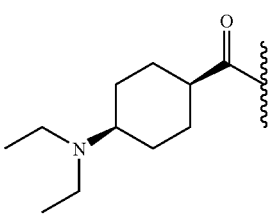 | 35 | 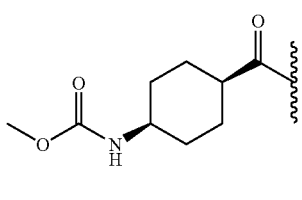 | 36 | 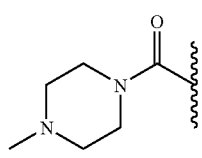 |
| 37 | 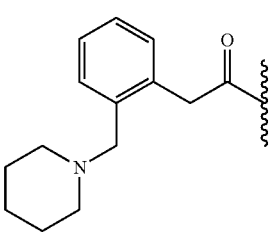 | 38 | 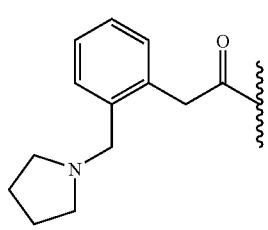 | 39 | 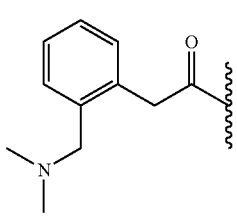 |
| 40 | 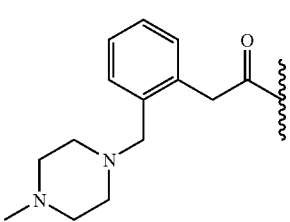 | 41 | 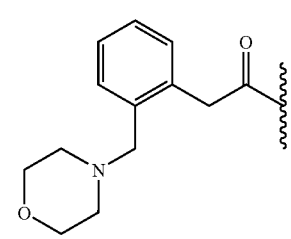 | 42 | 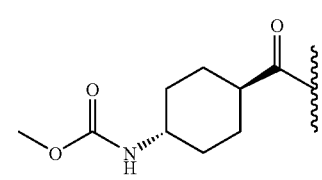 |
| 43 | 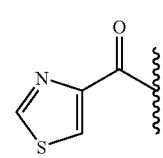 | 44 | 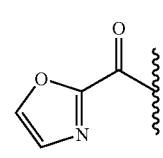 | 45 | 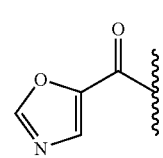 |

-continued
Compounds 1-219
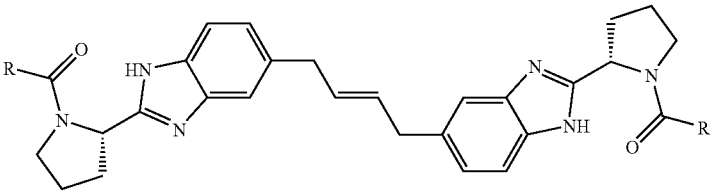
| Entry | | Entry | | Entry | |
|---|---|---|---|---|---|
| 46 | 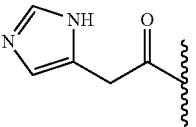 | 47 | 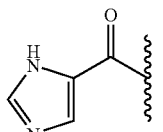 | 48 | 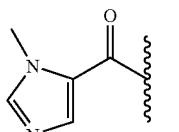 |
| 49 | 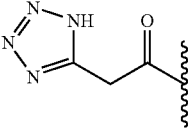 | 50 | 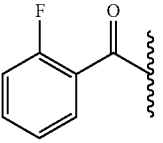 | 51 | 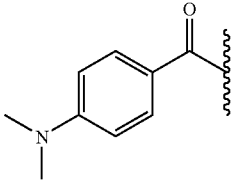 |
| 52 | 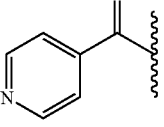 | 53 | 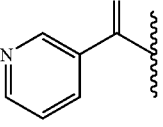 | 54 | 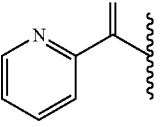 |
| 55 | 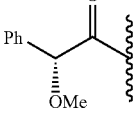 | 56 | 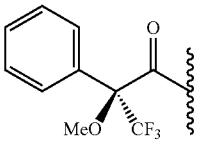 | 57 | 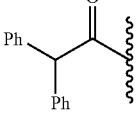 |
| 58 | 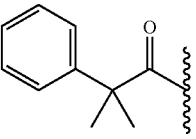 | 59 | 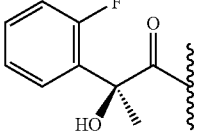 | 60 | 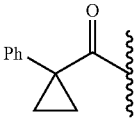 |
| 61 | 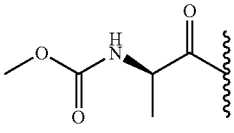 | 62 | 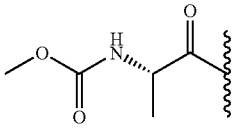 | 63 | 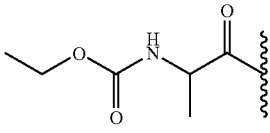 |
| 64 | 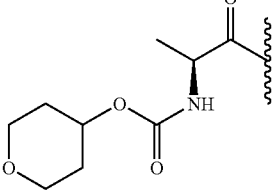 | 65 | 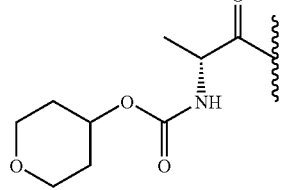 | 66 | 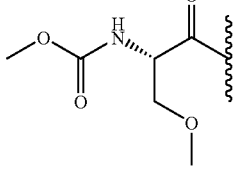 |

-continued
Compounds 1-219
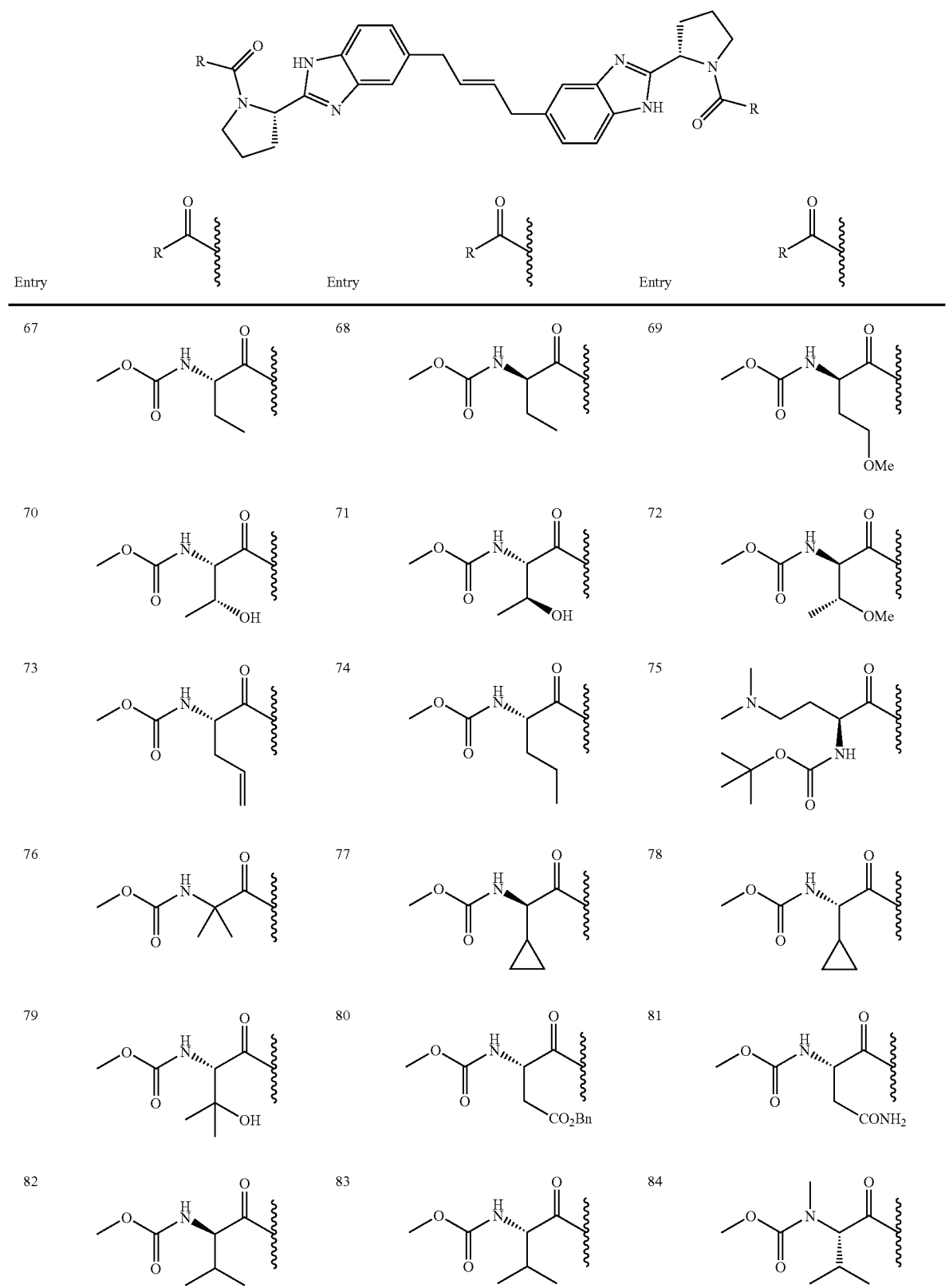

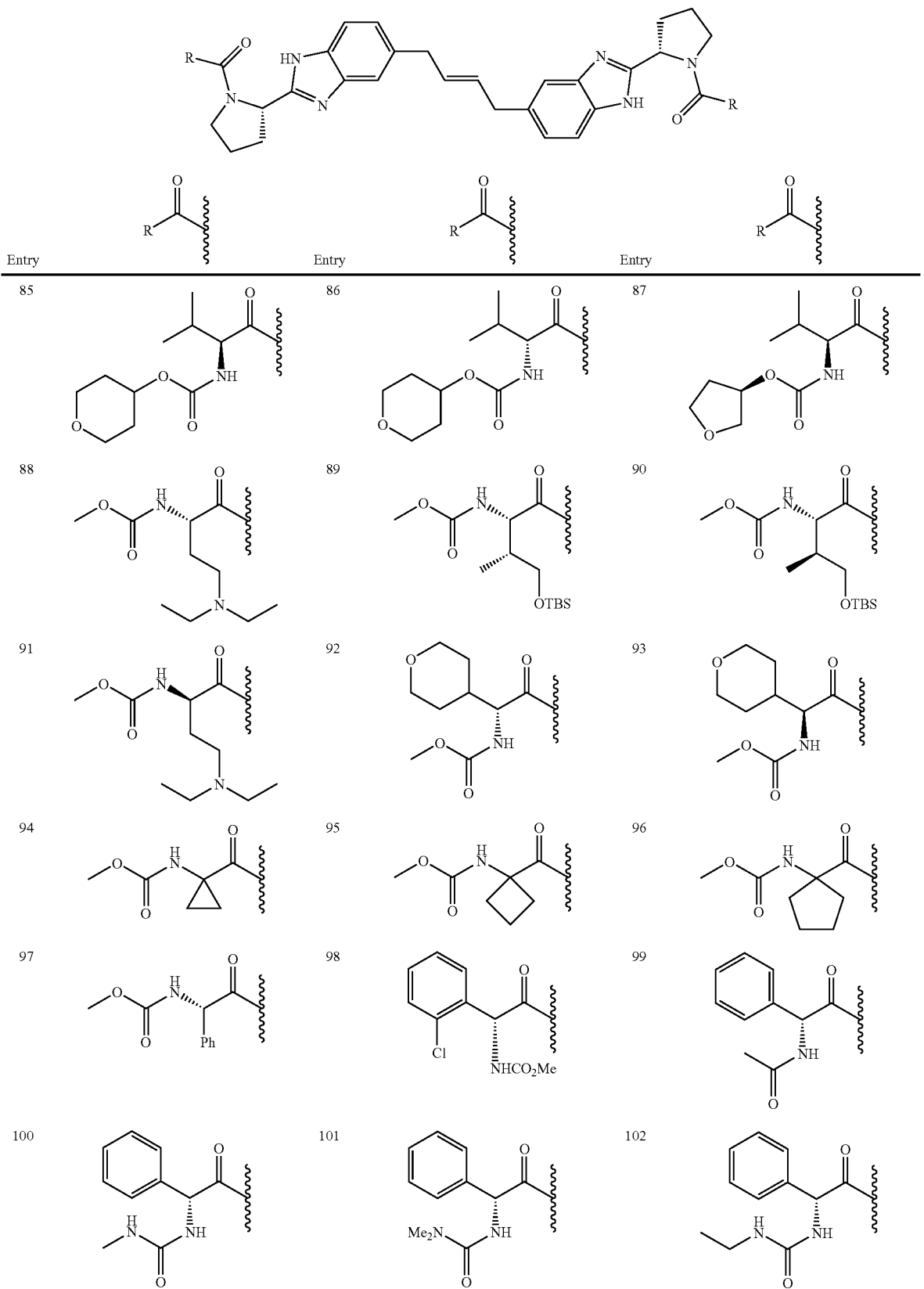

-continued
Compounds 1-219
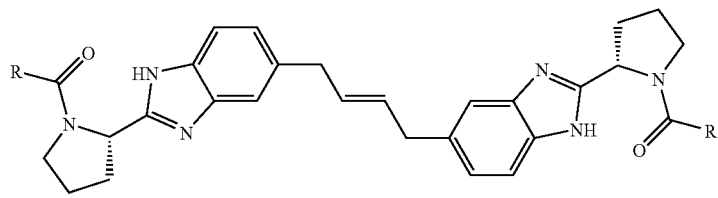
| Entry | | Entry | | Entry | |
|---|---|---|---|---|---|
| 103 | 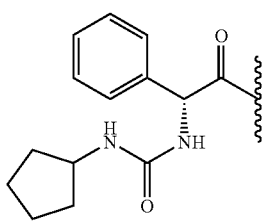 | 104 | 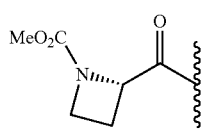 | 105 | 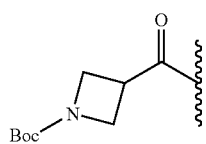 |
| 106 | 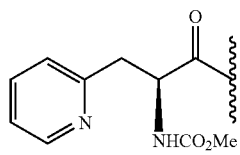 | 107 | 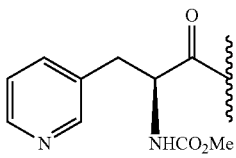 | 108 | 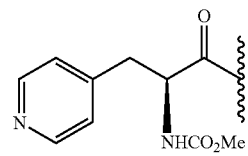 |
| 109 | 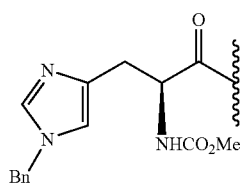 | 110 | 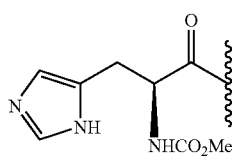 | 111 | 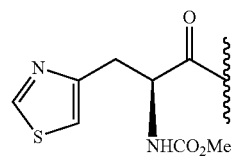 |
| 112 | 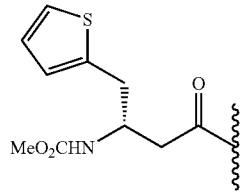 | 113 | 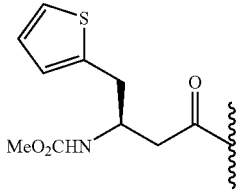 | 114 | 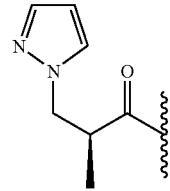 |
| 115 | 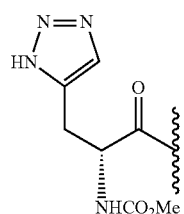 | 116 | 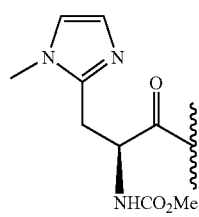 | 117 | 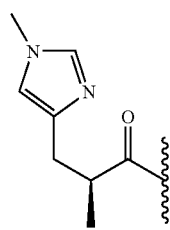 |

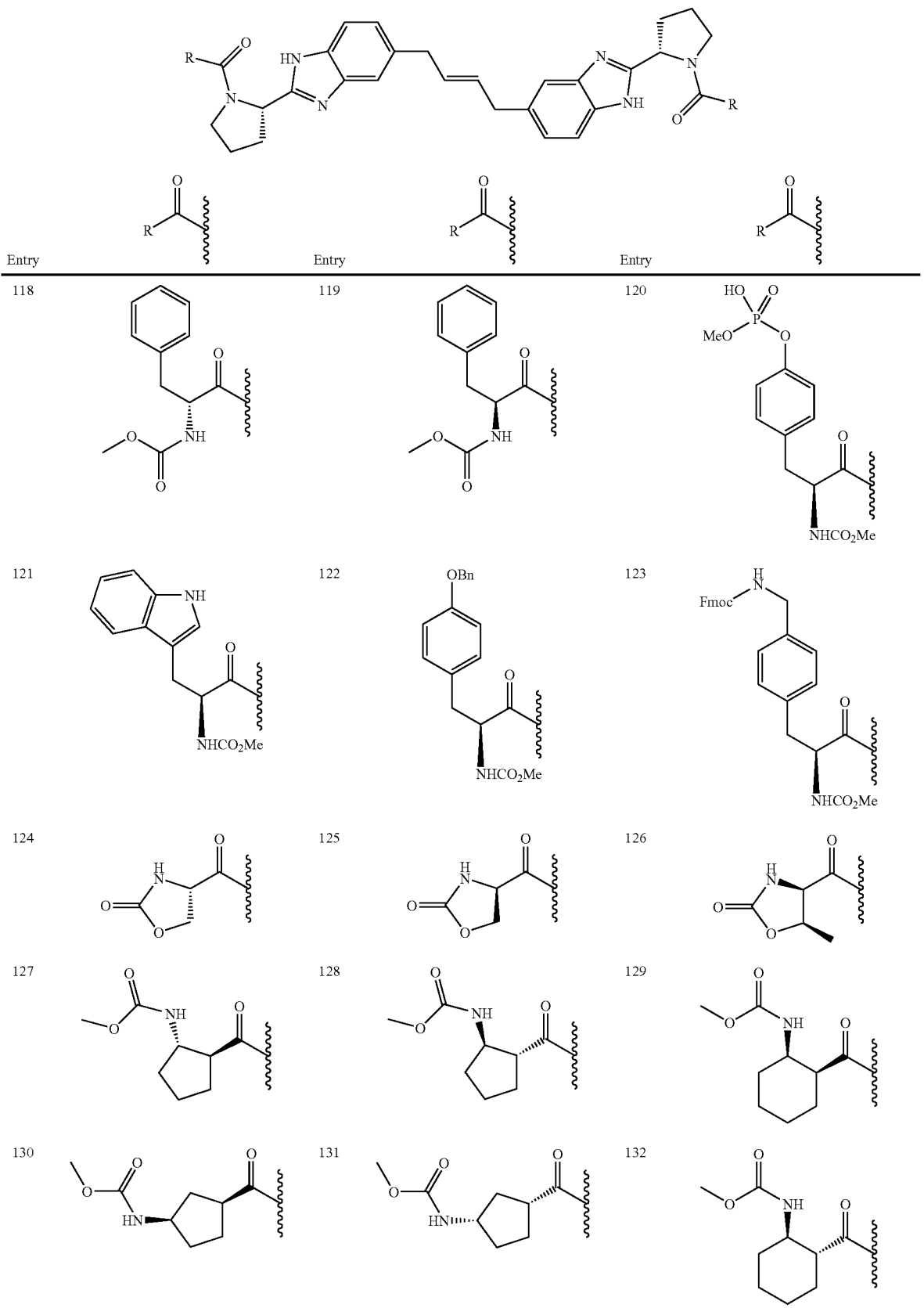

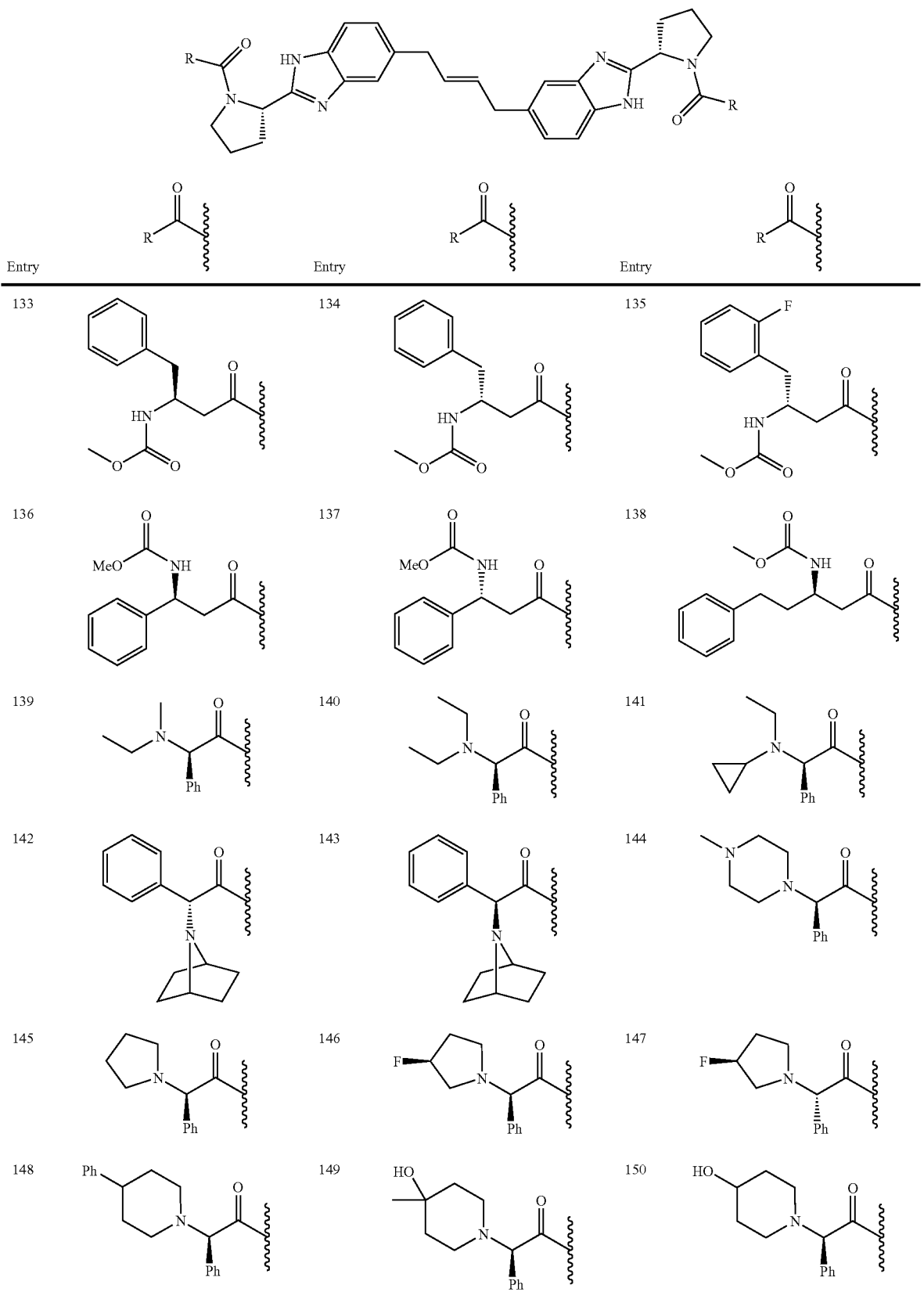

-continued

Compounds 1-219

| Entry | | Entry | | Entry | |
|---|---|---|---|---|---|
| 151 | piperazinone-N-CH(Ph)-C(O)- | 152 | morpholine-N-CH(Ph)-C(O)- | 153 | piperidine-N-CH(Ph)-C(O)- |
| 154 | Bn-O-C(O)-piperazine-N-CH(Ph)-C(O)- | 155 | 2-CF₃-C₆H₄-CH(NMe₂)-C(O)- | 156 | 3-CF₃-C₆H₄-CH(NMe₂)-C(O)- |
| 157 | pyridin-3-yl-CH(NMe₂)-C(O)- | 158 | pyridin-2-yl-CH(NMe₂)-C(O)- | 159 | pyridin-4-yl-CH(NMe₂)-C(O)- |
| 160 | 3-Cl-C₆H₄-CH(NMe₂)-C(O)- | 161 | 2-Cl-C₆H₄-CH(NMe₂)-C(O)- | 162 | 6-Cl-pyridin-3-yl-CH(NMe₂)-C(O)- |
| 163 | 2-F-C₆H₄-CH(NMe₂)-C(O)- | 164 | 2-Cl-C₆H₄-CH(NMe₂)-C(O)- | 165 | 4-Cl-C₆H₄-CH(NMe₂)-C(O)- |
| 166 | 2-F-C₆H₄-CH(NMe₂)-C(O)- | 167 | 2-F-C₆H₄-CH(NMe₂)-C(O)- | 168 | 3-F-C₆H₄-CH(NMe₂)-C(O)- |

-continued

Compounds 1-219

Compounds 1-219
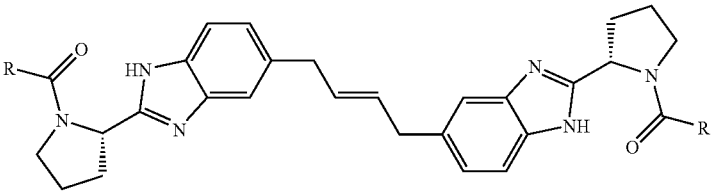
| Entry | | Entry | | Entry | |
|---|---|---|---|---|---|
| 187 | 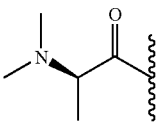 | 188 | 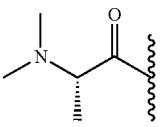 | 189 | 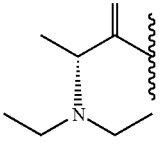 |
| 190 | 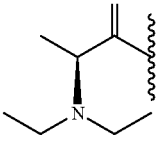 | 191 | 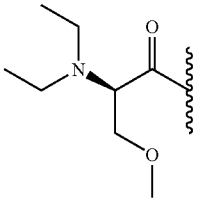 | 192 | 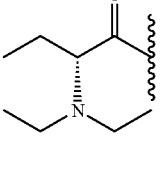 |
| 193 | 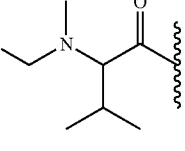 | 194 | 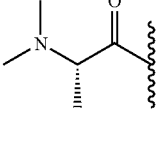 | 195 | 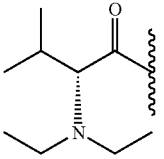 |
| 196 | 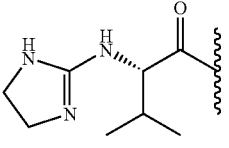 | 197 | 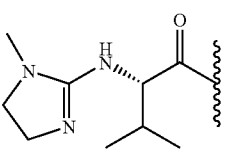 | 198 | 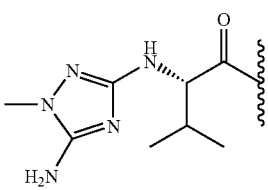 |
| 199 | | 200 | | 201 | |
| 202 | | 203 | | 204 | |

-continued
Compounds 1-219
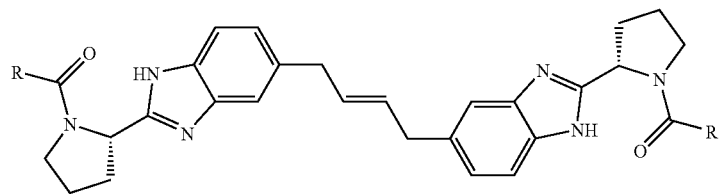
| Entry | | Entry | | Entry | |
|---|---|---|---|---|---|
| 205 | 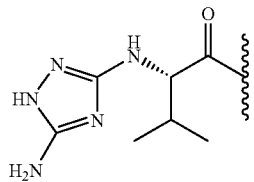 | 206 | 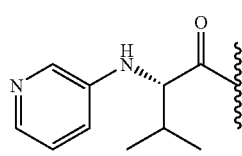 | 207 | 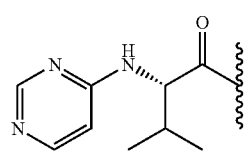 |
| 208 | 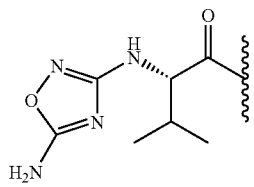 | 209 | 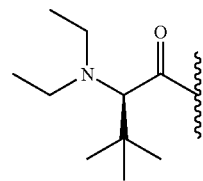 | 210 | 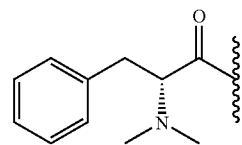 |
| 211 | 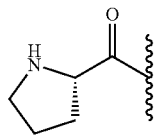 | 212 | 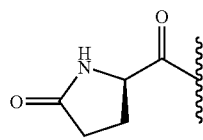 | 213 | 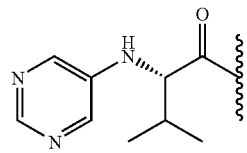 |
| 214 | 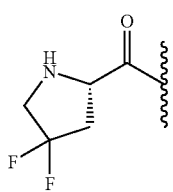 | 215 | 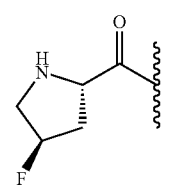 | 216 | 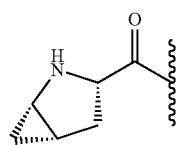 |
| 217 | 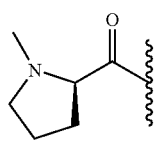 | 218 | 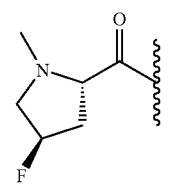 | 219 | 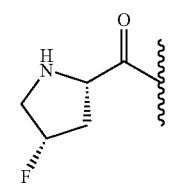 |

Compounds 220-229
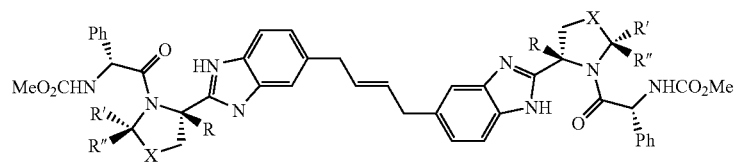
| Entry | R | R' | R" | X | Entry | R | R' | R" | X |
|---|---|---|---|---|---|---|---|---|---|
| 220 | Me | H | H | CH₂ | 221 | H | H | H | CF₂ |
| 222 | Me | H | H | S | 223 | H | H | H | ⸺CH(F)⸺ (H up, F down, Me) |
| 224 | Me | H | H | O | 225 | H | H | H | ⸺CH(F)⸺ (F up, H down, Me) |
| 226 | H | Ph | H | CH₂ | 227 | H | H | H | ⸺C(OH)⸺ (H up, OH down, Me) |
| 228 | H | H | Ph | CH₂ | 229 | H | H | H | ⸺C(OH)⸺ (OH up, H down, Me) |
Compound 230
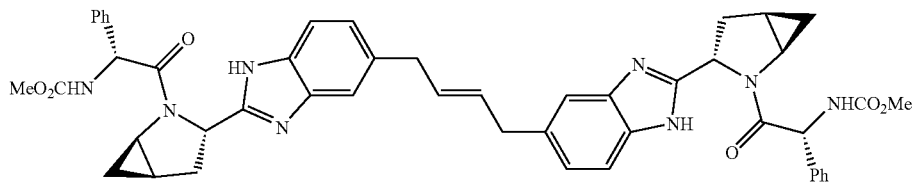
Compound 231
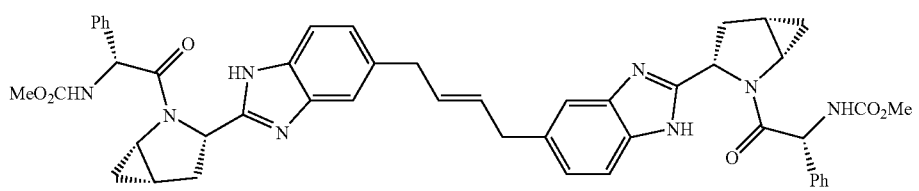
Compound 232
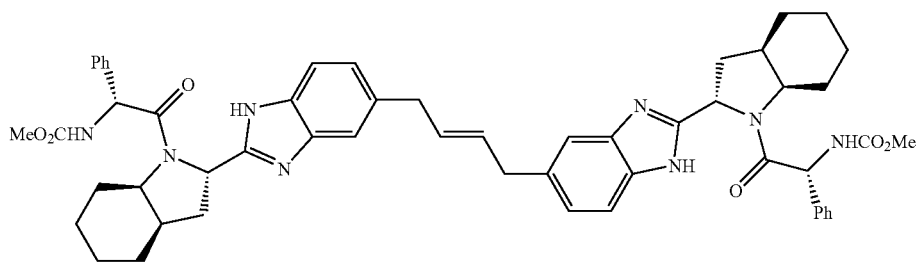

Compound 233
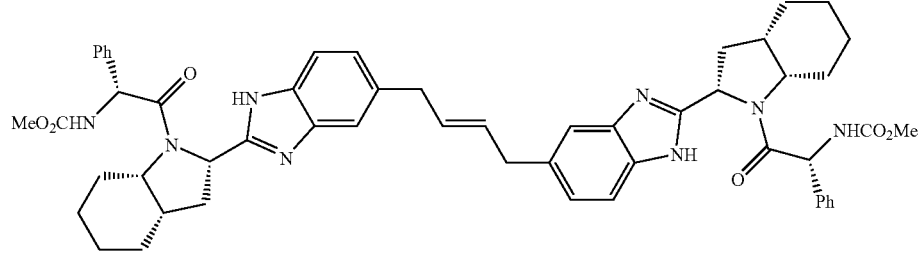
Compounds 234-243
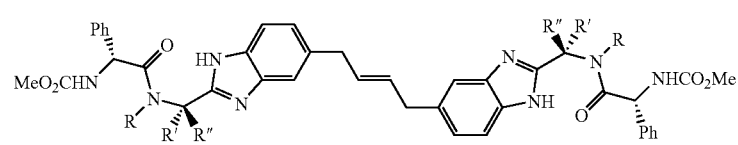
| Entry | R | R' | R" | Entry | R | R' | R" |
|---|---|---|---|---|---|---|---|
| 234 | Me | Me | H | 235 | H | Me | H |
| 236 | Me | H | Me | 237 | cyclopropyl | Me | H |
| 238 | Me | Me | Me | 239 | Me | cyclopropyl | H |
| 240 | Me | Allyl | H | 241 | Et | Me | H |
| 242 | Me | CHMe₂ | H | 243 | Me | Et | H |
Compounds 244-263
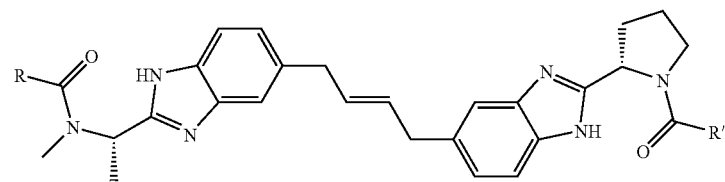
| Example | R | R' |
|---|---|---|
| 244 | MeO₂CHN—CH(Ph)— | MeO₂CHN—CH(Ph)— |
| 245 | Me₂N—CH(Ph)— | Me₂N—CH(Ph)— |
| 246 | Me₂N—CH(Ph)— | MeO₂CHN—CH(Ph)— |
| 247 | MeO₂CHN—CH(Ph)— | Me₂N—CH(Ph)— |

-continued
Compounds 244-263
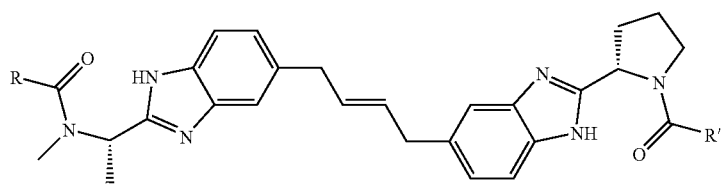
| Example | R | R' |
|---|---|---|
| 248 | 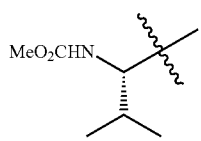 | 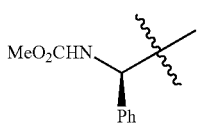 |
| 249 | 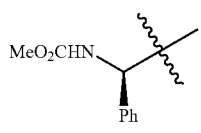 | 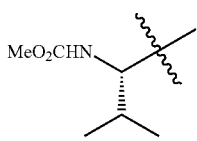 |
| 250 | 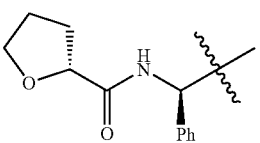 | 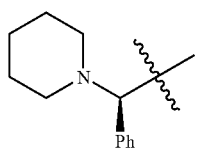 |
| 251 | 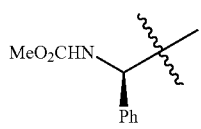 | 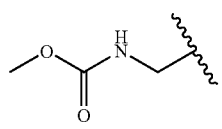 |
| 252 | 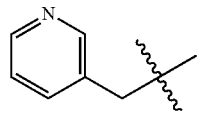 | 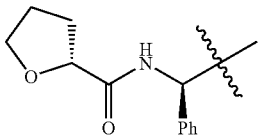 |
| 253 | 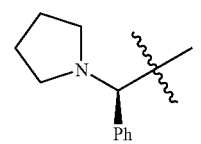 | 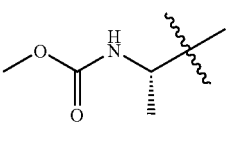 |
| 254 | 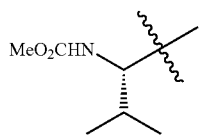 | 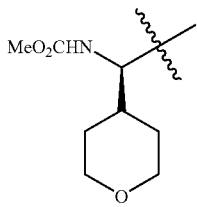 |
| 255 | 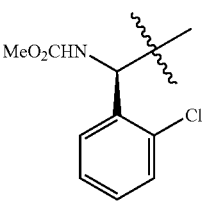 | 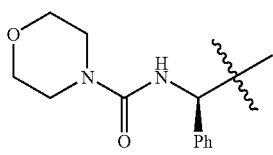 |

-continued
Compounds 244-263
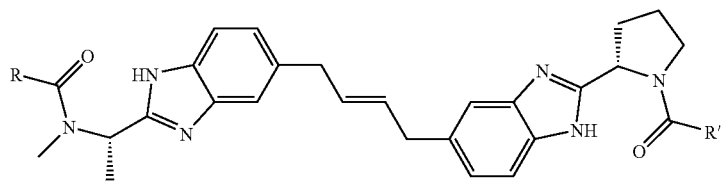
| Example | R | R' |
|---|---|---|
| 256 |  | |
| 257 | 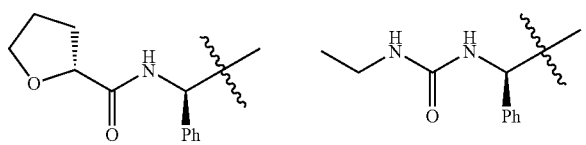 | |
| 258 | 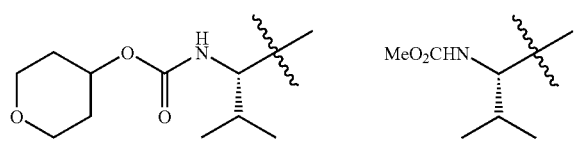 | |
| 259 | 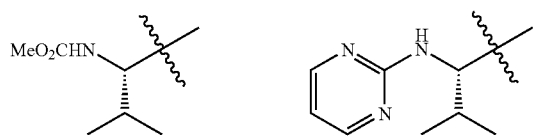 | |
| 260 | 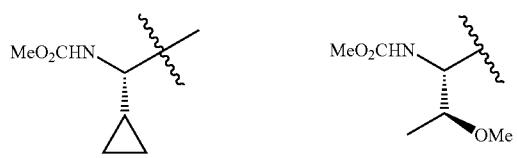 | |
| 261 | 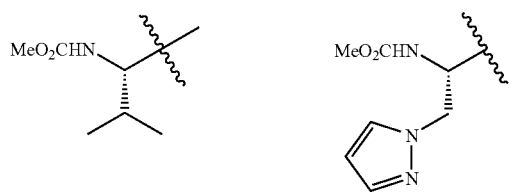 | |
| 262 | 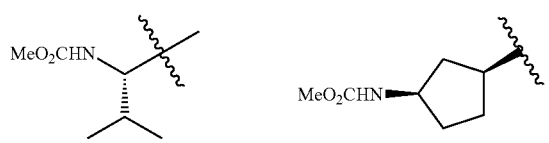 | |

Compounds 244-263

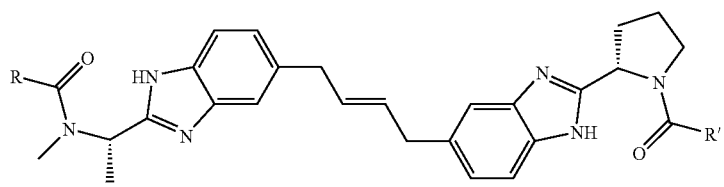

| Example | R | R' |
|---|---|---|
| 263 | 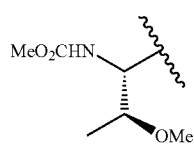 | 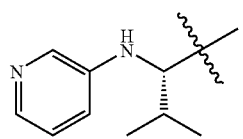 |

Compounds 264-283

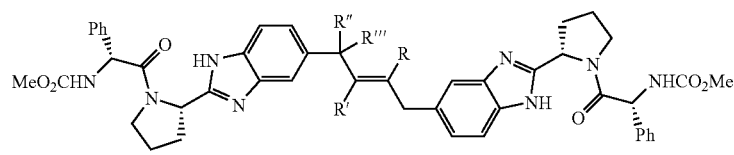

| Entry | R | R' | R'' | R''' | Entry | R | R' | R'' | R''' |
|---|---|---|---|---|---|---|---|---|---|
| 264 | F | H | H | H | 265 | F | H | F | H |
| 266 | F | F | H | H | 267 | Me | H | H | H |
| 268 | Me | Me | H | H | 269 | Me | H | Me | H |
| 270 | CF$_3$ | H | H | H | 271 | CF$_3$ | H | CF$_3$ | H |
| 272 | CF$_3$ | CF$_3$ | H | H | 273 | CO$_2$Me | H | H | H |
| 274 | CONH$_2$ | H | H | H | 275 | CO$_2$H | H | H | H |
| 276 | CH$_2$OH | H | H | H | 277 | CH$_2$NMe2 | H | H | H |
| 278 | NMe$_2$ | H | H | H | 279 | OMe | H | H | H |
| 280 | OCF$_3$ | H | H | H | 281 | NHCO$_2$Me | H | H | H |
| 282 | Cl | H | H | H | 283 | Cl | H | Cl | H |

Compounds 284-309

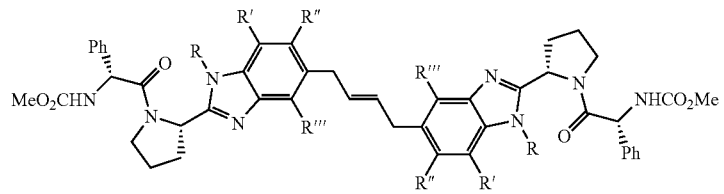

| Entry | R | R' | R'' | R''' | Entry | R | R' | R'' | R''' |
|---|---|---|---|---|---|---|---|---|---|
| 284 | Me | H | H | H | 285 | H | CO$_2$H | H | H |
| 286 | H | F | H | H | 287 | H | H | CO$_2$H | H |
| 288 | H | H | F | H | 289 | H | H | H | CO$_2$H |
| 290 | H | H | H | F | 291 | H | CO$_2$Me | H | H |
| 292 | H | Cl | H | H | 293 | H | H | CO$_2$Me | H |
| 294 | H | H | Cl | H | 295 | H | H | H | CO$_2$Me |
| 296 | H | H | H | Cl | 297 | H | CONH$_2$ | H | H |
| 298 | H | Me | H | H | 299 | H | H | CONH$_2$ | H |
| 300 | H | H | Me | H | 301 | H | H | H | CONH$_2$ |
| 302 | H | H | H | Me | 303 | H | OMe | H | H |
| 304 | H | CF$_3$ | H | H | 305 | H | H | OMe | H |
| 306 | H | H | CF$_3$ | H | 307 | H | H | H | OMe |
| 308 | H | H | H | CF$_3$ | 309 | CO$_2$Me | H | H | H |

Compounds 310-352
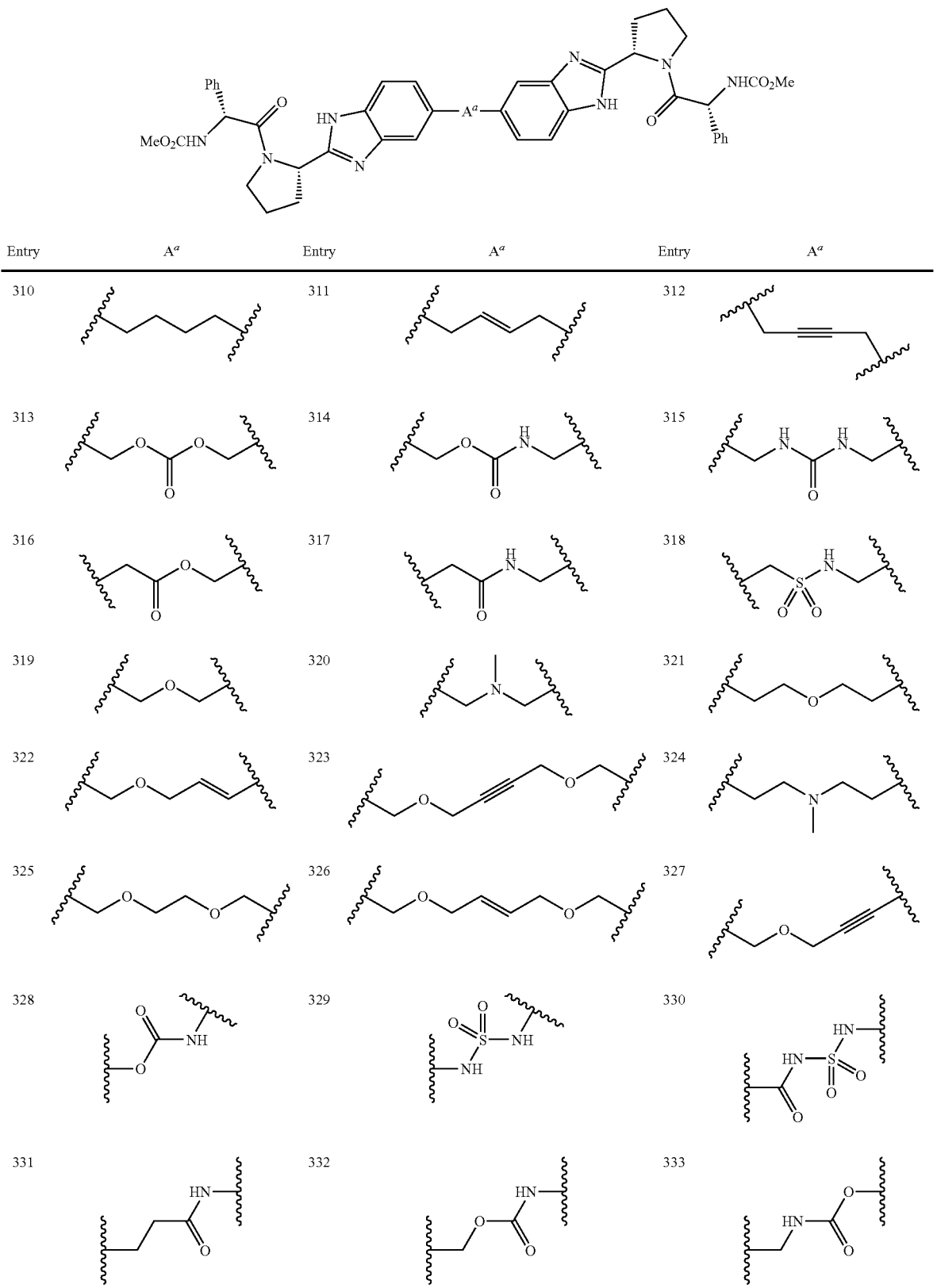

-continued
Compounds 310-352
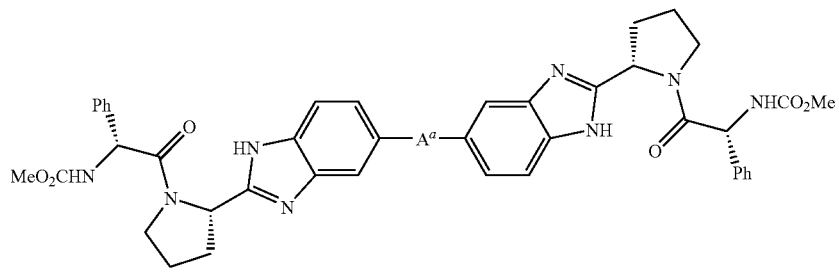
| Entry | $A^a$ | Entry | $A^a$ | Entry | $A^a$ |
|---|---|---|---|---|---|
| 334 | carbonate linker | 335 | HN-C(=O)-CH=CH- | 336 | HN-C(=O)-NH-CH2- |
| 337 | sulfamide linker | 338 | acylsulfonamide | 339 | -C≡C-CH2-O-C(=O)-NH- |
| 340 | -O-CH2-CH=C(CH3)- | 341 | -O-(CH2)4-O- | 342 | -N(CH3)-CH2-C≡C- |
| 343 | -O-CH2-CH2-O- | 344 | -O-CH2-C≡C-CH2-O- | 345 | -N(CH3)-CH2-CH2-N(CH3)- |
| 346 | -O-CH2-C≡C-CH2- | 347 | -O-CH2-CH=CH-CH2-O- | 348 | -O-CH2-CH2-N(CH3)2 |
| 349 | -O-CH2-C(=O)-O- | 350 | -O-CH2-CH2-NH-C(=O)-O- | 351 | -CH2-C(=O)-CH2-C(=O)-NH- |
| 352 | -C(=O)-CH2-S(=O)2-NH- | | | | |

11. A pharmaceutical composition comprising a compound or a combination of compounds according to claim 1 or a pharmaceutically acceptable salt thereof, in combination with a pharmaceutically acceptable carrier or excipient.

12. A method of inhibiting the replication of a hepatitis C virus comprising contacting said virus with a therapeutically effective amount of a compound or combination of compounds of claim 1, or a pharmaceutically acceptable salt thereof.

13. A method of therapeutically treating infection caused by hepatitis C virus comprising administering to a patient in need of such treatment a therapeutically effective amount of a compound or combination of compounds of claim 1, or a pharmaceutically acceptable salt thereof.

14. The method of claim 13, further comprising the step of co-administering one or more agents selected from the group consisting of a host immune modulator and an antiviral agent, or a combination thereof.

15. The method of claim 14, wherein the host immune modulator is selected from the group consisting of interferon-alpha, pegylated-interferon-alpha, interferon-beta,
  interferon-gamma, consensus interferon, a cytokine, and a vaccine.

16. The method of claim 14, wherein the antiviral agent inhibit replication of HCV by inhibiting host cellular functions associated with viral replication.

17. The method of claim 14, wherein the antiviral agent inhibits the replication of HCV by targeting proteins of the viral genome.

18. The method of claim 14, wherein said antiviral agent is an inhibitor of a HCV viral protein, a replication process or a combination thereof, wherein said protein or replication process is selected from the group consisting of helicase, protease, polymerase, metalloprotease, NS4A, NS4B, NS5A, assembly, entry, and internal ribosome entry site inhibitor.

19. The method of claim 13, further comprising the step of co-administering an agent or combination of agents that treat or alleviate symptoms of HCV infection selected from cirrhosis, inflammation of the liver and a combination thereof.

20. The method of claim 13, further comprising the step of co-administering one or more agents that treat symptoms of hepatitis B (HBV) infection.

21. The method of claim 13, further comprising the step of co-administering one or more agents that treat symptoms of human immunodeficiency virus (HIV) infection.

22. The pharmaceutical composition of claim 11, further comprising an agent selected from interferon, pegylated interferon, ribavirin, amantadine, an HCV protease inhibitor, an HCV polymerase inhibitor, an HCV helicase inhibitor, or an internal ribosome entry site inhibitor.

23. The composition of claim 11, further comprising a cytochrome P450 monooxygenase inhibitor or a pharmaceutically acceptable salt thereof.

24. The composition of claim 23, wherein the cytochrome P450 mooxygenase inhibitor is ritonavir.

25. A method of therapeutically treating hepatitis C viral infection in a subject in need thereof comprising co-administering to said subject a cytochrome P450 monooxygenase inhibitor or a pharmaceutically acceptable salt thereof, and a compound of claim 1 or a pharmaceutically acceptable salt thereof.

26. The compound of claim 1, wherein A is independently optionally substituted $C_2$-$C_8$ alkenyl; $R^1$ and $R^2$ are each hydrogen; Q and J are each independently

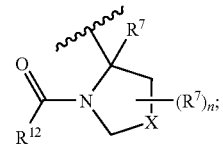

wherein n is 1 or 2; X at each occurrence is independently $CH_2$, $CF_2$, CHF, or $C(R^7)_2$; $R^{12}$ at each occurrence is independently $C_1$-$C_8$ alkyl optionally substituted with amino, hydroxy, phenyl, protected amino, or $O(C_1$-$C_4$ alkyl); $R^7$ at each occurrence is independently hydrogen, methyl, fluoro or hydroxy; or optionally, two vicinal $R^7$ groups taken together with the two adjacent atoms to which they are attached form a fused, optionally substituted cyclopropyl; or alternatively, two geminal $R^7$ groups taken together with the carbon atom to which they are attached form a spiro, optionally substituted cyclopropyl; or a pharmaceutically acceptable salt thereof.

27. The compound according to claim 1, selected from the group of compounds 1a, 3a, and 353-354 and 356-357:

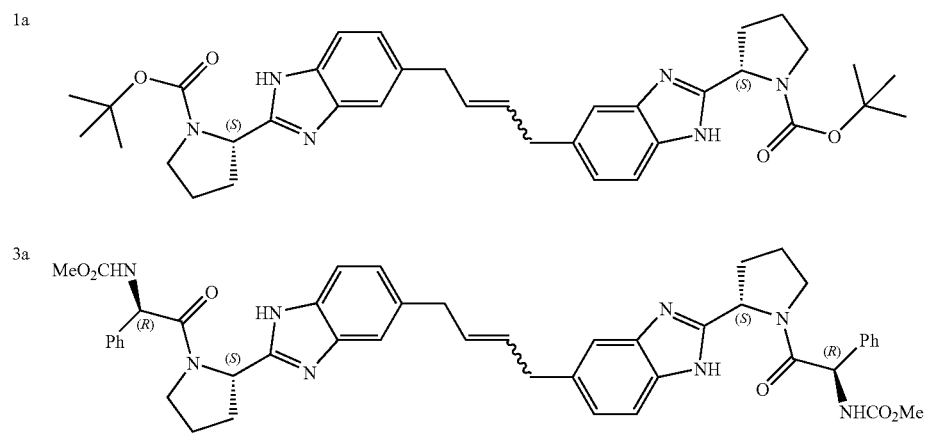

353

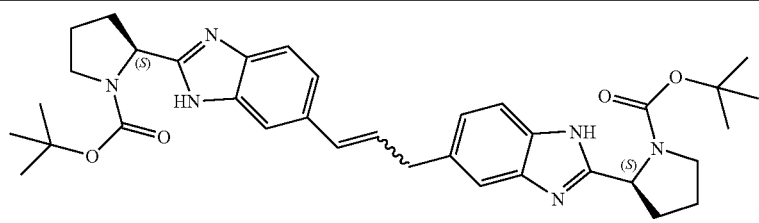

354

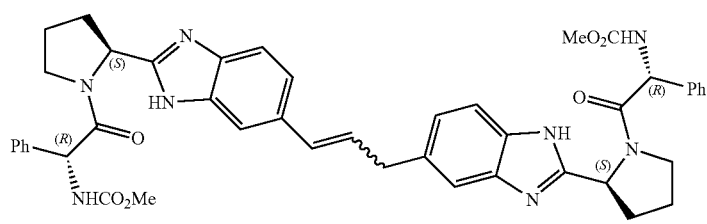

356

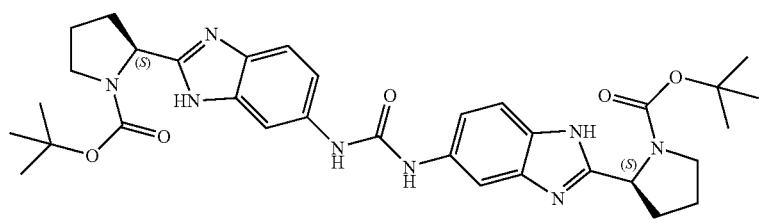

357

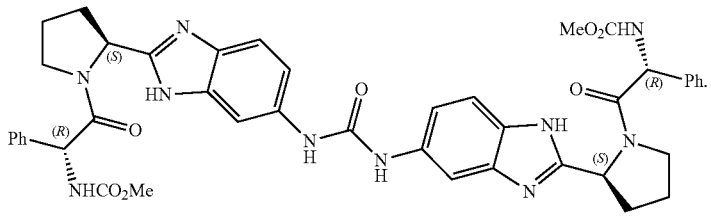

28. A process of making a compound according to claim 1 comprising the steps of:

i) preparing a compound of Formula (II-a):

(II-a)

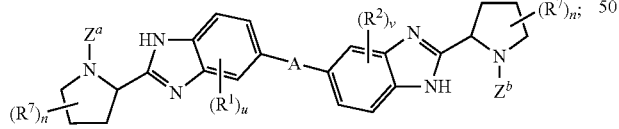

via a transition-metal catalyzed cross-coupling or metathesis reaction; amide or urea formation; ester or carbamate formation; or ether formation; wherein:

$Z^a$ and $Z^b$ are each independently an amino protecting group or —C(O)—$R^{12}$; $R^{12}$ is $C_1$-$C_8$ alkyl optionally substituted with amino, hydroxy, protected amino, or O($C_1$-$C_4$ alkyl);

ii) When $Z^a$ or $Z^b$ is an amino protecting group, fully or selectively deprotecting a compound of Formula (II-a) to give the corresponding amine of Formula (II-b):

(II-b)

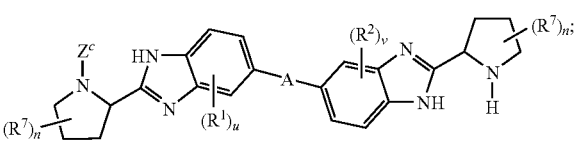

wherein $Z^c$ is hydrogen, an amino protecting group or —C(O)—$R^{12}$;

iii) Capping the released amino group of a compound of Formula (II-b) with LG-C(O)—$R^{12}$, wherein LG is a leaving group; to give the compound of Formula (II-c):

(II-c)

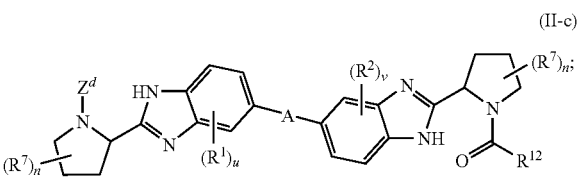

wherein $Z^d$ is an amino protecting group —C(O)—$R^{12}$; and iv) Repeated reaction sequence of deprotecting and capping (step ii-iii) to give the compound of Formula (II-d):

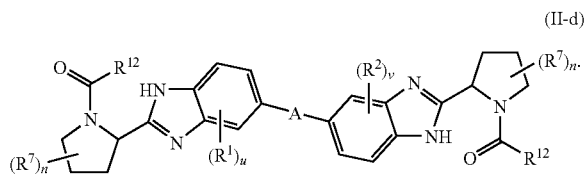

(II-d)

29. A compound represented by Formula (IIe) or (IIf):

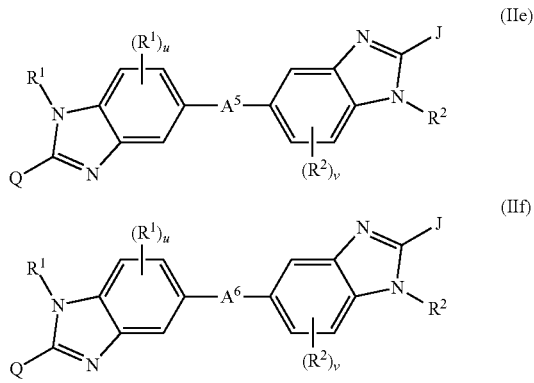

or a pharmaceutically acceptable salt thereof, wherein:
- $A^5$ is a linear aliphatic group containing an olefinic double bond, wherein said aliphatic group contains a group selected from C(O), S(O)$_2$, C(O)O, C(O)N(R$^{11}$), OC(O)O, OC(O)N(R$^{11}$), S(O)$_2$N(R$^{11}$), N(R$^{11}$)C(O)N(R$^{11}$), N(R$^{11}$)C(O)C(O)N(R$^{11}$), N(R$^{11}$)S(O)$_2$N(R$^{11}$), C(O)N(R$^{11}$)S(O)$_2$ and C(O)N(R$^{11}$)S(O)$_2$N(R$^{11}$);
- $A^6$ is a linear aliphatic group containing an alkynic triple bond, wherein said aliphatic group contains a group selected from C(O), S(O)$_2$, C(O)O, C(O)N(R$^{11}$), OC(O)O, OC(O)N(R$^{11}$), S(O)$_2$N(R$^{11}$), N(R$^{11}$)C(O)N(R$^{11}$), N(R$^{11}$)C(O)C(O)N(R$^{11}$), N(R$^{11}$)S(O)$_2$N(R$^{11}$), C(O)N(R$^{11}$)S(O)$_2$ and C(O)N(R$^{11}$)S(O)$_2$N(R$^{11}$);
- $R^1$ and $R^2$ at each occurrence are each independently selected from the group consisting of hydrogen, halogen, cyano, optionally substituted $C_1$-$C_4$ alkyl, —O—R$^{11}$, —NR$^a$R$^b$, —C(O)R$^{11}$, —CO$_2$R$^{11}$, and —C(O)NR$^a$R$^b$;
- $R^{11}$ at each occurrence is independently hydrogen or optionally substituted $C_1$-$C_8$ alkyl;
- $R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;
- u and v are each independently 1, 2, or 3;
- Q and J are each independently selected from:

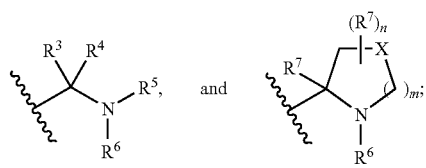

- $R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; or alternatively, $R^3$ and $R^4$ can be taken together with the carbon atom to which they are attached to form optionally substituted $C_3$-$C_8$ cycloalkyl or optionally substituted heterocyclic;
- $R^5$ at each occurrence is independently hydrogen, optionally substituted $C_1$-$C_8$ alkyl, or optionally substituted $C_3$-$C_8$ cycloalkyl;
- $R^6$ is selected from the group consisting of —C(O)—R$^{12}$, —C(O)—C(O)—R$^{12}$, —S(O)$_2$—R$^{12}$, and —C(S)—R$^{12}$;
- $R^{12}$ at each occurrence is independently selected from the group consisting of —O—R$^{11}$, —NR$^a$R$^b$, —R$^{13}$, and —NR$^c$R$^d$; wherein
- $R^{13}$ at each occurrence is independently selected from the group consisting of: hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;
- $R^c$ and $R^d$ at each occurrence are each independently selected from the group consisting of hydrogen, —R$^{13}$, —C(O)—R$^{13}$, —C(O)—OR$^{13}$, —S(O)$_2$—R$^{13}$, —C(O)N(R$^{13}$)$_2$, and —S(O)$_2$N(R$^{13}$)$_2$;
- m is 0, 1, or 2;
- n is 1, 2, 3, or 4;
- X at each occurrence is independently selected from O, S, S(O), SO$_2$, and C(R$^7$)$_2$; provided that when m is 0, X is C(R$^7$)$_2$; and
- $R^7$ at each occurrence is independently selected from the group consisting of: hydrogen, halogen, cyano, —O—R$^{11}$, —NR$^a$R$^b$, optionally substituted aryl, optionally substituted heteroaryl, and optionally substituted —$C_1$-$C_4$ alkyl; or two vicinal R$^7$ groups can be taken together with the two adjacent atoms to which they are attached to form a fused, optionally substituted $C_3$-$C_8$ cycloalkyl or optionally substituted heterocyclic ring; or alternatively two geminal R$^7$ groups can be taken together with the carbon atom to which they are attached to form a spiro, optionally substituted $C_3$-$C_8$ cycloalkyl or optionally substituted heterocyclic ring.

30. A compound represented by Formula (IIIb):

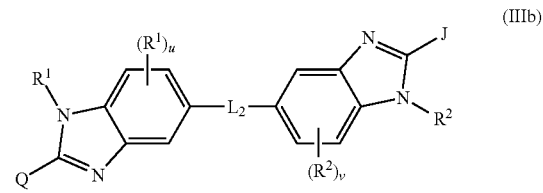

(IIIb)

or a pharmaceutically acceptable salt thereof, wherein:
- $L_2$ is a linear aliphatic group containing one to four carbons and two groups independently selected from the group consisting of O, S(O)$_2$, C(O)O, OC(O)O, OC(O)N(R$^{11}$), S(O)$_2$N(R$^{11}$), N(R$^{11}$)C(O)N(R$^{11}$), N(R$^{11}$)C(O)C(O)N(R$^{11}$), N(R$^{11}$)S(O)$_2$N(R$^{11}$), C(O)N(R$^{11}$)S(O)$_2$ and C(O)N(R$^{11}$)S(O)$_2$N(R$^{11}$);
- $R^1$ and $R^2$ at each occurrence are independently selected from the group consisting of hydrogen, halogen, cyano, optionally substituted $C_1$-$C_4$ alkyl, —O—R$^{11}$, —NR$^a$R$^b$, —C(O)R$^{11}$, —CO$_2$R$^{11}$, and —C(O)NR$^a$R$^b$;
- $R^{11}$ at each occurrence is independently hydrogen or optionally substituted $C_1$-$C_8$ alkyl;
- $R^a$ and $R^b$ at each occurrence are independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic and optionally substituted heteroaryl group;
u and v are each independently 1, 2, or 3;
Q and J are each independently selected from:

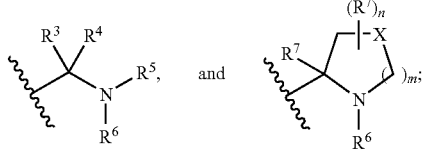

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; or alternatively, $R^3$ and $R^4$ can be taken together with the carbon atom to which they are attached to form optionally substituted $C_3$-$C_8$ cycloalkyl or optionally substituted heterocyclic;
$R^5$ at each occurrence is independently hydrogen, optionally substituted $C_1$-$C_8$ alkyl, or optionally substituted $C_3$-$C_8$ cycloalkyl;
$R^6$ is selected from the group consisting of —C(O)—$R^{12}$, —C(O)—C(O)—$R^{12}$, —S(O)$_2$—$R^{12}$, and —C(S)—$R^{12}$;
$R^{12}$ at each occurrence is independently selected from the group consisting of —O—$R^{11}$, $NR^aR^b$, —$R^{13}$, and —$NR^cR^d$; wherein
$R^{13}$ at each occurrence is independently selected from the group consisting of: hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;
$R^c$ and $R^d$ at each occurrence are each independently selected from the group consisting of hydrogen, —$R^{13}$, —C(O)—$R^{13}$, —C(O)—$OR^{13}$, —S(O)$_2$—$R^{13}$, —C(O)N($R^{13}$)$_2$, and —S(O)$_2$N($R^{13}$)$_2$;
m is 0, 1, or 2;
n is 1, 2, 3, or 4;
X at each occurrence is independently selected from O, S, S(O), SO$_2$, and C($R^7$)$_2$;
provided that when m is 0, X is C($R^7$)$_2$; and
$R^7$ at each occurrence is independently selected from the group consisting of: hydrogen, halogen, cyano, —O—$R^{11}$, —$NR^aR^b$, optionally substituted aryl, optionally substituted heteroaryl, and optionally substituted —$C_1$-$C_4$ alkyl; or two vicinal $R^7$ groups can be taken together with the two adjacent atoms to which they are attached to form a fused, optionally substituted $C_3$-$C_8$ cycloalkyl or optionally substituted heterocyclic ring; or alternatively two geminal $R^7$ groups can be taken together with the carbon atom to which they are attached to form a spiro, optionally substituted $C_3$-$C_8$ cycloalkyl or optionally substituted heterocyclic ring.

31. A compound represented by Formula (I):

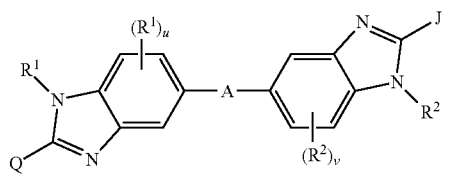

or a pharmaceutically acceptable salt thereof, wherein:
A is a group independently selected from S(O)$_2$, C(O)O, C(O)N($R^{11}$), OC(O)O, OC(O)N($R^{11}$), S(O)$_2$N($R^{11}$), N($R^{11}$)C(O)N($R^{11}$), N($R^{11}$)C(O)C(O)N($R^{11}$), N($R^{11}$)S(O)$_2$N($R^{11}$), C(O)N($R^{11}$)S(O)$_2$ and C(O)N($R^{11}$)S(O)$_2$N($R^{11}$);

$R^1$ and $R^2$ at each occurrence are each independently selected from the group consisting of hydrogen, halogen, cyano, optionally substituted $C_1$-$C_4$ alkyl, —O—$R^{11}$, —$NR^aR^b$, —C(O)$R^{11}$, —CO$_2R^{11}$, and —C(O)$NR^aR^b$;
$R^{11}$ at each occurrence is independently hydrogen or optionally substituted $C_1$-$C_8$ alkyl;
$R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;
u and v are each independently 1, 2, or 3;
Q and J are each independently selected from:

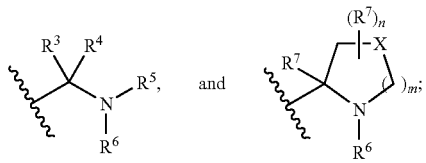

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; or alternatively, $R^3$ and $R^4$ can be taken together with the carbon atom to which they are attached to form optionally substituted $C_3$-$C_8$ cycloalkyl or optionally substituted heterocyclic;
$R^5$ at each occurrence is independently hydrogen, optionally substituted $C_1$-$C_8$ alkyl, or optionally substituted $C_3$-$C_8$ cycloalkyl;
$R^6$ is selected from the group consisting of —C(O)—$R^{12}$, —C(O)—C(O)—$R^{12}$, —S(O)$_2$—$R^{12}$, and —C(S)—$R^{12}$;
$R^{12}$ at each occurrence is independently selected from the group consisting of —O—$R^{11}$, —$NR^aR^b$, —$R^{13}$, and —$NR^cR^d$; wherein
$R^{13}$ at each occurrence is independently selected from the group consisting of: hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted;
$R^c$ and $R^d$ at each occurrence are each independently selected from the group consisting of hydrogen, —$R^{13}$, —C(O)—$R^{13}$, —C(O)—$OR^{13}$, —S(O)$_2$—$R^{13}$, —C(O)N($R^{13}$)$_2$, and —S(O)$_2$N($R^{13}$)$_2$;
m is 0, 1, or 2;
n is 1, 2, 3, or 4;
X at each occurrence is independently selected from O, S, S(O), SO$_2$, and C($R^7$)$_2$; provided that when m is 0, X is C($R^7$)$_2$; and
$R^7$ at each occurrence is independently selected from the group consisting of: hydrogen, halogen, cyano, —O—$R^{11}$, —$NR^aR^b$, optionally substituted aryl, optionally substituted heteroaryl, and optionally substituted —$C_1$-$C_4$ alkyl; or two vicinal $R^7$ groups can be taken together with the two adjacent atoms to which they are attached to form a fused, optionally substituted $C_3$-$C_8$ cycloalkyl or optionally substituted heterocyclic ring; or alternatively two geminal $R^7$ groups can be taken together with the carbon atom to which they are attached to form a spiro, optionally substituted $C_3$-$C_8$ cycloalkyl or optionally substituted heterocyclic ring.

* * * * *

UNITED STATES PATENT AND TRADEMARK OFFICE
CERTIFICATE OF CORRECTION

PATENT NO.       : 8,188,132 B2
APPLICATION NO.  : 12/702692
DATED            : May 29, 2012
INVENTOR(S)      : Yat Sun Or et al.

It is certified that error appears in the above-identified patent and that said Letters Patent is hereby corrected as shown below:

In the Claims:

At Column 128

In Claim 1, line 25, delete " 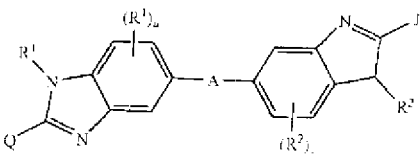 " and insert 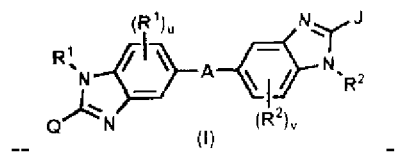 --; and

In Claim 1, line 55, delete " " and insert -- --.

At Column 130

In Claim 7, line 30, after OC(O)O, delete "OC(O)N($R_{11}$)," and insert -- OC(O)N($R^{11}$), --.

Signed and Sealed this
Seventh Day of May, 2013

Teresa Stanek Rea
*Acting Director of the United States Patent and Trademark Office*